United States Patent
Pop et al.

(10) Patent No.: US 11,214,777 B2
(45) Date of Patent: *Jan. 4, 2022

(54) METHOD FOR USING LIPASE ENZYMES FOR CLEANING

(71) Applicant: BASF SE, Ludwigshafen (DE)

(72) Inventors: Cristina Pop, San Diego, CA (US); Claudia Esper, Ludwigshafen (DE); Oliver Spangenberg, Ludwigshafen (DE); Katie Kline, San Diego, CA (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/612,560

(22) PCT Filed: May 10, 2018

(86) PCT No.: PCT/US2018/031969
§ 371 (c)(1),
(2) Date: Nov. 11, 2019

(87) PCT Pub. No.: WO2018/209026
PCT Pub. Date: Nov. 15, 2018

(65) Prior Publication Data
US 2020/0208082 A1  Jul. 2, 2020

Related U.S. Application Data

(60) Provisional application No. 62/505,500, filed on May 12, 2017.

(51) Int. Cl.
*C12N 9/20* (2006.01)
*C11D 3/386* (2006.01)
*A21D 8/04* (2006.01)

(52) U.S. Cl.
CPC ............ *C12N 9/20* (2013.01); *C11D 3/38627* (2013.01); *C11D 3/38636* (2013.01); *C11D 3/38645* (2013.01); *A21D 8/042* (2013.01); *C12Y 203/02013* (2013.01); *C12Y 301/01003* (2013.01); *C12Y 301/01004* (2013.01); *C12Y 301/0105* (2013.01); *C12Y 301/01013* (2013.01); *C12Y 301/01026* (2013.01); *C12Y 301/01072* (2013.01); *C12Y 301/01074* (2013.01); *C12Y 301/03008* (2013.01); *C12Y 301/03026* (2013.01); *C12Y 301/04003* (2013.01); *C12Y 301/04004* (2013.01); *C12Y 302/01001* (2013.01); *C12Y 302/01002* (2013.01); *C12Y 302/01004* (2013.01); *C12Y 302/0106* (2013.01); *C12Y 302/01008* (2013.01); *C12Y 302/01032* (2013.01); *C12Y 302/01133* (2013.01)

(58) Field of Classification Search
CPC .............................. C12N 9/20; C11D 3/38627
See application file for complete search history.

(56) References Cited

U.S. PATENT DOCUMENTS

| | | | |
|---|---|---|---|
| 5,614,188 A | 3/1997 | Urano et al. | |
| 5,869,438 A | 2/1999 | Svendsen et al. | |
| 6,645,749 B2 * | 11/2003 | Vind | A21D 8/042 435/195 |
| 8,022,027 B2 | 9/2011 | Souter et al. | |
| 2002/0094367 A1 | 7/2002 | Fuglsang et al. | |
| 2003/0003561 A1 | 1/2003 | Vind | |
| 2009/0217463 A1 | 9/2009 | Souter et al. | |
| 2014/0134707 A1 | 5/2014 | Juntunen et al. | |
| 2018/0346893 A1 | 12/2018 | Hansen et al. | |
| 2018/0371438 A1 | 12/2018 | Saikia et al. | |
| 2019/0053501 A1 | 2/2019 | Pop et al. | |

FOREIGN PATENT DOCUMENTS

| | | | |
|---|---|---|---|
| RU | 2395565 C2 | 7/2010 | |
| WO | WO-93/00924 A1 | 1/1993 | |
| WO | WO-94/014963 A1 | 7/1994 | |
| WO | WO-9901531 A1 * | 1/1999 | ......... C11D 3/38627 |
| WO | WO-02/00852 A2 | 1/2002 | |
| WO | WO-03/035878 A2 | 5/2003 | |
| WO | WO-03/89620 A2 | 10/2003 | |
| WO | WO-2005/032496 A2 | 4/2005 | |
| WO | WO-2005/086900 A2 | 9/2005 | |
| WO | WO-2006/031699 A2 | 3/2006 | |
| WO | WO-2008/036863 A2 | 3/2008 | |
| WO | WO-2009/133177 A1 | 11/2009 | |
| WO | WO-2011/046812 A1 | 4/2011 | |
| WO | WO-2017/142904 A1 | 8/2017 | |
| WO | WO-2018/209018 A1 | 11/2018 | |

OTHER PUBLICATIONS

C7YUZ1_NECH7. UnitProtKB. Mar. 2016.*
Coleman et al., The genome of Nectria haematococca: contribution of supernumerary chromosomes to gene expansion, PLoS Genet., 5(8):e 1000618 (Aug. 2009).
Gerits, et al., "Single run HPLC separation coupled to evaporative light scattering detection unravels wheat flour endogenous lipid redistribution during bread dough making", LWT—Food Science and Technology, vol. 53, Issue 2, Oct. 2013, pp. 426-433.
International Application No. PCT/US18/31969, International Search Report and Written Opinion, dated Aug. 7, 2018.
International Application No. PCT/US2018/031956, International Search Report and Written Opinion, dated Oct. 3, 2018.
NCBI Reference Sequence: XP_003050606.1, hypothetical protein NECHADRAFT_49364 [[Nectria] haematococca mpVI 77-13-4], (Aug. 28, 2009).

(Continued)

*Primary Examiner* — Yong D Pak
(74) *Attorney, Agent, or Firm* — Marshall, Gerstein & Borun LLP

(57) ABSTRACT

A method for removing a stain from a surface using lipase enzymes, and a formulation comprising a lipase enzyme.

8 Claims, No Drawings
Specification includes a Sequence Listing.

(56) References Cited

OTHER PUBLICATIONS

Needleman, et al., "A general method applicable to the search for similarities in the amino acid sequence of two proteins", Journal of Molecular Biology, vol. 48, Issue 3, Mar. 28, 1970, pp. 443-453.
Schaffarczyk et al., Lipases in wheat breadmaking: analysis and functional effects of lipid reaction products, J. Agric. Food Chem., 62(32):8229-37 (Aug. 2014).
European Search Report for EP Patent Application No. 18797619.6, dated Jan. 29, 2021, 3 pages.
Liu et al., "A novel low-temperature resistant alkaline lipase from a soda lake fungus strain Fusarium solani N4-2 for detergent formulation", Biochemical Engineering Journal, vol. 46, Issue 3, Nov. 1, 2009, pp. 265-270.
"RecName: Full=Lipase_3 domain-containing protein {ECO:0000259|Pfam:PF01764}", DATABASE UniProt [Online], retrieved from EBI Database accession No. C7YUZ1, XP002801892, Oct. 13, 2009, 1 page.
European Search Report for EP Patent Application No. 18798843.1, dated Feb. 11, 2021, 4 pages.
Moayedallaie, et al., "Bread improvers: Comparison of a range of lipases with a traditional emulsifier", Food Chemistry, vol. 122, Issue 3, Oct. 1, 2010, pp. 495-499.

\* cited by examiner

METHOD FOR USING LIPASE ENZYMES FOR CLEANING

This application is a National Stage application of International Application No. PCT/US2018/031969, filed May 10, 2018, which claims priority to U.S. Provisional Patent Application No. 62/505,500, filed on May 12, 2017.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "171443_Seqlisting.txt", which was created on Oct. 24, 2019 and is 4,369 bytes in size. The subject matter of the Sequence Listing is incorporated herein in its entirety by reference.

TECHNICAL FIELD

Genetically engineered lipase enzymes, compositions comprising the enzymes, and methods of using the enzymes or compositions comprising the enzymes. The genetically engineered lipase enzymes are useful in many different applications such as laundry detergents, dish washing detergents, and cleaning products for homes, industry, vehicle care, baking, animal feed, pulp and paper processing, starch processing, and ethanol production. Lipases have been employed in the removal of fatty stains and have been added to various compositions such as cleaning products. Current cleaning and/or fabric care compositions comprise formulations of many active ingredients that impact with the ability of lipases to remove fatty stains. Thus, the need exists for genetically engineered lipase enzymes that can function in the harsh environment of compositions used for cleaning.

SUMMARY OF THE INVENTION

1. A detergent formulation comprising: at least one polypeptide according to the amino acid sequence of SEQ ID NO:1, or at least one polypeptide having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity with the amino acid sequence of SEQ ID NO: 1 having lipase activity, and at least one detergent component.
2. The detergent formulation according to claim 1, wherein the polypeptide comprises at least one amino acid residue insertion, deletion, or substitution at the amino acid residue position number: 23, 33, 82, 83, 84, 85, 160, 199, 254, 255, 256, 258, 263, 264, 265, 268, 308, 311, or any combination thereof to the amino acid sequence of SEQ ID NO: 1, and the polypeptide has lipase activity.
3. The detergent formulation according to claim 2, wherein the at least one amino acid substitution is selected from the group consisting of: Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, Y311E, or any combination thereof to the amino acid sequence of SEQ ID NO: 1, and the polypeptide has lipase activity
4. The detergent formulation according to claims 2-3, wherein the polypeptide comprises an amino acid sequence that is at least 80% identical to the amino acid sequence as set forth in SEQ ID NO: 1, wherein the polypeptide has at least one single amino acid substitution to the amino acid sequence of SEQ ID NO: 1, and the one single amino acid substitution is selected from the group consisting of: Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, Y311E, or any combination thereof to the amino acid sequence of SEQ ID NO:1; wherein the polypeptide has lipase activity.
5. The detergent formulation according to claims 2-4, wherein the polypeptide comprising an amino acid sequence that is at least 80% identical to the amino acid sequence as set forth in SEQ ID NO: 1, wherein the variant polypeptide has a combination of amino acid substitutions as set forth in Table: 1, and the polypeptide has lipase activity.
6. A method of cleaning, comprising the steps of
   (a) providing a surface to be cleaned from fatty stains;
   (b) providing the detergent formulation according to claims 1-5;
   (c) contacting the surface to be cleaned from fatty stains of (a) with the detergent of (b);
   wherein the polypeptide in the detergent removes the fatty stain from the surface to be cleaned from fatty stains.
7. The detergent formulation of Claims 1-5, further comprising adding a second enzyme selected from one or more of the group consisting of: a second lipase, an amylase, a protease, a cellulase, a mannanase, a laccase, a pectinase, and a nuclease.
8. The method of Claim 6, wherein the surface to be cleaned from fatty stains is: a cloth, a textile, a fabric, a hard surface, or a dish.
9. The method of Claim 6, wherein the surface to be cleaned from fatty stains comprises a stain selected from: lipstick, sebum, mustard, olive oil, coco, chocolate, chocolate mousse, chocolate ice cream, chocolate drink, groundnut oil, beef fat, Indian curry, Napoli tomato, make up, blood beef fat, salad dressing, egg yolk, food, frying fat, curry, mediterranean sauce, curry oil sauce, balsamic, hamburger grease, butter fat.
10. The detergent formulation according to claims 1-5, wherein the formulation is a laundry detergent, a hard surface cleaner, a dishwashing detergent, or a personal hygiene product.
11. The detergent formulation of Claims 1-10, wherein the at least one detergent component is selected from: surfactants, builders, polymers, alkaline, bleaching systems, fluorescent whitening agents, suds suppressors and stabilizers, hydrotropes, rheology modifiers, preservatives, and corrosion inhibitors in amounts effective in washing or cleaning performance or effective in maintaining the physical characteristics of the detergent.

12. The detergent formulation of according to claims 1-11, wherein detergent is a liquid, a gel, a paste, a soap bar, a powder, or a granulated solid.

DETAILED DESCRIPTION OF THE INVENTION

An enzyme is a biological molecule (polypeptide) comprising a sequence of amino acid residues, wherein the enzyme can catalyze a reaction. Enzyme names are determined based on the recommendations of the Nomenclature Committee of the International Union of Biochemistry and Molecular Biology (IUBMB). Enzymes are defined by an EC (Enzyme Commission) number, recommended name, alternative names (if any), catalytic activity, and other factors. Enzymes are also known as a polypeptide, a protein, a peptide, or are described in patents and patent applications by a sequence identification number (SEQ ID NO.) Alternative names for enzyme can be used interchangeably.

Enzymes are obtained from or derived from many different sources including: plants; animals; bacteria, archaea, fungi, yeast, environmental samples containing DNA that encodes an enzyme, or enzymes can be synthetic generated in a laboratory. For example, bacterial sources of enzymes include enzymes derived from *Bacillus, Streptomyces, E. coli* and *Pseudomonas*; fungal sources of enzymes include enzymes derived from *Aspergillus, Fusarium, Thermomyces* and *Trichoderma*; yeast sources of enzymes include enzymes derived from *Pichia*, and *Saccharomyces*.

Different classes of enzymes are known to be useful in detergents and cleaning products including: lipase, amylase, protease, cellulase, mannanase, pectate lyase, and nuclease; however, there is a need in the industry to provide a lipase that has more activity, temperature profile, pH profile, has improved performance (stain removal), stability in presence of protease, reduces the amount of surfactant in a detergent formulation, no odor, or a combination thereof. The variant polypeptide lipase enzymes address these industrial needs.

The World Intellectual Property Office (WIPO) Standard ST.25 (1998) provides that the amino acid residues should be represented in the sequence listing using the following three-letter symbols with the first letter as a capital. The table below provides an overview of the amino acid identifiers as well as the corresponding DNA codons that encode the amino acid using the standard genetic standard. The DNA codons that encode amino acid residues can be different depending organism that is used and slightly different tables for translation of the genetic code may apply. A compilation of such non-standard code translation tables is maintained at the NCBI. For reference see e.g. https://www.ncbi.nlm.nih.gov/Taxonomy/Utils/wprintgc.cgi.

| Amino Acids | | | Nucleic Acids |
|---|---|---|---|
| Name | 3 letter code | 1 letter code | DNA codons |
| Alanine | Ala | A | GCA, GCC, GCG, GCT |
| Arginine | Arg | R | AGA, AGG, CGA, CGC, CGG, CGT |
| Asparagine | Asn | N | AAC, AAT |
| Aspartic acid; (Aspartate) | Asp | D | GAC, GAT |
| Cysteine | Cys | C | TGC, TGT |

-continued

| Amino Acids | | | Nucleic Acids |
|---|---|---|---|
| Name | 3 letter code | 1 letter code | DNA codons |
| Glutamic acid; (Glutamate) | Glu | E | GAA, GAG |
| Glutamine | Gln | Q | CAA, CAG |
| Glycine | Gly | G | GGA, GGC, GGG, GGT |
| Histidine | His | H | CAC, CAT |
| Isoleucine | Ile | I | ATA, ATC, ATT |
| Leucine | Leu | L | CTA, CTC, CTG, CTT, TTA, TTG |
| Lysine | Lys | K | AAA, AAG |
| Methionine | Met | M | ATG |
| Phenylalanine | Phe | F | TTC, TTT |
| Proline | Pro | P | CCA, CCC, CCG, CCT |
| Serine | Ser | S | AGC, AGT, TCA, TCC, TCG, TCT |
| Threonine | Thr | T | ACA, ACC, ACG, ACT |
| Tryptophan | Trp | W | TGG |
| Tyrosine | Tyr | Y | TAC TAT |
| Valine | Val | V | GTA, GTC, GTG, GTT |

A "parent" polypeptide amino acid sequence is the starting sequence for introduction of mutations (e.g. by introducing one or more amino acid substitutions, insertions, deletions, or a combination thereof) to the sequence, resulting in "variants" of the parent polypeptide amino acid sequences. A parent includes: A wild-type polypeptide amino acid sequence or synthetically generated polypeptide amino acid sequence that is used as starting sequence for introduction of (further) changes A "variant polypeptide" refers to an enzyme that differs from its parent in its amino acid sequence. While the definition below describes variants in the context of amino acid changes, nucleic acids may be similarly modified, e.g. by substitutions.

The invention relates to a polypeptide having lipase activity comprising an amino acid sequence that is at least at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the full length amino acid sequence of SEQ ID NO:1.

Said polypeptide may comprise changes selected from amino acid residue insertion, deletion, or substitution. Said polypeptide may comprise at least one substitution at least one of the following amino acid residue positions: 23, 33, 82, 83, 84, 85, 160, 199, 254, 255, 256, 258, 263, 264, 265, 268, 308, 311, or any combination thereof to the amino acid sequence of SEQ ID NO:1. The number of positions is based on the amino acid sequence provided as SEQ ID NO:1.

Specifically, the polypeptide of the invention may comprise at least one amino acid substitution selected from Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, and Y311E. In one embodiment, the polypeptide comprises more than one of said substitutions.

The invention relates to a polypeptide having lipase activity, wherein the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the full length amino acid sequence as set forth in SEQ ID NO: 1, wherein the variant polypeptide has a combination of amino acid modifications to the amino acid sequence of SEQ ID NO:1 selected from the group consisting of: combinations as described in Example 1, Table 1 of this description.

In one embodiment, the variant polypeptide is a polypeptide according to SEQ ID NO: 1 comprising at least a substitution at position 83, wherein the substitution is selected from S83D, S83H, S83I, S83N, S83R, S83T, and S83Y. Preferably, the substitution at position 83 is selected from S83H, S83I, S83N, and S83Y. In one embodiment, the variant polypeptide is a polypeptide according to SEQ ID NO: 1 comprising at least a substitution at position 85, wherein the substitution is selected from I85A, I85C, I85F, I85H, I85L, I85M, I85P, I85S, I85T, I85V, and I85Y. Preferably, the substitution at position 85 is selected from I85L, I85T, and I85V. In one embodiment, the variant polypeptide is a polypeptide according to SEQ ID NO: 1 comprising at least a substitution at position 255, wherein the substitution is selected from I255A, I255L. In one embodiment, the variant polypeptide is a polypeptide according to SEQ ID NO: 1 comprising at least a substitution at position 264, wherein the substitution is selected from T264A, T264D, T264G, T264I, T264L, T264N, T264S. Preferably, the substitution at position 264 is selected from T264A, T264D, T264N, and T264S. In one embodiment, the variant polypeptide is a polypeptide according to SEQ ID NO: 1 comprising at least a substitution at position 265, wherein the substitution is selected from D265A, D265G, D265K, D265L, D265N, D265S, and D265T. Preferably, the substitution at position 265 is selected from D265A, D265G, D265S, and D265T.

In one embodiment, the variant polypeptide is a polypeptide according to SEQ ID NO: 1 comprising at least a substitution at position 83 and a substitution at position 85, wherein the substitution at position 83 is selected from S83D, S83H, S83I, S83N, S83R, S83T, and S83Y, and the substitution at position 85 is selected from I85A, I85C, I85F, I85H, I85L, I85M, I85P, I85S, I85T, I85V, and I85Y. Preferably, the substitution at position 83 is selected from S83H, and S83I, and the substitution at position 85 is selected from I85L, I85P, I85T, and I85V. The substitution at position 83 may be S83H, and the substitution at position 85 may be selected from I85L, I85P, and I85T. The substitution at position 83 may be S83I, and the substitution at position 85 may be I85V.

In one embodiment, the variant polypeptide is a polypeptide according to SEQ ID NO: 1 comprising at least a substitution at position 83 and a substitution at position 255, wherein the substitution at position 83 is selected from S83D, S83H, S83I, S83N, S83R, S83T, and S83Y, and the substitution at position 255 is selected from I255A, and I255L. Preferably, the substitution at position 83 is selected from S83H, S83N, and S83Y, and the substitution at position 264 is selected from T264A, T264D, T264N, and T264S. The substitution at position 83 may be selected from S83H, S83N, S83T and S83Y, and the substitution at position 255 may be I255A.

In one embodiment, the variant polypeptide is a polypeptide according to SEQ ID NO: 1 comprising at least a substitution at position 83 and a substitution at position 264, wherein the substitution at position 83 is selected from S83D, S83H, S83I, S83N, S83R, S83T, and S83Y, and the substitution at position 264 is selected from T264A, T264D, T264G, T264I, T264L, T264N, and T264S. Preferably, the substitution at position 83 is selected from S83H, S83N, and S83Y, and the substitution at position 264 is selected from T264A, T264D, T264N, and T264S. The substitution at position 83 may be S83H, and the substitution at position 264 may be selected from T264A, T264N, and T264S. The substitution at position 83 may be S83N, and the substitution at position 264 may be selected from T264A, T264D, T264N, and T264S. The substitution at position 83 may be S83Y, and the substitution at position 264 may be selected from T264A, and T264S.

In one embodiment, the variant polypeptide is a polypeptide according to SEQ ID NO: 1 comprising at least a substitution at position 83 and a substitution at position 265, wherein the substitution at position 83 is selected from S83D, S83H, S83I, S83N, S83R, S83T, and S83Y, and the substitution at position 265 is selected from D265A, D265G, D265K, D265L, D265N, D265S, and D265T. Preferably, the substitution at position 83 is selected from S83H, S83I, S83N, S83T and S83Y, and the substitution at position 265 is selected from D265A, D265G, D265S, and D265T. The substitution at position 83 may be S83H, and the substitution at position 265 may be selected from D265A, D265G, D265S, and D265T. The at position 83 may be S83I, and the substitution at position 265 may be selected from D265G, and D265S. The substitution at position 83 may be S83N, and the substitution at position 265 may be selected from D265A, D265G, D265S, and D265T. The substitution at position 83 may be S83T, and the substitution at position 265 may be selected from D265A, D265S, and D265T. The substitution at position 83 may be S83Y, and the substitution at position 265 may be D265T.

In one embodiment, the variant polypeptide is a polypeptide according to SEQ ID NO: 1 comprising at least a substitution at position 85 and a substitution at position 265, wherein the substitution at position 85 is selected from I85A, I85C, I85F, I85H, I85L, I85M, I85P, I85S, I85T, I85V, and I85Y, and the substitution at position 265 is selected from D265A, D265G, D265K, D265L, D265N, D265S, and D265T. Preferably, the substitution at position 85 is selected from I85A, I85H, I85L, I85P, I85S, I85T, and I85V, and the substitution at position 265 is selected from D265A, D265G, D265S, and D265T. The substitution at position 85 may be I85A, and the substitution at position 265 may be D265T. The substitution at position 85 may be I85H, and the substitution at position 265 may be D265A. The substitution at position 85 may be I85L, and the substitution at position 265 may be selected from D265A, D265G, D265S, and D265T. The substitution at position 85 may be I85P, and the substitution at position 265 may be D265A. The substitution at position 85 may be I85S, and the substitution at position 265 may be D265S. The substitution at position 85 may be I85T, and the substitution at position 265 may be selected from D265G, D265S, and D265T. The substitution at position 85 may be I85V, and the substitution at position 265 may be selected from D265A, D265G, D265S, and D265T.

In one embodiment, the variant polypeptide is a polypeptide according to SEQ ID NO: 1 comprising at least a substitution at position 85 and a substitution at position 255, wherein the substitution at position 85 is selected from I85A, I85C, I85F, I85H, I85L, I85M, I85P, I85S, I85T, I85V, and I85Y, and wherein the substitution at position 255 is selected from I255A, and I255L. The variant polypeptide may comprise a I85H substitution, and a I255A substitution. The variant polypeptide may comprise a I85L substitution, and a I255A substitution. The variant polypeptide may comprise a I85S substitution, and a I255A substitution. The variant polypeptide may comprise a I85V substitution, and a I255A substitution.

In one embodiment, the variant polypeptide is a polypeptide according to SEQ ID NO: 1 comprising at least a substitution at position 83, a substitution at position 85, and a substitution at position 255, wherein the substitution at position 83 is selected from S83D, S83H, S83I, S83N, S83R, S83T, and S83Y, wherein the substitution at position 85 is selected from I85A, I85C, I85F, I85H, I85L, I85M, I85P, I85S, I85T, I85V, and I85Y, and wherein the substitution at position 255 is selected from I255A, and I255L. The variant polypeptide may comprise a S83H substitution, a substitution at position 85 which is selected from I85A, I85L, I85P, I85S, I85T, and I85V, and a I255A substitution. The variant polypeptide may comprise a S83N substitution, a substitution at position 85 which is selected from I85L, and I85V, and a I255A substitution. The variant polypeptide may comprise a S83T substitution, a substitution at position 85 which is selected from I85H, and I85V, and a I255A substitution. The variant polypeptide may comprise a S83Y substitution, a substitution at position 85 which is selected from I85A, and I85V, and a I255A substitution.

In one embodiment, the variant polypeptide is a polypeptide according to SEQ ID NO: 1 comprising at least a substitution at position 85 and a substitution at position 264, wherein the substitution at position 85 is selected from I85A, I85C, I85F, I85H, I85L, I85M, I85P, I85S, I85T, I85V, and I85Y, and wherein the substitution at position 264 is selected from T264A, T264D, T264N, and T264S. The variant polypeptide may comprise a I85A substitution, and a T264A substitution. The variant polypeptide may comprise a I85L substitution, and a T264S substitution. The variant polypeptide may comprise a I85S substitution, and a T264A substitution. The variant polypeptide may comprise a I85T substitution, and a T264A substitution. The variant polypeptide may comprise a I85V substitution, and a substitution at position 264 which is selected from T264A, T264D, T264N, and T264S.

In one embodiment, the variant polypeptide is a polypeptide according to SEQ ID NO: 1 comprising at least a substitution at position 255 and a substitution at position 264, wherein the substitution at position 255 is selected from I255A, and I255L, and wherein the substitution at position 264 is selected from T264A, T264D, T264N, and T264S. The variant polypeptide may comprise a I255A substitution, and a substitution at position 264 which is selected from T264A, T264D, T264N, and T264S.

In one embodiment, the variant polypeptide is a polypeptide according to SEQ ID NO: 1 comprising at least a substitution at position 255 and a substitution at position 265, wherein the substitution at position 255 is selected from I255A, and I255L, and wherein the substitution at position 265 is selected from T264A, T264D, T264N, and T264S. The variant polypeptide may comprise a I255A substitution, and a substitution at position 265 which is selected from D265A, D265G, D265K, D265L, D265N, D265S, and D265T. The variant polypeptide may comprise a I255A substitution, and a substitution at position 265 which is selected from D265A, D265G, D265S, and D265T. The variant polypeptide may comprise a I255A substitution, and a D265S substitution.

In one embodiment, the variant polypeptide is a polypeptide according to SEQ ID NO: 1 comprising at least a substitution at position 264 and a substitution at position 265, wherein the substitution at position 264 is selected from T264A, T264D, T264N, and T264S, and wherein the substitution at position 265 is selected from D265A, D265G, D265K, D265L, D265N, D265S, and D265T. The variant polypeptide may comprise a T264A substitution, and a substitution at position 265 which is selected from D265A, D265G, D265S, and D265T. The variant polypeptide may comprise a T264D substitution, and a substitution at position 265 which is selected from D265A, and D265T. The variant polypeptide may comprise a T264N substitution, and a substitution at position 265 which is selected from D265A, and D265T. The variant polypeptide may comprise a T264S substitution, and a substitution at position 265 which is selected from D265A, D265G, D265S, and D265T.

In one embodiment, the variant polypeptide is a polypeptide according to SEQ ID NO: 1 comprising at least a substitution at position 85 and a substitution at position 265, wherein the substitution at position 85 is selected from I85A, I85C, I85F, I85H, I85L, I85M, I85P, I85S, I85T, I85V, and I85Y, and the substitution at position 265 is selected from D265A, D265G, D265K, D265L, D265N, D265S, and D265T, further comprises a substitution at position 264, wherein the substitution is selected from T264A, T264D, T264N, and T264S. The variant polypeptide may comprise a I85A substitution, a T264A substitution, and a D265T substitution. The variant polypeptide may comprise a I85L substitution, a T264S substitution and a substitution at position 265 which is selected from D265A, D265G, D265S, and D265T. The variant polypeptide may comprise a I85S substitution, a T264A substitution and a D265T substitution. The variant polypeptide may comprise a I85T substitution, a T264A substitution and a substitution at position 265 which is selected from D265G, D265S, and D265T. The variant polypeptide may comprise a I85V substitution, a substitution at position 264 which is selected from T264A, T264D, T264N, and T264S, and a substitution at position 265 which is selected from D265A, D265G, D265S, and D265T.

In one embodiment, the variant polypeptide is a polypeptide according to SEQ ID NO: 1 comprising at least a substitution at position 85 and a substitution at position 265, wherein the substitution at position 85 is selected from I85A, I85C, I85F, I85H, I85L, I85M, I85P, I85S, I85T, I85V, and I85Y, and the substitution at position 265 is selected from D265A, D265G, D265K, D265L, D265N, D265S, and D265T, further comprises a substitution at position 255, wherein the substitution is selected from I255A, and I255L. The variant polypeptide may comprise a I85H substitution, a I255A substitution, and a substitution D265A substitution. The variant polypeptide may comprise a I85L substitution, a I255A substitution and a substitution at position 265 which is selected from D265A, D265G, D265S, and D265T. The variant polypeptide may comprise a I85S substitution, a I255A substitution and a D265T substitution. The variant polypeptide may comprise a I85V substitution, a I255A substitution, and a substitution at position 265 which is selected from D265A, D265G, D265S, and D265T.

In one embodiment, the variant polypeptide is a polypeptide according to SEQ ID NO: 1 comprising at least a substitution at position 85, a substitution at position 265, a substitution at position 255, and a substitution at position 264, wherein the substitution at position 85 is selected from I85A, I85C, I85F, I85H, I85L, I85M, I85P, I85S, I85T, I85V, and I85Y, wherein the substitution at position 265 is selected from D265A, D265G, D265K, D265L, D265N, D265S, and D265T, wherein the substitution at position 255, is selected from I255A and I255L, and wherein the substitution at position 264 is selected from T264A, T264D, T264N, and T264S. The variant polypeptide may comprise a I85L substitution, a I255A substitution, a T264S substitution, and a substitution at position 265 which is selected from D265A, D265G, D265S, and D265T. The variant polypeptide may comprise a I85S substitution, a I255A substitution, a T264A substitution, and a D265T substitution. The variant polypeptide may comprise a I85V substitution, a I255A substitution, a substitution at position 264 which is selected from T264A, T264G, T264S, and T264T, and a substitution at position 265 which is selected from D265A, D265G, D265S, and D265T.

In one embodiment, the variant polypeptide is a polypeptide according to SEQ ID NO: 1 comprising at least a substitution at position 83, a substitution at position 85, and a substitution at position 264 and/or position 265, wherein the substitution at position 83 is selected from S83D, S83H, S83I, S83N, S83R, S83T, and S83Y, wherein the substitution at position 85 is selected from I85A, I85C, I85F, I85H, I85L, I85M, I85P, I85S, I85T, I85V, and I85Y, wherein the substitution at position 264 is selected from T264A, T264D, T264N, and T264S, and wherein the substitution at position 265 is selected from D265A, D265G, D265K, D265L, D265N, D265S, and D265T. The variant polypeptide may comprise a S83H substitution, a substitution at position 85 which is selected from I85A, I85L, I85P, I85S, I85T, and I85V, a substitution at position 264 which is selected from T264A, T264N, and T264S, and a substitution at position 265 which is selected from D265A, D265G, D265S, and D265T. The variant polypeptide may comprise a S83H substitution, a I85L substitution, and a D265G substitution. The variant polypeptide may comprise a S83H substitution, a I85L substitution, a T264A substitution, and a D265T substitution. The variant polypeptide may comprise a S83N substitution, a substitution at position 85 which is selected from I85L, and I85V, a substitution at position 264 which is selected from T264A, T264D, T264N, and T264S, and a substitution at position 265 which is selected from D265A, D265G, D265S, and D265T. The variant polypeptide may comprise a S83Y substitution, a substitution at position 85 which is selected from I85A, and I85V, a substitution at position 264 which is selected from T264A, and T264S, and a D265T substitution.

In one embodiment, the variant polypeptide is a polypeptide according to SEQ ID NO: 1 comprising at least a substitution at position 83, a substitution at position 85, and a substitution at position 255, may further comprise a substitution at position 264 and/or position 265, wherein the substitution at position 83 is selected from S83D, S83H, S83I, S83N, S83R, S83T, and S83Y, wherein the substitution at position 85 is selected from I85A, I85C, I85F, I85H, I85L, I85M, I85P, I85S, I85T, I85V, and I85Y, wherein the substitution at position 255 is selected from I255A, and I255L, wherein the substitution at position 264 is selected from T264A, T264D, T264N, and T264S, and wherein the substitution at position 265 is selected from D265A, D265G, D265K, D265L, D265N, D265S, and D265T. The variant polypeptide may comprise a S83H substitution, a substitution at position 85 which is selected from I85A, I85L, I85P, I85S, I85T, and I85V, a I255A substitution, a substitution at position 264 which is selected from T264A, T264N, and T264S, and a substitution at position 265 which is selected from D265A, D265G, D265S, and D265T. The variant polypeptide may comprise a S83N substitution, a substitution at position 85 which is selected from I85L, and I85V, a I255A substitution, a substitution at position 264 which is selected from T264A, T264D, T264N, and T264S, and a substitution at position 265 which is selected from D265A, D265G, D265S, and D265T. The variant polypeptide may comprise a S83Y substitution, a substitution at position 85 which is selected from I85A, and I85V, I255A substitution, a substitution at position 264 which is selected from T264A, and T264S, and a D265T substitution. In one embodiment, the variant polypeptide is a polypeptide according to SEQ ID NO: 1 comprising besides the combinations of substitutions disclosed above, at least one of the following additional substitutions: K160N, I254L, I256D, D263R, T268G.

The invention relates to a variant polypeptide having lipase activity, wherein the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the full length amino acid sequence as set forth in SEQ ID NO: 1, and the variant polypeptide has an increase in enzyme activity, pH-stability, stability against proteolytic degradation and stability in detergent formulation, or any combination thereof when compared to the lipase of SEQ ID NO: 1.

"Substitutions" are described by providing the original amino acid followed by the number of the position within the amino acid sequence, followed by the substituted amino acid. A specific amino acid residue may be substituted with any of the 19 amino acid residues different from the original one. For example, the substitution of histidine at position 120 with alanine is designated as "His120Ala" or "H120A". Combinations of substitutions, are described by inserting comas between the amino acid residues, for example: K24E, D25P, L27H, A141R, G203I, S220L, S398P; represent a combination of seven different amino acid residues substitutions when compared to a parent polypeptide.

Amino acid deletions are described by providing the original amino acid of the parent enzyme followed by the number of the position within the amino acid sequence, followed by *. Accordingly, the deletion of glycine at position 150 is designated as "Gly150*" or "G150*". Alternatively, deletions are indicated by e.g. "deletion of D183 and G184".

Amino acid insertions are described by providing the original amino acid of the parent enzyme followed by the number of the position within the amino acid sequence, followed by the original amino acid and the additional amino acid. For example, an insertion at position 180 of lysine next to glycine is designated as "Gly180GlyLys" or "G180GK". When more than one amino acid residue is inserted, such as e.g. a Lys and Ala after Gly180 this may be indicated as: Gly180GlyLysAla or G195GKA.

The invention relates to fragments of the inventive polypeptide variants herein, wherein said polypeptide fragments have lipase activity.

A "Fragment", or "subsequence" as used herein are a portion of a polynucleotide or an amino acid sequence, wherein the fragments or subsequences retain or encode for at least one functional activity of the sequence to which it is related.

The term "functional fragment" refers to any nucleic acid or amino acid sequence which comprises merely a part of the full length amino acid sequence, respectively, but still has the same or similar activity and/or function. The fragment comprises at least 70%, at least 80%, at least 85%, at least 90%, at least 95%, at least 96%, at least 97%, at least 98%, at least 99% of the original sequence. The functional fragment comprises contiguous nucleic acids or amino acids compared to the original nucleic acid or original amino acid sequence, respectively.

The invention relates to a variant polypeptide having lipase activity, wherein the variant comprises a hybrid of at least one variant polypeptide as in any of claims 1-6, and a second polypeptide having lipase activity, wherein the hybrid has lipase activity. A "hybrid" or "chimeric" or "fusion protein" means that a fragment of the amino acid sequence of a first enzyme is combined with a fragment of the amino acid sequence of a second enzyme to form a hybrid enzyme wherein the hybrid has an enzyme activity.

The hybrid enzymes can be engineered with fragments from amino acid sequences of more than two enzymes. The fragment may be a catalytic domain of a lipase of this invention may be combined with the catalytic domain of a commercially available lipase such as: Lipolase™, Lipex™, Lipolex™ and Lipoclean™ (Novozymes A/S), Lumafast (originally from Genencor) and Lipomax (Gist-Brocades/now DSM), to form a hybrid enzyme and the hybrid has lipase activity.

In one embodiment, at least one domain or fragment of an inventive lipase is combined with at least one domain of a lipase selected from fungal triacylglycerol lipase (EC class 3.1.1.3). Fungal triacylglycerol lipase may be selected from lipases of *Thermomyces lanuginosa*. In one embodiment, at least one *Thermomyces lanuginosa* lipase is selected from triacylglycerol lipase according to amino acids 1-269 of SEQ ID NO: 2 of U.S. Pat. No. 5,869,438.

*Thermomyces lanuginosa* lipase may be selected from variants comprising at least the following amino acid substitutions when compared to amino acids 1-269 of SEQ ID NO: 2 of U.S. Pat. No. 5,869,438: T231R and N233R. Said lipase variants may further comprise one or more of the following amino acid exchanges when compared to amino acids 1-269 of SEQ ID NO: 2 of U.S. Pat. No. 5,869,438: Q4V, V60S, A150G, L227G, P256K. A lipase comprising the T231R and N233R substitution when compared to amino acids 1-269 of SEQ ID NO: 2 of U.S. Pat. No. 5,869,438 may be called Lipex herein.

*Thermomyces lanuginosa* lipase may be selected from variants comprising at least the amino acid substitutions T231R, N233R, Q4V, V60S, A150G, L227G, P256K within the polypeptide sequence of amino acids 1-269 of SEQ ID NO: 2 of U.S. Pat. No. 5,869,438.

*Thermomyces lanuginosa* lipase may be selected from variants comprising the amino acid substitutions T231R and N233R within amino acids 1-269 of SEQ ID NO: 2 of U.S. Pat. No. 5,869,438 and are at least 95%, at least 96%, at least 97%, at least 98%, or at least 99% similar when compared to the full-length polypeptide sequence of amino acids 1-269 of SEQ ID NO: 2 of U.S. Pat. No. 5,869,438.

The variant polypeptides having an amino acid substitution can be a conservative amino acid substitution. A "conservative amino acid substitution" or "related amino acid" means replacement of one amino acid residue in an amino acid sequence with a different amino acid residue having a similar property at the same position compared to the parent amino acid sequence. Some examples of a conservative amino acid substitution include but are not limited to replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue.

A "mature polypeptide" means an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

"Enzymatic activity" means at least one catalytic effect exerted by an enzyme. Enzymatic activity is expressed as units per milligram of enzyme (specific activity) or molecules of substrate transformed per minute per molecule of enzyme (molecular activity). Enzymatic activity can be specified by the enzymes actual function, e.g. proteases exerting proteolytic activity by catalyzing hydrolytic cleavage of peptide bonds, lipases exerting lipolytic activity by hydrolytic cleavage of ester bonds, etc.

Enzymatic activity may change during storage or operational use of the enzyme. The term "enzyme stability" relates to the retention of enzymatic activity as a function of time during storage or operation. The term "storage" herein means to indicate the fact of products or compositions or formulations being stored from the time of being manufactured to the point in time of being used in final application. Retention of enzymatic activity as a function of time during storage in detergent may be called "storage stability" herein.

To determine and quantify changes in catalytic activity of enzymes stored or used under certain conditions over time, the "initial enzymatic activity" is measured under defined conditions at time zero (100%) and at a certain point in time later (x %). By comparison of the values measured, a potential loss of enzymatic activity can be determined in its extent. The extent of enzymatic activity loss determines an enzymes stability or non-stability.

Parameters influencing the enzymatic activity of an enzyme and/or storage stability and/or operational stability are for example pH, temperature, and presence of oxidative substances:

A variant polypeptide is active over a broad pH at any single point within the range from about pH 4.0 to about pH 12.0. The variant polypeptides enzyme may be active over a range of pH 4.0 to pH 11.0, pH 4.0 to pH 10.0, pH 4.0 to pH 9.0, pH 4.0 to pH 8.0, pH 4.0 to pH 7.0, pH 4.0 to pH 6.0, or pH 4.0 to pH 5.0. The variant polypeptides may be active at pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6 pH 8.7, pH 8.8 pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, pH 10.6, pH 10.7, pH 10.8, pH 10.9, pH 11.0, pH 11.1, pH 11.2, pH 11.3, pH 11.4, pH 11.5, pH 11.6, pH 11.7, pH 11.8, pH 11.9, pH 12.0, pH 12.1, pH 12.2, pH 12.3, pH 12.4, and pH 12.5, pH 12.6, pH 12.7, pH 12.8, pH 12.9, and higher.

A "pH stability", refers to the ability of an enzyme to exert enzymatic activity at a specific pH range.

The variant polypeptides are active over a broad temperature, wherein the temperature is any point in the range from about 10° C. to about 60° C. The variant polypeptides may be active at a temperature range from 10° C. to 55° C., 10° C. to 50° C., 10° C. to 45° C., 10° C. to 40° C., 10° C. to 35° C., 10° C. to 30° C., or 10° C. to 25° C. The variant polypeptides may be active at a temperature range from 20° C. to 55° C., 20° C. to 50° C., 20° C. to 45° C., 20° C. to 40° C., 20° C. to 35° C., 20° C. to 30° C., or 20° C. to 25° C. The variant polypeptides may be active at a temperature of at least 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., or higher temperatures.

The terms "thermal stability" and "thermostability" refer to the ability of a protein to exert catalytic activity at a specific temperature, or within a temperature range. Enzymes generally have a finite range of temperatures at which they exert catalytic activity. In addition to enzymes that exert catalytic activity in mid-range temperatures (e.g., room temperature), there are enzymes that are capable of exerting catalytic activity in very high or very low temperatures. Thermostability may be characterized by what is known as the $T_{50}$ value (also called half-life, see above). The $T_{50}$ indicates the temperature at which 50% residual enzymatic activity is still present after thermal inactivation for a certain time when compared with a reference sample which has not undergone thermal treatment.

The terms "thermal tolerance" and "thermotolerance" refer to the ability of a protein to exert catalytic activity after exposure to a particular temperature, such as a very high or very low temperature. A thermotolerant protein may not exert catalytic activity at the exposure temperature, but exerts catalytic activity once returned to a favorable temperature.

The polypeptide variants may be described as an amino acid sequence which is at least n % identical to the amino acid sequence of the respective parent enzyme with "n" being an integer between 10 and 100. The variant polypeptides are at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical when compared to the full length amino acid sequence of the parent enzyme, wherein the enzyme variant has enzymatic activity.

The invention further relates to a polynucleotide encoding the variant polypeptides of the invention. The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length. A "gene" is a DNA segment carrying a certain genetic information.

A "parent" polynucleotide acid sequence is the starting sequence for introduction of mutations to the sequence, resulting in "variants" of said parent polynucleotide sequence. A "variant polynucleotide" refers to a polynucleotide that encodes the same enzyme as the parent polynucleotide does. The variant polynucleotide in this case differs from its parent polynucleotide in its nucleic acid sequence, however the polypeptide encoded remains unchanged.

The polynucleotide of the invention in one aspect has a nucleic acid sequence which is at least 80% identical when compared to the full-length polynucleotide sequence of SEQ ID NO:2. The polynucleotide of the invention may have a nucleic acid sequence which is at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical when compared to the full-length polynucleotide sequence of SEQ ID NO:2.

In one embodiment, the variant polynucleotide which is at least 80% identical when compared to the full-length polynucleotide sequence of SEQ ID NO:2, encodes a polypeptide sequence having lipase activity comprising an amino acid sequence that is at least at least 80% identical to the full length amino acid sequence of SEQ ID NO: 1.

A polynucleotide according to the invention encodes a polypeptide having lipase activity comprising an amino acid sequence that is at least at least 80% identical to the full length amino acid sequence of SEQ ID NO: 1. The polynucleotide of the invention may encode a polypeptide having lipase activity comprising an amino acid sequence that is at least at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the full length amino acid sequence of SEQ ID NO: 1.

In one embodiment, the polynucleotide of the invention encodes a polypeptide having lipase activity comprising an amino acid sequence that is at least at least 80% identical to the full length amino acid sequence of SEQ ID NO:1 which comprises an amino acid residue insertion, deletion, or substitution to the amino acid sequence of SEQ ID NO: 1. The amino acid residue insertion, deletion, or substitution may be at the amino acid residue position number: 23, 33, 82, 83, 84, 85, 160, 199, 254, 255, 256, 258, 263, 264, 265, 268, 308, 311, or any combination thereof. An amino acid substitution may be selected from: Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, and Y311E, or any combination thereof.

The invention relates to a polynucleotide encoding a polypeptide having lipase activity that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the full length amino acid sequence as set forth in SEQ ID NO:1, wherein the amino acid sequence of SEQ ID NO: 1 comprises at least one substitution selected from: Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, and Y311E.

The invention relates to a polynucleotide encoding a polypeptide having lipase activity that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the full length amino acid sequence as set forth in SEQ ID NO:1, wherein the amino acid sequence of SEQ ID NO:1 comprises more than one substitution selected from: Y23A, K33N, S82T, S83D, S83H, S83I, S83N, S83R, S83T, S83Y, S84S, S84N, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I2454V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, and Y311E. The amino acid sequence of SEQ ID NO: 1 may comprise a combination selected from any of the combinations as described in Example 1, Table 1 of this description.

In one embodiment, the polynucleotide encodes a polypeptide of SEQ ID NO: 1 comprising at least a substitution at position 83, wherein the substitution is selected from S83D, S83H, S83I, S83N, S83R, S83T, and S83Y. Preferably, the substitution at position 83 is selected from S83H, S83I, S83N, and S83Y. In one embodiment, the polynucleotide encodes a polypeptide of SEQ ID NO: 1 comprising at least a substitution at position 85, wherein the substitution is selected from I85A, I85C, I85F, I85H, I85L, I85M, I85P, I85S, I85T, I85V, and I85Y. Preferably, the substitution at position 85 is selected from I85L, I85T, and I85V. In one embodiment, the polynucleotide encodes a polypeptide of SEQ ID NO: 1 comprising at least a substitution at position 255, wherein the substitution is selected from I255A, I255L. In one embodiment, the polynucleotide encodes a polypeptide of SEQ ID NO: 1 comprising at least a substitution at position 264, wherein the substitution is selected from T264A, T264D, T264G, T264I, T264L, T264N, T264S. Preferably, the substitution at position 264 is selected from T264A, T264D, T264N, and T264S. In one embodiment, the polynucleotide encodes a polypeptide of SEQ ID NO: 1 comprising at least a substitution at position 265, wherein the substitution is selected from D265A, D265G, D265K, D265L, D265N, D265S, and D265T. Preferably, the substitution at position 265 is selected from D265A, D265G, D265S, and D265T.

In one embodiment, the polynucleotide encodes a polypeptide of SEQ ID NO: 1 comprising at least a substitution at position 83 and a substitution at position 85, wherein the substitution at position 83 is selected from S83D, S83H, S83I, S83N, S83R, S83T, and S83Y, and the substitution at position 85 is selected from I85A, I85C, I85F, I85H, I85L, I85M, I85P, I85S, I85T, I85V, and I85Y. In embodiments of the invention, the polynucleotide encodes for a polypeptide of SEQ ID NO: 1, wherein at least the following combinations of substitutions in the encoded polypeptide occur: the substitution at position 83 is selected from S83H, and S83I, and the substitution at position 85 is selected from I85L, I85P, I85T, and I85V; the substitution at position 83 is S83H, and the substitution at position 85 is selected from I85L, I85P, and I85T; the substitution at position 83 is S83I, and the substitution at position 85 is I85V.

In one embodiment, the polynucleotide encodes a polypeptide of SEQ ID NO: 1 comprising at least a substitution at position 83 and a substitution at position 255, wherein the substitution at position 83 is selected from S83D, S83H, S83I, S83N, S83R, S83T, and S83Y, and the substitution at position 255 is selected from I255A, and I255L. In embodiments of the invention, the polynucleotide encodes for a polypeptide of SEQ ID NO: 1, wherein at least the following combinations of substitutions in the encoded polypeptide occur: the substitution at position 83 is selected from S83H, S83N, and S83Y, and the substitution at position 264 is selected from T264A, T264D, T264N, and T264S; the substitution at position 83 is selected from S83H, S83N, S83T and S83Y, and the substitution at position 255 is I255A.

In one embodiment, the polynucleotide encodes a polypeptide of SEQ ID NO: 1 comprising at least a substitution at position 83 and a substitution at position 264, wherein the substitution at position 83 is selected from S83D, S83H, S83I, S83N, S83R, S83T, and S83Y, and the substitution at position 264 is selected from T264A, T264D, T264G, T264I, T264L, T264N, and T264S. In embodiments of the invention, the polynucleotide encodes for a polypeptide of SEQ ID NO: 1, wherein at least the following combinations of substitutions in the encoded polypeptide occur: the substitution at position 83 is selected from S83H, S83N, and S83Y, and the substitution at position 264 is selected from T264A, T264D, T264N, and T264S; the substitution at position 83 is S83H, and the substitution at position 264 is selected from T264A, T264N, and T264S; the substitution at position 83 is S83N, and the substitution at position 264 is selected from T264A, T264D, T264N, and T264S; the substitution at position 83 is S83Y, and the substitution at position 264 is selected from T264A, and T264S.

In one embodiment, the polynucleotide encodes a polypeptide of SEQ ID NO: 1 comprising at least a substitution at position 83 and a substitution at position 265, wherein the substitution at position 83 is selected from S83D, S83H, S83I, S83N, S83R, S83T, and S83Y, and the substitution at position 265 is selected from D265A, D265G, D265K, D265L, D265N, D265S, and D265T. In embodiments of the invention, the polynucleotide encodes for a polypeptide of SEQ ID NO: 1, wherein at least the following combinations of substitutions in the encoded polypeptide occur: the substitution at position 83 is selected from S83H, S83I, S83N, S83T and S83Y, and the substitution at position 265 is selected from D265A, D265G, D265S, and D265T; the substitution at position 83 is S83H, and the substitution at position 265 is selected from D265A, D265G, D265S, and D265T; the substitution at position 83 is S83I, and the substitution at position 265 is selected from D265G, and D265S; the substitution at position 83 is S83N, and the substitution at position 265 is selected from D265A, D265G, D265S, and D265T; the substitution at position 83 is S83T, and the substitution at position 265 is selected from D265A, D265S, and D265T; the substitution at position 83 is S83Y, and the substitution at position 265 is D265T.

In one embodiment, the polynucleotide encodes a polypeptide of SEQ ID NO: 1 comprising at least a substitution at position 85 and a substitution at position 265, wherein the substitution at position 85 is selected from I85A, I85C, I85F, I85H, I85L, I85M, I85P, I85S, I85T, I85V, and I85Y, and the substitution at position 265 is selected from D265A, D265G, D265K, D265L, D265N, D265S, and D265T. In embodiments of the invention, the polynucleotide encodes for a polypeptide of SEQ ID NO: 1, wherein at least the following combinations of substitutions in the encoded polypeptide occur: the substitution at position 85 is selected from I85A, I85H, I85L, I85P, I85S, I85T, and I85V, and the substitution at position 265 is selected from D265A, D265G, D265S, and D265T; the substitution at position 85 is I85A, and the substitution at position 265 is D265T; the substitution at position 85 is I85H, and the substitution at position 265 is D265A; the substitution at position 85 is I85L, and the substitution at position 265 is selected from D265A, D265G, D265S, and D265T; the substitution at position 85 is I85P, and the substitution at position 265 is D265A; the substitution at position 85 is I85S, and the substitution at position 265 is D265S; the substitution at position 85 is I85T, and the substitution at position 265 is selected from D265G, D265S, and D265T; the substitution at position 85 is I85V, and the substitution at position 265 is selected from D265A, D265G, D265S, and D265T.

In one embodiment, the polynucleotide encodes a polypeptide of SEQ ID NO: 1 comprising at least a substitution at position 85 and a substitution at position 255, wherein the substitution at position 85 is selected from I85A, I85C, I85F, I85H, I85L, I85M, I85P, I85S, I85T, I85V, and I85Y, and wherein the substitution at position 255 is selected from I255A, and I255L. In embodiments of the invention, the polynucleotide encodes for a polypeptide of SEQ ID NO: 1, wherein at least the following combinations of substitutions in the encoded polypeptide occur: the substitution at position 85 is a I85H substitution, and the substitution at position 255 is a I255A substitution; the substitution at position 85 is a I85L substitution, and the substitution at position 255 is a I255A substitution; the substitution at position 85 is a I85S substitution, and the substitution at position 255 is a I255A substitution; the substitution at position 85 is a I85V substitution, and the substitution at position 255 is a I255A substitution.

In one embodiment, the polynucleotide encodes a polypeptide of SEQ ID NO: 1 comprising at least a substitution at position 83, a substitution at position 85, and a substitution at position 255, wherein the substitution at position 83 is selected from S83D, S83H, S83I, S83N, S83R, S83T, and S83Y, wherein the substitution at position 85 is selected from I85A, I85C, I85F, I85H, I85L, I85M, I85P, I85S, I85T, I85V, and I85Y, and wherein the substitution at position 255 is selected from I255A, and I255L. In embodiments of the invention, the polynucleotide encodes for a polypeptide of SEQ ID NO: 1, wherein at least the following combinations of substitutions in the encoded polypeptide occur: the substitution at position 83 is a S83H substitution, the substitution at position 85 is selected from I85A, I85L, I85P, I85S, I85T, and I85V, and the substitution at position 255 is a I255A substitution; the substitution at position 83 is a S83N substitution, the substitution at position 85 is selected from I85L, and I85V, and the substitution at position 255 is a I255A substitution; the substitution at position 83 is a S83T substitution, the substitution at position 85 is selected from I85H, and I85V, and the substitution at position 255 is a I255A substitution; the substitution at position 83 is a S83Y substitution, the substitution at position 85 is selected from I85A, and I85V, and the substitution at position 255 is a I255A substitution.

In one embodiment, the polynucleotide encodes a polypeptide of SEQ ID NO: 1 comprising at least a substitution at position 85 and a substitution at position 264, wherein the substitution at position 85 is selected from I85A, I85C, I85F, I85H, I85L, I85M, I85P, I85S, I85T, I85V, and I85Y, and wherein the substitution at position 264 is selected from T264A, T264D, T264N, and T264S. In embodiments of the invention, the polynucleotide encodes for a polypeptide of SEQ ID NO: 1, wherein at least the following combinations of substitutions in the encoded polypeptide occur: the substitution at position 85 is a I85A substitution, and the substitution at position 264 is a T264A substitution; the substitution at position 85 is a I85L substitution, and the substitution at position 264 is a T264S substitution; the substitution at position 85 is a I85S substitution, and the substitution at position 264 is a T264A substitution; the substitution at position 85 is a I85T substitution, and the substitution at position 264 is a T264A substitution; the substitution at position 85 is a I85V substitution, and the substitution at position 264 is selected from T264A, T264D, T264N, and T264S.

In one embodiment, the polynucleotide encodes a polypeptide of SEQ ID NO: 1 comprising at least a substitution at position 255 and a substitution at position 264, wherein the substitution at position 255 is selected from I255A, and I255L, and wherein the substitution at position 264 is selected from T264A, T264D, T264N, and T264S. In embodiments of the invention, the polynucleotide encodes for a polypeptide of SEQ ID NO: 1, wherein at least the following combinations of substitutions in the encoded polypeptide occur: the substitution at position 255 is a I255A substitution, and the substitution at position 264 is selected from T264A, T264D, T264N, and T264S.

In one embodiment, the polynucleotide encodes a polypeptide of SEQ ID NO: 1 comprising at least a substitution at position 255 and a substitution at position 265, wherein the substitution at position 255 is selected from I255A, and I255L, and wherein the substitution at position 265 is selected from T264A, T264D, T264N, and T264S. In embodiments of the invention, the polynucleotide encodes for a polypeptide of SEQ ID NO: 1, wherein at least the following combinations of substitutions in the encoded polypeptide occur: the substitution at position 255 is a I255A substitution, and the substitution at position 265 is selected from D265A, D265G, D265K, D265L, D265N, D265S, and D265T; the substitution at position 255 is a I255A substitution, and the substitution at position 265 is selected from D265A, D265G, D265S, and D265T; the substitution at position 255 is a I255A substitution, and the substitution at position 265 is a D265S substitution.

In one embodiment, the polynucleotide encodes a polypeptide of SEQ ID NO: 1 comprising at least a substitution at position 264 and a substitution at position 265, wherein the substitution at position 264 is selected from T264A, T264D, T264N, and T264S, and wherein the substitution at position 265 is selected from D265A, D265G, D265K, D265L, D265N, D265S, and D265T. In embodiments of the invention, the polynucleotide encodes for a polypeptide of SEQ ID NO: 1, wherein at least the following combinations of substitutions in the encoded polypeptide occur: the substitution at position 264 is a T264A substitution, and the substitution at position 265 is selected from D265A, D265G, D265S, and D265T; the substitution at position 264 is a T264D substitution, and the substitution at position 265 is selected from D265A, and D265T; the substitution at position 264 is a T264N substitution, and the substitution at position 265 is selected from D265A, and D265T; the substitution at position 264 is a T264S substitution, and the substitution at position 265 is selected from D265A, D265G, D265S, and D265T.

In one embodiment, the polynucleotide encodes a polypeptide of SEQ ID NO: 1 comprising at least a substitution at position 85 and a substitution at position 265, wherein the substitution at position 85 is selected from I85A, I85C, I85F, I85H, I85L, I85M, I85P, I85S, I85T, I85V, and I85Y, and the substitution at position 265 is selected from D265A, D265G, D265K, D265L, D265N, D265S, and D265T, further comprises a substitution at position 264, wherein the substitution is selected from T264A, T264D, T264N, and T264S. In embodiments of the invention, the polynucleotide encodes for a polypeptide of SEQ ID NO: 1, wherein at least the following combinations of substitutions in the encoded polypeptide occur: the substitution at position 85 is a I85A substitution, the substitution at position 264 is a T264A substitution, and the substitution at position 265 is a D265T substitution; the substitution at position 85 is a I85L substitution, the substitution at position 264 is a T264S substitution, and the substitution at position 265 is selected from D265A, D265G, D265S, and D265T; the substitution at position 85 is a I85S substitution, the substitution at position 264 is a T264A substitution, and the substitution at position 265 is a D265T substitution; the substitution at position 85 is a I85T substitution, the substitution at position 264 is a T264A substitution, and the substitution at position 265 is selected from D265G, D265S, and D265T; the substitution at position 85 is a I85V substitution, the substitution at position 264 is selected from T264A, T264D, T264N, and T264S, and the substitution at position 265 is selected from D265A, D265G, D265S, and D265T.

In one embodiment, the polynucleotide encodes a polypeptide of SEQ ID NO: 1 comprising at least a substitution at position 85 and a substitution at position 265, wherein the substitution at position 85 is selected from I85A, I85C, I85F, I85H, I85L, I85M, I85P, I85S, I85T, I85V, and I85Y, and the substitution at position 265 is selected from D265A, D265G, D265K, D265L, D265N, D265S, and D265T, further comprises a substitution at position 255, wherein the substitution is selected from I255A, and I255L. In embodiments of the invention, the polynucleotide encodes for a polypeptide of SEQ ID NO: 1, wherein at least the following combinations of substitutions in the encoded polypeptide occur: the substitution at position 85 is a I85H substitution, the substitution at position 255 is a I255A substitution, and the substitution at position 265 is a D265A substitution; the substitution at position 85 is a I85L substitution, the substitution at position 255 is a I255A substitution, and the substitution at position 265 is selected from D265A, D265G, D265S, and D265T; the substitution at position 85 is a I85S substitution, the substitution at position 255 is a I255A substitution, and the substitution at position 265 is a D265T substitution; the substitution at position 85 is a I85V substitution, the substitution at position 255 is a I255A substitution, and the substitution at position 265 is selected from D265A, D265G, D265S, and D265T.

In one embodiment, the polynucleotide encodes a polypeptide of SEQ ID NO: 1 comprising at least a substitution at position 85, a substitution at position 265, a substitution at position 255, and a substitution at position 264, wherein the substitution at position 85 is selected from I85A, I85C, I85F, I85H, I85L, I85M, I85P, I85S, I85T, I85V, and I85Y, wherein the substitution at position 265 is selected from D265A, D265G, D265K, D265L, D265N, D265S, and D265T, wherein the substitution at position 255, is selected from I255A and I255L, and wherein the substitution at position 264 is selected from T264A, T264D, T264N, and T264S. In embodiments of the invention, the polynucleotide encodes for a polypeptide of SEQ ID NO: 1, wherein at least the following combinations of substitutions in the encoded polypeptide occur: the substitution at position 85 is a I85L substitution, the substitution at position 255 is a I255A substitution, the substitution at position 264 is a T264S substitution, and the substitution at position 265 is selected from D265A, D265G, D265S, and D265T; the substitution at position 85 is a I85S substitution, the substitution at position 255 is a I255A substitution, the substitution at position 264 is a T264A substitution, and the substitution at position 265 is a D265T substitution; the substitution at position 85 is a I85V substitution, the substitution at position 255 is a I255A substitution, the substitution at position 264 is selected from T264A, T264G, T264S, and T264T, and the substitution at position 265 is selected from D265A, D265G, D265S, and D265T.

In one embodiment, the polynucleotide encodes a polypeptide of SEQ ID NO: 1 comprising at least a substitution at position 83, a substitution at position 85, and a substitution at position 264 and/or position 265, wherein the substitution at position 83 is selected from S83D, S83H, S83I, S83N, S83R, S83T, and S83Y, wherein the substitution at position 85 is selected from I85A, I85C, I85F, I85H, I85L, I85M, I85P, I85S, I85T, I85V, and I85Y, wherein the substitution at position 264 is selected from T264A, T264D, T264N, and T264S, and wherein the substitution at position 265 is selected from D265A, D265G, D265K, D265L, D265N, D265S, and D265T. In embodiments of the invention, the polynucleotide encodes for a polypeptide of SEQ ID NO: 1, wherein at least the following combinations of substitutions in the encoded polypeptide occur: the substitution at position 83 is a S83H substitution, the substitution at position 85 is selected from I85A, I85L, I85P, I85S, I85T, and I85V, the substitution at position 264 is selected from T264A, T264N, and T264S, and the substitution at position 265 is selected from D265A, D265G, D265S, and D265T; the substitution at position 83 is a S83H substitution, the substitution at position 85 is a I85L substitution, and the substitution at position 265 is a D265G substitution; the substitution at position 83 is a S83H substitution, the substitution at position 85 is a I85L substitution, the substitution at position 264 is a T264A substitution, and the substitution at position 265 is a D265T substitution; the substitution at position 83 is a S83N substitution, the substitution at position 85 is selected from I85L, and I85V, the substitution at position 264 is selected from T264A, T264D, T264N, and T264S, and the substitution at position 265 is selected from D265A, D265G, D265S, and D265T; the substitution at position 83 is a S83Y substitution, the substitution at position 85 is selected from I85A, and I85V, the substitution at position 264 is selected from T264A, and T264S, and a D265T substitution.

In one embodiment, the polynucleotide encodes a polypeptide of SEQ ID NO: 1 comprising at least a substitution at position 83, a substitution at position 85, and a substitution at position 255, may further comprise a substitution at position 264 and/or position 265, wherein the substitution at position 83 is selected from S83D, S83H, S83I, S83N, S83R, S83T, and S83Y, wherein the substitution at position 85 is selected from I85A, I85C, I85F, I85H, I85L, I85M, I85P, I85S, I85T, I85V, and I85Y, wherein the substitution at position 255 is selected from I255A, and I255L, wherein the substitution at position 264 is selected from T264A, T264D, T264N, and T264S, and wherein the substitution at position 265 is selected from D265A, D265G, D265K, D265L, D265N, D265S, and D265T. In embodiments of the invention, the polynucleotide encodes for a polypeptide of SEQ ID NO: 1, wherein at least the following combinations of substitutions in the encoded polypeptide occur: the substitution at position 83 is a S83H substitution, the substitution at position 85 is selected from I85A, I85L, I85P, I85S, I85T, and I85V, the substitution at position 255 is a I255A substitution, the substitution at position 264 is selected from T264A, T264N, and T264S, and the substitution at position 265 is selected from D265A, D265G, D265S, and D265T; the substitution at position 83 is a S83N substitution, the substitution at position 85 is selected from I85L, and I85V, a I255A substitution, the substitution at position 264 is selected from T264A, T264D, T264N, and T264S, and the substitution at position 265 is selected from D265A, D265G, D265S, and D265T; the substitution at position 83 is a S83Y substitution, the substitution at position 85 is selected from I85A, and I85V, the substitution at position 255 is a I255A substitution, the substitution at position 264 is selected from T264A, and T264S, and the substitution at position 265 is a D265T substitution.

In one embodiment, the polynucleotide encodes a polypeptide of SEQ ID NO: 1, wherein besides the combinations of substitutions disclosed above, at least one of the following additional substitutions are encoded: K160N, I254L, I256D, D263R, T268G.

The polynucleotide of the invention in one aspect encodes a variant polypeptide having lipase activity, wherein the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the full length amino acid sequence as set forth in SEQ ID NO: 1, wherein the variant polypeptide exerts increased enzymatic activity, pH-stability, stability against proteolytic degradation, or any combination thereof when compared to the lipase of SEQ ID NO: 1.

The invention relates to a polynucleotide encoding a polypeptide having lipase activity, wherein the polypeptide is a fragment of the inventive full length amino acid sequence as disclosed above.

The invention relates to a polynucleotide encoding a polypeptide having lipase activity, wherein the polypeptide is a hybrid of at least one inventive polypeptide and at least one polypeptide different from the inventive polypeptide. In one embodiment, the polynucleotide encodes a polypeptide having lipase activity, wherein the polypeptide is a hybrid of at least one inventive polypeptide and at least one lipase different from the inventive polypeptide.

Variant polynucleotide and variant polypeptide sequences may be defined by their "sequence identity" when compared to a parent sequence. Sequence identity usually is provided as "% sequence identity" or "% identity". For calculation of sequence identities, in a first step a sequence alignment has to be produced. According to this invention, a pairwise global alignment has to be produced, meaning that two sequences have to be aligned over their complete length, which is usually produced by using a mathematical approach, called alignment algorithm.

According to the invention, the alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (polynucleotides: gap open=10.0, gap extend=0.5 and matrix=EDNAFULL; polypeptides: gap open=10.0, gap extend=0.5 and matrix=EBLOSUM62).

After aligning two sequences, in a second step, an identity value is determined from the alignment produced.

In one embodiment, the %-identity is calculated by dividing the number of identical residues by the length of the alignment region which is showing the respective sequence of this invention over its complete length multiplied with 100: %-identity=(identical residues/length of the alignment region which is showing the respective sequence of this invention over its complete length)*100.

In a preferred embodiment, the %-identity is calculated by dividing the number of identical residues by the length of the alignment region which is showing the two aligned sequences over their complete length multiplied with 100: %-identity=(identical residues/length of the alignment region which is showing the two aligned sequences over their complete length)*100.

Variant polypeptides may be defined by their "sequence similarity" when compared to a parent sequence. Sequence similarity usually is provided as "% sequence similarity" or "%-similarity". % sequence similarity takes into account that defined sets of amino acids share similar properties, e.g by their size, by their hydrophobicity, by their charge, or by other characteristics. Herein, the exchange of one amino acid with a similar amino acid may be called "conservative mutation". Similar amino acids according to the invention are defined as follows:

Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q
Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

For calculation of sequence similarity is, in a first step a sequence alignment has to be produced as described above.

In one embodiment, the %-similarity is calculated by dividing the number of identical residues plus the number of similar residues by the length of the alignment region which is showing the respective sequence of this invention over its complete length multiplied with 100: %-similarity=[(identical residues+similar residues)/length of the alignment region which is showing the respective sequence of this invention over its complete length]*100.

In a preferred embodiment, the %-similarity is calculated by dividing the number of identical residues plus the number of similar residues by the length of the alignment region which is showing the two aligned sequences over their complete length multiplied with 100: %-similarity=[(identical residues+similar residues)/length of the alignment region which is showing the two aligned sequences over their complete length]*100.

A Polynucleotide encoding a polypeptide may be "expressed". "Expression" usually describes the process undergone by a polynucleotide sequence encoding a polypeptide to actually produce said polypeptide in an organism.

Industrial production of enzymes usually is done by using expression systems. "Wild-type cells" herein means cells prior to a certain modification. The term "recombinant cell" (also called "genetically modified cell" herein) refers to a cell which has been genetically altered, modified or engineered such that it exhibits an altered, modified or different genotype as compared to the wild-type cell which it was derived from. The "recombinant cell" may comprise an exogenous polynucleotide encoding a certain protein or enzyme and therefore may express said protein or enzyme.

"Expression system" may mean a host microorganism, expression hosts, host cell, production organism, or production strain and each of these terms can be used interchangeably. Examples of expression systems include but are not limited to: *Aspergillus niger, Aspergillus oryzae, Hansenula polymorpha, Thermomyces lanuginosus, Fusarium oxysporum, Fusarium heterosporum, Escherichia coli, Bacillus*, preferably *Bacillus subtilis*, or *Bacillus licheniformis, Pseudomonas*, preferably *Pseudomonas fluorescens, Pichia pastoris* (also known as *Komagataella phaffii*), *Myceliopthora thermophile* (C1), *Schizosaccharomyces pombe, Trichoderma*, preferably *Trichoderma reesei* and *Saccharomyces*, preferably *Saccharomyces cerevisiae*. The variant polypeptides are produced using the expression system listed above.

The term "non-naturally occurring" refers to a (poly) nucleotide, amino acid, (poly)peptide, enzyme, protein, cell, organism, or other material that is not present in its original naturally occurring environment or source.

The term "heterologous" (or exogenous or foreign or recombinant) in the context of polynucleotides and polypeptides is defined herein as:

(a) not native to the host cell;

(b) native to the host cell; however, structural modifications, e.g., deletions, substitutions, and/or insertions, are included as a result of manipulation of the DNA of the host cell by recombinant DNA techniques to alter the native sequence; or (c) native to the host cell but expression is quantitatively altered or expression is directed from a genomic location different from the native host cell as a result of manipulation of the DNA of the host cell by recombinant DNA techniques, e.g., a stronger promoter.

With respect to two or more polynucleotide sequences or two or more amino acid sequences, the term "heterologous" is used to characterize that the two or more polynucleotide sequences or two or more amino acid sequences do not occur naturally in the specific combination with each other.

"Genetic Construct" or "expression cassette" as used herein, is a DNA molecule composed of at least one sequence of interest to be expressed, operably linked to one or more control sequences (at least to a promoter) as described herein. Typically, the expression cassette comprises three elements: a promoter sequence, an open reading frame, and a 3' untranslated region that, in eukaryotes, usually contains a polyadenylation site. Additional regulatory elements may include transcriptional as well as translational enhancers. An intron sequence may also be added to the 5' untranslated region (UTR) or in the coding sequence to increase the amount of the mature message that accumulates in the cytosol. The expression cassette may be part of a vector or may be integrated into the genome of a host cell and replicated together with the genome of its host cell. The expression cassette usually is capable of increasing or decreasing expression.

The term "vector" as used herein comprises any kind of construct suitable to carry foreign polynucleotide sequences for transfer to another cell, or for stable or transient expression within a given cell. The term "vector" as used herein encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence which may be referred to herein as "gene of interest". The gene of interest may comprise introns and exons, depending on the kind of origin or destination of host cell.

A vector as used herein may provide segments for transcription and translation of a foreign polynucleotide upon transformation into a host cell or host cell organelles. Such additional segments may include regulatory nucleotide sequences, one or more origins of replication that is required for its maintenance and/or replication in a specific cell type, one or more selectable markers, a polyadenylation signal, a suitable site for the insertion of foreign coding sequences such as a multiple cloning site etc. One example is when a vector is required to be maintained in a bacterial cell as an episomal genetic element (e.g. plasmid or cosmid molecule). Non-limiting examples of suitable origins of replication include the f1-ori and colE1.

A vector may replicate without integrating into the genome of a host cell, e.g. as a plasmid in a bacterial host cell, or it may integrate part or all of its DNA into the genome of the host cell and thus lead to replication and expression of its DNA.

Foreign nucleic acid may be introduced into a vector by means of cloning. Cloning may mean that by cleavage of the vector (e.g. within the multiple cloning site) and the foreign polynucleotide by suitable means and methods (e.g., restriction enzymes), fitting structures within the individual nucleic acids may be created that enable the controlled fusion of said foreign nucleic acid and the vector.

Once introduced into the vector, the foreign nucleic acid comprising a coding sequence may be suitable to be introduced (transformed, transduced, transfected, etc.) into a host cell or host cell organelles. A cloning vector may be chosen suitable for expression of the foreign polynucleotide sequence in the host cell or host cell organelles.

The term "introduction" or "transformation" as referred to herein encompasses the transfer of an exogenous polynucleotide into a host cell, irrespective of the method used for transfer. That is, the term "transformation" as used herein is independent from vector, shuttle system, or host cell, and it not only relates to the polynucleotide transfer method of transformation as known in the art (cf., for example, Sambrook, J. et al. (1989) Molecular Cloning: A Laboratory Manual, 2nd Ed., Cold Spring Harbor Laboratory Press, Cold Spring Harbor, N.Y.), but it encompasses any further kind polynucleotide transfer methods such as, but not limited to, transduction or transfection. Plant tissue capable of subsequent clonal propagation, whether by organogenesis or embryogenesis, may be transformed with a genetic construct and a whole plant regenerated therefrom. The particular tissue chosen will vary depending on the clonal propagation systems available for, and best suited to, the particular species being transformed.

In one embodiment of the invention, a vector is used for transformation of a host cell.

The polynucleotide may be transiently or stably introduced into a host cell and may be maintained non-integrated, for example, as a plasmid. "Stable transformation" may mean that the transformed cell or cell organelle passes the nucleic acid comprising the foreign coding sequence on to the next generations of the cell or cell organelles. Usually stable transformation is due to integration of nucleic acid comprising a foreign coding sequence into the chromosomes or as an episome (separate piece of nuclear DNA).

"Transient transformation" may mean that the cell or cell organelle once transformed expresses the foreign nucleic acid sequence for a certain time—mostly within one generation. Usually transient transformation is due to nucleic acid comprising a foreign nucleic acid sequence is not integrated into the chromosomes or as an episome.

Alternatively, it may be integrated into the host genome. The resulting transformed plant cell may then be used to regenerate a transformed plant in a manner known to persons skilled in the art.

Recombinant cells may exhibit "increased" or "decreased" expression when compared to the respective wild-type cell.

The term "increased expression", "enhanced expression" or "overexpression" as used herein means any form of expression that is additional to the original wild-type expression level (which can be absence of expression or immeasurable expression as well). Reference herein to "increased expression", "enhanced expression" or "overexpression" is taken to mean an increase in gene expression and/or, as far as referring to polypeptides, increased polypeptide levels and/or increased polypeptide activity, relative to control organisms. The increase in expression may be in increasing order of preference at least 5%, at least 10%, at least 20%, at least 30%, at least 40%, at least 50%, at least 60%, at least 70%, at least 80%, at least 85%, at least 90%, or 100% or even more compared to that of control organisms.

Methods for increasing expression of genes or gene products, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to increase expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO 93/22443), or isolated promoters may be introduced into an organism in the proper orientation and distance from a gene of the present invention so as to control the expression of the gene.

An intron sequence may also be added to the 5' untranslated region (UTR) or the coding sequence of the partial coding sequence to increase the amount of the mature message that accumulates in the cytosol. Inclusion of a spliceable intron in the transcription unit in expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit.

To obtain increased expression or overexpression of a polypeptide most commonly the nucleic acid encoding this polypeptide is overexpressed in sense orientation with a polyadenylation signal. Introns or other enhancing elements may be used in addition to a promoter suitable for driving expression with the intended expression pattern.

Enzymes are generally produced commercially by using recombinant cells which express the desired enzyme by cultivation of the same under conditions suitable for expression of the desired enzyme.

Cultivation normally takes place in a suitable nutrient medium allowing the recombinant cells to grow (this process may be called fermentation) and express the desired protein. At the end of fermentation, fermentation broth is collected and may be further processed, wherein the fermentation broth comprises a liquid fraction and a solid fraction.

The enzyme of interest may be further purified from the fermentation broth. The resulting product may be called "isolated polypeptide product" herein or "isolated lipase product", wherein the polypeptide or lipase in this context means the polypeptide or liase of the invention. The term "purification" or "purifying" refers to a process in which at least one component, e.g., a protein of interest, is separated from at least another component, e.g., a particulate matter of a fermentation broth, and transferred into a different compartment or phase, wherein the different compartments or phases do not necessarily need to be separated by a physical barrier. Examples of such different compartments are two compartments separated by a filtration membrane or cloth, i.e., filtrate and retentate; examples of such different phases are pellet and supernatant or cake and filtrate, respectively.

The enzyme of interest may be secreted (into the liquid fraction of the fermentation broth) or may not be secreted from the host cells (and therefore is comprised in the cells of the fermentation broth). Depending on this, the desired protein or enzyme may be recovered from the liquid fraction of the fermentation broth or from cell lysates. Recovery of the desired enzyme uses methods known to those skilled in the art. Suitable methods for recovery of proteins or enzymes from fermentation broth include but are not limited to collection, centrifugation, filtration, extraction, and precipitation. If the enzyme of interest precipitates or crystallizes in the fermentation broth or binds at least in part to the particulate matter of the fermentation broth additional treatment steps might be needed to release the enzyme from the biomass or solubilize enzyme crystals and precipitates. U.S. Pat. No. 6,316,240B1 describes a method for recovering an enzyme, which precipitates and/or crystallizes during fermentation, from the fermentation broth. In case the desired enzyme is comprised in the cells of the fermentation broth release of the enzyme from the cells might be needed. Release from the cells can be achieved for instance, but not being limited thereto, by cell lysis with techniques well known to the skilled person.

"Pure polypeptide having lipase activity" means that the polypeptide of the invention is comprised in the isolated polypeptide product in amounts of at least about 80% by weight, relative to the total weight of the isolated polypeptide product. "Pure polypeptide having lipase activity" may mean that the polypeptide of the invention is comprised in the isolated polypeptide product in amounts of at least about 81% by weight, at least about 82% by weight, at least about 83% by weight, at least about 84% by weight, at least about 85% by weight, at least about 86% by weight, at least about 87% by weight, at least about 88% by weight, at least about 89% by weight, at least about 90% by weight, at least about 91% by weight, at least about 92% by weight, at least about 93% by weight, at least about 94% by weight, at least about 95% by weight, at least about 96% by weight, at least about 97% by weight, at least about 98% by weight, at least about 99% by weight, or 100% by weight, all relative to the total weight of the polypeptide product. Preferably "purified"

means that the material is in a 100% pure state. "Pure polypeptide having lipase activity" may mean that the amount of compounds different from the polypeptide of the invention comprised in the isolated polypeptide product is less than 20% by weight, less than 19% by weight, less than 18% by weight, less than 17% by weight, less than 16% by weight, less than 15% by weight, less than 14% by weight, less than 13% by weight, less than 12% by weight, less than 11% by weight, less than 10% by weight, less than 9% by weight, less than 8% by weight, less than 7% by weight, less than 6% by weight, less than 5% by weight, less than 4% by weight, less than 3% by weight, less than 2% by weight, or less than 1% by weight, all relative to the total weight of the polypeptide product. Compounds different from the polypeptide of the invention comprised in the isolated polypeptide product may be e.g. components such as salts originating from the fermentation medium, cell debris originating from the production host cells, metabolites produced by the production host cells during fermentation.

The isolated polypeptide product may be further processed to form an "enzyme formulation".

"Liquid" is related to the physical appearance at 20° C. and 101.3 kPa.

"Enzyme formulation" means any non-complex formulation comprising a small number of ingredients, wherein the ingredients serve the purpose of stabilizing the enzymes comprised in the enzyme formulation and/or the stabilization of the enzyme formulation itself. The term "enzyme stability" relates to the retention of enzymatic activity as a function of time during storage or operation. The term "enzyme formulation stability" relates to the maintenance of physical appearance of the enzyme formulation during storage or operation as well as the avoidance of microbial contamination during storage or operation.

An "enzyme formulation" is a composition which is meant to be formulated into a complex formulation which itself may be determined for final use. An "enzyme formulation" according to the invention is not a complex formulation comprising several components, wherein the components are formulated into the complex formulation to exert each individually a specific action in a final application. A complex formulation may be without being limited thereto a detergent formulation, wherein individual detergent components are formulated in amounts effective in the washing performance of the detergent formulation.

In one aspect of the invention, at least one amylase variant of the invention is comprised in an enzyme formulation.

The enzyme formulation can be either solid or liquid. Enzyme formulations can be obtained by using techniques known in the art. For instance, without being limited thereto, solid enzyme formulations can be obtained by extrusion or granulation. Suitable extrusion and granulation techniques are known in the art and are described for instance in WO9419444A1 and WO9743482A1.

Liquid enzyme formulations may comprise amounts of enzyme in the range of 0.1% to 40% by weight, or 0.5% to 30% by weight, or 1% to 25% by weight, or 3% to 10% by weight, all relative to the total weight of the enzyme concentrate.

The liquid enzyme concentrate may comprise more than one type of enzyme. In one embodiment, the enzyme formulation comprises one or more lipases according to the present invention. In one embodiment, the enzyme formulation comprises one or more lipases according to the present invention and at least one additional enzyme selected from the group of a lipase different from the inventive lipases, a protease, a cellulase, an amylase, a laccase, a pectinase, a nuclease, and any combination thereof. Aqueous enzyme formulations of the invention may comprise water in amounts of more than about 50% by weight, more than about 60% by weight, more than about 70% by weight, or more than about 80% by weight, all relative to the total weight of the enzyme formulation.

In one embodiment, the enzyme formulation comprises in addition to at least one polypeptide of the invention one or more compounds selected from the group consisting of other enzymes, preservatives and stabilizers.

In one embodiment, a liquid enzyme formulation comprises at least one polypeptide variant of the invention and at least one preservative. Non-limiting examples of suitable preservatives include (quaternary) ammonium compounds, isothiazolinones, organic acids, and formaldehyde releasing agents. Non-limiting examples of suitable (quaternary) ammonium compounds include benzalkonium chlorides, polyhexamethylene biguanide (PHMB), Didecyldimethyl ammonium chloride (DDAC), and N-(3-aminopropyl)-N-dodecylpropane-1,3-diamine (Diamine). Non-limiting examples of suitable isothiazolinones include 1,2-benzisothiazolin-3-one (BIT), 2-methyl-2H-isothiazol-3-one (MIT), 5-chloro-2-methyl-2H-isothiazol-3-one (CIT), 2-octyl-2H-isothiazol-3-one (OIT), and 2-butyl-benzo[d]isothiazol-3-one (BBIT). Non-limiting examples of suitable organic acids include benzoic acid, sorbic acid, L-(+)-lactic acid, formic acid, and salicylic acid. Non-limiting examples of suitable formaldehyde releasing agent include N,N'-methylenebismorpholine (MBM), 2,2',2"-(hexahydro-1,3,5-triazine-1,3,5-triyl)triethanol (HHT), (ethylenedioxy)dimethanol, .alpha.,.alpha.',.alpha."-trimethyl-1,3,5-triazine-1,3,5 (2H,4H,6H)-triethanol (HPT), 3,3'-methylenebis[5-methyloxazolidine] (MBO), and cis-1-(3-chloroallyl)-3,5,7-triaza-1-azoniaadamantane chloride (CTAC).

Further useful preservatives include iodopropynyl butylcarbamate (IPBC), halogen releasing compounds such as dichloro-dimethyl-hydantoine (DCDMH), bromo-chloro-dimethyl-hydantoine (BCDMH), and dibromo-dimethyl-hydantoine (DBDMH); bromo-nitro compounds such as Bronopol (2-bromo-2-nitropropane-1,3-diol), 2,2-dibromo-2-cyanoacetamide (DBNPA); aldehydes such as glutaraldehyde; phenoxyethanol; Biphenyl-2-ol; and zinc or sodium pyrithione.

In one embodiment, a liquid enzyme formulation comprises at least one polypeptide variant of the invention and at least one enzyme stabilizer. An enzyme stabilizer is selected from substances which are capable of reducing loss of enzymatic activity during storage of at least one enzyme comprised in a liquid enzyme concentrate. Reduced loss of enzymatic activity within this invention may mean that the loss of enzymatic activity is reduced by at least 5%, by at least 10%, by at least 15%, by at least 20%, by at least 25%, by at least 30%, by at least 40%, by at least 50%, by least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial enzymatic activity before storage.

In one embodiment, at least one enzyme stabilizer is selected from lipase stabilizing compounds. A lipase is stable according to the invention, when its lipolytic activity "available in application" equals 100% when compared to the initial lipolytic activity before storage. A lipase may be called stable within this invention if its lipolytic activity available in application is at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial lipolytic activity before storage.

Lipase may be stabilized in the presence of at least one compound selected from salts like NaCl or KCl, or alkali salts of lactic acid and formic acid.

The invention relates to a combination of at least one variant polypeptide of the invention and at least one other enzyme. In one aspect, such a combination is part of a liquid enzyme formulation at 20° C. and 101.3 kPa.

The combination of enzymes can be of the same class, for example a composition comprising a first lipase and a second lipase. Combinations of enzymes can be from a different class of enzymes, for example, a composition comprising a lipase and an amylase. Combinations of enzymes may comprise at least one variant lipase of the invention and one other enzyme. Combinations may comprise three enzymes, four enzymes, or more than four enzymes.

"Other enzyme" means any enzyme different from the lipase variants of the invention. At least one "other enzyme" may be selected from lipases, amylases, proteases, cellulases, mannanases, pectate lyases and nucleases.

Lipase

"Lipases", "lipolytic enzyme", "lipid esterase", all refer to an enzyme of EC class 3.1.1 ("carboxylic ester hydrolase"). Lipases (E.C. 3.1.1.3, Triacylglycerol lipase) usually hydrolyze triglycerides to more hydrophilic mono- and diglycerides, free fatty acids, and glycerol. Lipase enzymes usually includes also enzymes which are active on substrates different from triglycerides or cleave specific fatty acids, such as Phospholipase A (E.C. 3.1.1.4), Galactolipase (E.C. 3.1.1.26), cutinase (EC 3.1.1.74), and enzymes having sterol esterase activity (EC 3.1.1.13) and/or wax-ester hydrolase activity (EC 3.1.1.50).

Many lipase enzymes have been described in patents and published patent applications including, but not limited to: WO2000032758, WO2003/089620, WO2005/032496, WO2005/086900, WO200600976, WO2006/031699, WO2008/036863, WO2011/046812, and WO2014059360.

Lipases are used in detergent and cleaning products to remove grease, fat, oil, and dairy stains. Commercially available lipases include but are not limited to Lipolase™, Lipex™, Lipolex™ and Lipoclean™ (Novozymes A/S), Lumafast (originally from Genencor) and Lipomax (Gist-Brocades/now DSM).

Lipases according to the invention have "lipolytic activity". The methods for determining lipolytic activity are described in the literature (see e.g. Gupta et al. (2003), Biotechnol. Appl. Biochem. 37, p. 63-71). E.g. the lipase activity may be measured by ester bond hydrolysis in the substrate para-nitrophenyl palmitate (pNP-Palmitate, C: 16) and releases pNP which is yellow and can be detected at 405 nm.

Amylase

Alpha-amylase (E.C. 3.2.1.1) enzymes usually perform endohydrolysis of (1->4)-alpha-D-glucosidic linkages in polysaccharides containing three or more (1h->4)-alpha-linked D-glucose units. Amylase enzymes act on starch, glycogen and related polysaccharides and oligosaccharides in a random manner; reducing groups are liberated in the alpha-configuration. Other examples of amylase enzymes include Beta-amylase (E.C. 3.2.1.2), Glucan 1,4-alpha-maltotetraohydrolase (E.C. 3.2.1.60), Isoamylase (E.C. 3.2.1.68), Glucan 1,4-alpha-maltohexaosidase (E.C. 3.2.1.98), and Glucan 1,4-alpha-maltohydrolase (E.C. 3.2.1.133).

Many amylase enzymes have been described in patents and published patent applications including, but not limited to: WO 2002/068589, WO 2002/068597, WO 2003/083054, WO 2004/091544, and WO 2008/080093.

Amylases are known to derived from *Bacillus licheniformis* having SEQ ID NO:2 as described in WO 95/10603. Suitable variants are those which are at least 90% identical to SEQ ID NO: 2 as described in WO 95/10603 and/or comprising one or more substitutions in the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 which have amylolytic activity. Such variants are described in WO 94/02597, WO 94/018314, WO 97/043424 and SEQ ID NO:4 of WO 99/019467.

Amylases are known to derived from *B. stearothermophilus* having SEQ ID NO:6 as described in WO 02/10355 or an amylase which is at least 90% identical thereto having amylolytic activity. Suitable variants of SEQ ID NO:6 include those which is at least 90% identical thereto and/or further comprise a deletion in positions 181 and/or 182 and/or a substitution in position 193.

Amylases are known to derived from *Bacillus* sp. 707 having SEQ ID NO:6 as disclosed in WO 99/19467 or an amylase which is at least 90% identical thereto having amylolytic activity. Amylases are known from *Bacillus halmapalus* having SEQ ID NO:2 or SEQ ID NO:7 as described in WO 96/23872, also described as SP-722, or an amylase which is at least 90% identical to one of the sequences which has amylolytic activity.

Amylases are known to derived from *Bacillus* sp. DSM 12649 having SEQ ID NO:4 as disclosed in WO 00/22103 or an amylase which is at least 90% identical thereto having amylolytic activity.

Amylases are known from *Bacillus* strain TS-23 having SEQ ID NO:2 as disclosed in WO 2009/061380 or an amylase which is at least 90% identical thereto having amylolytic activity. Amylases are known from *Cytophaga* sp. having SEQ ID NO:1 as disclosed in WO 2013/184577 or an amylase which is at least 90% identical thereto having amylolytic activity.

Amylases are known from *Bacillus megaterium* DSM 90 having SEQ ID NO:1 as disclosed in WO 2010/104675 or an amylase which is at least 90% identical thereto having amylolytic activity.

Amylases are known having amino acids 1 to 485 of SEQ ID NO:2 as described in WO 00/60060 or amylases comprising an amino acid sequence which is at least 96% identical with amino acids 1 to 485 of SEQ ID NO:2 which have amylolytic activity.

Amylases are also known having SEQ ID NO: 12 as described in WO 2006/002643 or amylases having at least 80% identity thereto and have amylolytic activity. Suitable amylases include those having at least 80% identity compared to SEQ ID NO: 12 and/or comprising the substitutions at positions Y295F and M202LITV and have amylolytic activity.

Amylases are also known having SEQ ID NO:6 as described in WO 2011/098531 or amylases having at least 80% identity thereto having amylolytic activity. Suitable amylases include those having at least 80% identity compared to SEQ ID NO:6 and/or comprising a substitution at one or more positions selected from the group consisting of 193 [G,A,S,T or M], 195 [F,W,Y,L,I or V], 197 [F,W,Y,L,I or V], 198 [Q or N], 200 [F,W,Y,L,I or V], 203 [F,W,Y,L,I or V], 206 [F,W,Y,N,L,I,V,H,Q,D or E], 210 [F,W,Y,L,I or V], 212 [F,W,Y,L,I or V], 213 [G,A,S,T or M] and 243 [F,W,Y, L,I or V] and have amylolytic activity.

Amylases are known having SEQ ID NO:1 as described in WO 2013/001078 or amylases having at least 85% identity thereto having amylolytic activity. Suitable amylases include those having at least 85% identity compared to SEQ ID NO:1 and/or comprising an alteration at two or more (several) positions corresponding to positions G304, W140, W189, D134, E260, F262, W284, W347, W439, W469, G476, and G477 and having amylolytic activity.

Amylases are known having SEQ ID NO:2 as described in WO 2013/001087 or amylases having at least 85% identity thereto and having amylolytic activity. Suitable amylases include those having at least 85% identity compared to SEQ ID NO:2 and/or comprising a deletion of positions 181+182, or 182+183, or 183+184, which have amylolytic activity. Suitable amylases include those having at least 85% identity compared to SEQ ID NO:2 and/or comprising a deletion of positions 181+182, or 182+183, or 183+184, which comprise one or two or more modifications in any of positions corresponding to W140, W159, W167, Q169, W189, E194, N260, F262, W284, F289, G304, G305, R320, W347, W439, W469, G476 and G477 and have amylolytic activity.

Amylases also include hybrid α-amylase from above mentioned amylases as for example as described in WO 2006/066594.

Commercially available amylase enzymes include but are not limited to Amplify®, Duramyl™, Termamyl™, Fungamyl™, Stainzyme™, Stainzyme Plus™, Natalase™, Liquozyme X and BAN™ (from Novozymes A/S), and Rapidase™, Purastar™, Powerase™, Effectenz™ (M100 from DuPont), Preferenz™ (S1000, S110 and F1000; from DuPont), PrimaGreen™ (ALL; DuPont), Optisize™ (DuPont).

Amylases according to the invention have "amylolytic activity" or "amylase activity" according to the invention involves (endo)hydrolysis of glucosidic linkages in polysaccharides. α-amylase activity may be determined by assays for measurement of α-amylase activity. Examples of assays measuring α-amylase activity are: α-amylase activity can be determined by a method employing Phadebas tablets as substrate (Phadebas Amylase Test, supplied by Magle Life Science). Starch is hydrolyzed by the α-amylase giving soluble blue fragments. The absorbance of the resulting blue solution, measured spectrophotometrically at 620 nm, is a function of the α-amylase activity. The measured absorbance is directly proportional to the specific activity (activity/mg of pure α-amylase protein) of the α-amylase in question under the given set of conditions.

Alpha-amylase activity can also be determined by a method employing the Ethyliden-4-nitrophenyl-α-D-maltoheptaosid (EPS). D-maltoheptaoside is a blocked oligosaccharide which can be cleaved by an endo-amylase. Following the cleavage, the α-glucosidase included in the kit to digest the substrate to liberate a free PNP molecule which has a yellow color and thus can be measured by visible spectophotometry at 405 nm. Kits containing EPS substrate and α-glucosidase is manufactured by Roche Costum Biotech (cat. No. 10880078103). The slope of the time dependent absorption-curve is directly proportional to the specific activity (activity per mg enzyme) of the α-amylase in question under the given set of conditions.

Protease

Enzymes having proteolytic activity are called "proteases" or "peptidases". Proteases are active proteins exerting "protease activity" or "proteolytic activity".

Proteases are members of class EC 3.4Proteases include aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), metallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo-endopeptidases (EC 3.4.24), threonine endopeptidases (EC 3.4.25), endopeptidases of unknown catalytic mechanism (EC 3.4.99).

Commercially available protease enzymes include but are not limited to Lavergy™ Pro (BASF); Alcalase®, Blaze®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect® Prime, Purafect MA®, Purafect Ox®, Purafect OxP®, Puramax®, Properase®, FN2®, FN3®, FN4®, Excellase®, Eraser®, Ultimase®, Opticlean®, Effectenz®, Preferenz® and Optimase® (Danisco/DuPont), Axapem™ (Gist-Brocases N.V.), *Bacillus lentus* Alkaline Protease, and KAP (*Bacillus alkalophilus* subtilisin) from Kao.

At least one protease may be selected from serine proteases (EC 3.4.21). Serine proteases or serine peptidases (EC 3.4.21) are characterized by having a serine in the catalytically active site, which forms a covalent adduct with the substrate during the catalytic reaction. A serine protease may be selected from the group consisting of chymotrypsin (e.g., EC 3.4.21.1), elastase (e.g., EC 3.4.21.36), elastase (e.g., EC 3.4.21.37 or EC 3.4.21.71), granzyme (e.g., EC 3.4.21.78 or EC 3.4.21.79), kallikrein (e.g., EC 3.4.21.34, EC 3.4.21.35, EC 3.4.21.118, or EC 3.4.21.119,) plasmin (e.g., EC 3.4.21.7), trypsin (e.g., EC 3.4.21.4), thrombin (e.g., EC 3.4.21.5,) and subtilisin (also known as subtilopeptidase, e.g., EC 3.4.21.62), the latter hereinafter also being referred to as "subtilisin".

A sub-group of the serine proteases tentatively designated subtilases has been proposed by Siezen et al. (1991), Protein Eng. 4:719-737 and Siezen et al. (1997), Protein Science 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997), Protein Science 6:501-523. The subtilases may be divided into 6 sub-divisions, i.e. the subtilisin family, thermitase family, the proteinase K family, the lantibiotic peptidase family, the kexin family and the pyrolysin family.

A subgroup of the subtilases are the subtilisins which are serine proteases from the family S8 as defined by the MEROPS database (http://merops.sanger.ac.uk). Peptidase family S8 contains the serine endopeptidase subtilisin and its homologues. In subfamily S8A, the active site residues frequently occurs in the motifs Asp-Thr/Ser-Gly (which is similar to the sequence motif in families of aspartic endopeptidases in clan AA), His-Gly-Thr-His and Gly-Thr-Ser-Met-Ala-Xaa-Pro. Most members of the peptidase family S8 are active at neutral-mildly alkali pH. Many peptidases in the family are thermostable.

Prominent members of family S8, subfamily A are:

| name | MEROPS Family S8, Subfamily A |
|---|---|
| Subtilisin Carlsberg | S08.001 |
| Subtilisin lentus | S08.003 |
| Thermitase | S08.007 |
| Subtilisin BPN' | S08.034 |
| Subtilisin DY | S08.037 |
| Alkaline peptidase | S08.038 |
| Subtilisin ALP 1 | S08.045 |
| Subtilisin sendai | S08.098 |
| Alkaline elastase YaB | S08.157 |

Parent proteases of the subtilisin type (EC 3.4.21.62) and variants may be bacterial proteases. Said bacterial protease may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* protease, or a Gram-negative bacterial polypeptide such as a *Campylobacter, E. coli, Flavobacterium, Fusobacterium, Helicobacter, lyobacter, Neisseria, Pseudomonas, Salmonella*, or *Ureaplasma* protease. A review of this family is provided, for example, in "Subtilases: Subtilisin-like Proteases" by R. Siezen, pages 75-95 in "Subtilisin enzymes", edited by R. Bott and C. Betzel, New York, 1996.

At least one protease may be selected from the following: subtilisin from *Bacillus amyloliquefaciens* BPN' (described by Vasantha et al. (1984) J. Bacteriol. Volume 159, p. 811-819 and JA Wells et al. (1983) in Nucleic Acids Research, Volume 11, p. 7911-7925); subtilisin from *Bacillus licheniformis* (subtilisin Carlsberg; disclosed in E L Smith et al. (1968) in J. Biol Chem, Volume 243, pp. 2184-2191, and Jacobs et al. (1985) in Nucl. Acids Res, Vol 13, p. 8913-8926); subtilisin PB92 (original sequence of the alkaline protease PB92 is described in EP 283075 A2); subtilisin 147 and/or 309 (Esperase®, Savinase®, respectively) as disclosed in WO 89/06279; subtilisin from *Bacillus lentus* as disclosed in WO 91/02792, such as from *Bacillus lentus* DSM 5483 or the variants of *Bacillus lentus* DSM 5483 as described in WO 95/23221; subtilisin from *Bacillus alcalophilus* (DSM 11233) disclosed in DE 10064983; subtilisin from *Bacillus gibsonii* (DSM 14391) as disclosed in WO 2003/054184; subtilisin from *Bacillus* sp. (DSM 14390) disclosed in WO 2003/056017; subtilisin from *Bacillus* sp. (DSM 14392) disclosed in WO 2003/055974; subtilisin from *Bacillus gibsonii* (DSM 14393) disclosed in WO 2003/054184; subtilisin having SEQ ID NO: 4 as described in WO 2005/063974; subtilisin having SEQ ID NO: 4 as described in WO 2005/103244; subtilisin having SEQ ID NO: 7 as described in WO 2005/103244; and subtilisin having SEQ ID NO: 2 as described in application DE 102005028295.4.

At least one subtilisin may be subtilisin 309 (which might be called Savinase® herein) as disclosed as sequence a) in Table I of WO 89/06279 or a variant which is at least 80% identical thereto and has proteolytic activity.

Proteases are known as comprising the variants described in: WO 92/19729, WO 95/23221, WO 96/34946, WO 98/20115, WO 98/20116, WO 99/11768, WO 01/44452, WO 02/088340, WO 03/006602, WO 2004/03186, WO 2004/041979, WO 2007/006305, WO 2011/036263, WO 2011/036264, and WO 2011/072099. Suitable examples comprise especially protease variants of subtilisin protease derived from SEQ ID NO:22 as described in EP 1921147 (with amino acid substitutions in one or more of the following positions: 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and 274 which have proteolytic activity. In addition, a subtilisin protease is not mutated at positions Asp32, His64 and Ser221.

Suitable proteases include protease variants having proteolytic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical when compared to the full-length polypeptide sequence of the parent enzyme as disclosed above.

At least one subtilisin may have SEQ ID NO:22 as described in EP 1921147, or is a variant thereof which is at least 80% identical SEQ ID NO:22 as described in EP 1921147 and has proteolytic activity. In one embodiment, a subtilisin is at least 80% identical to SEQ ID NO:22 as described in EP 1921147 and is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, subtilisin is at least 80% identical to SEQ ID NO:22 as described in EP 1921147 and is characterized by having amino acid glutamic acid (E), or aspartic acid (D), at position 101 (according to BPN' numbering) and has proteolytic activity. Such a subtilisin variant may comprise an amino acid substitution at position 101, such as R101E or R101D, alone or in combination with one or more substitutions at positions 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and/or 274 (according to BPN' numbering) and has proteolytic activity. In one embodiment, said protease comprises one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h).

A suitable subtilisin may be at least 80% identical to SEQ ID NO:22 as described in EP 1921147 and is characterized by comprising one amino acid (according to (a)-(h)) or combinations according to (i) together with the amino acid 101E, 101D, 101N, 101Q, 101A, 101G, or 101S (according to BPN' numbering) and has proteolytic activity.

In one embodiment, a subtilisin is at least 80% identical to SEQ ID NO:22 as described in EP 1921147 and is characterized by comprising the mutation (according to BPN' numbering) R101E, or S3T+V4I+V205I, or S3T+V4I+R101E+V205I or S3T+V4I+V199M+V205I+L217D, and has proteolytic activity.

In another embodiment, the subtilisin comprises an amino acid sequence having at least 80% identity to SEQ ID NO:22 as described in EP 1921147 and being further characterized by comprising S3T+V4I+S9R+A15T+V68A+D99S+R101S+A103S+I104V+N218D (according to the BPN' numbering) and has proteolytic activity.

A subtilisin may have an amino acid sequence being at least 80% identical to SEQ ID NO:22 as described in EP 1921147 and being further characterized by comprising R101E, and one or more substitutions selected from the group consisting of S156D, L262E, Q137H, S3T, R45E,D, Q, P55N, T58W,Y,L, Q59D,M,N,T, G61 D,R, S87E, G97S, A98D,E,R, S106A,W, N117E, H120V,D,K,N, S125M, P129D, E136Q, S144W, S161T, S163A,G, Y171 L, A172S, N185Q, V199M, Y209W, M222Q, N238H, V244T, N261T,D and L262N,Q,D (as described in WO 2016/096711 and according to the BPN' numbering), and has proteolytic activity.

Proteases according to the invention have proteolytic activity. The methods for determining proteolytic activity are well-known in the literature (see e.g. Gupta et al. (2002), Appl. Microbiol. Biotechnol. 60: 381-395). Proteolytic activity may be determined by using Succinyl-Ala-Ala-Pro-Phe-p-nitroanilide (Suc-AAPF-pNA, short AAPF; see e.g. DelMar et al. (1979), Analytical Biochem 99, 316-320) as substrate. pNA is cleaved from the substrate molecule by proteolytic cleavage, resulting in release of yellow color of free pNA which can be quantified by measuring OD405.

Cellulase

"Cellulases", "cellulase enzymes" or "cellulolytic enzymes" are enzymes involved in hydrolysis of cellulose. Three major types of cellulases are known, namely endo-ss-1,4-glucanase (endo-1,4-P-D-glucan 4-glucanohydrolase, E.C. 3.2.1.4; hydrolyzing β-1,4-glucosidic bonds in cellulose), cellobiohydrolase (1,4-P-D-glucan cellobiohydrolase, EC 3.2.1.91), and ss-glucosidase (EC 3.2.1.21).

Cellulase enzymes have been described in patents and published patent applications including, but not limited to: WO1997/025417, WO1998/024799, WO2003/068910, WO2005/003319, and WO2009020459.

Commercially available cellulase enzymes include are Celluzyme™, Endolase™, Carezyme™, Cellusoft™, Renozyme™, Celluclean™ (from Novozymes A/S), Ecostone™, Biotouch™, Econase™, Ecopulp™ (from AB Enzymes Finland), Clazinase™, and Puradax HA™, Genencor detergent cellulase L, IndiAge™ Neutra (from Genencor International Inc./DuPont), Revitalenz™ (2000 from DuPont), Primafast™ (DuPont) and KAC-500™ (from Kao Corporation).

Cellulases according to the invention have "cellulolytic activity" or "cellulase activity". Assays for measurement of cellulolytic activity include: cellulolytic activity may be determined by virtue of the fact that cellulase hydrolyses carboxymethyl cellulose to reducing carbohydrates, the reducing ability of which is determined colorimetrically by means of the ferricyanide reaction, according to Hoffman, W. S., J. Biol. Chem. 120, 51 (1937).

Mannanase

Mannase (E.C. 3.2.1.78) enzymes hydrolyse internal β-1,4 bonds in mannose. Polymers. "Mannanase" may be an alkaline mannanase of Family 5 or 26. Mannanase enzymes are known to be derived from wild-type from Bacillus or Humicola, particularly B. agaradhaerens, B. licheniformis, B. halodurans, B. clausii, or H. insolens. Suitable mannanases are described in WO 99/064619.

Commercially available mannanase enzymes include: Mannaway® (Novozymes AIS).

Pectate Lyase

Pectate lyase (E.C. 4.2.2.2) enzymes eliminative cleavage of (1->4)-alpha-D-galacturonan to give oligosaccharides with 4-deoxy-alpha-D-galact-4-enuronosyl groups at their non-reducing ends.

Pectate lyase enzymes have been described in patents and published patent applications including, but not limited to: WO2004/090099. Pectate lyase are known to be derived from Bacillus, particularly B. licheniformis or B. agaradhaerens, or a variant derived of any of these, e.g. as described in U.S. Pat. No. 6,124,127, WO 99/027083, WO 99/027084, WO 2002/006442, WO 2002/092741, WO 2003/095638.

Commercially available pectate lyase enzymes include: Xpect™, Pectawash™ and Pectaway™ (Novozymes A/S); PrimaGreen™, EcoScour (DuPont).

Nuclease

Nuclease (EC 3.1.21.1) also known as Deoxyribonuclease I, or DNase preforms endonucleolytic cleavage to 5'-phosphodinucleotide and 5'-phosphooligonucleotide end-products.

Nuclease enzymes have been described in patents and published patent applications including, but not limited to: U.S. Pat. No. 3,451,935, GB1300596, DE10304331, WO2015155350, WO2015155351, WO2015166075, WO2015181287, and WO2015181286.

In one aspect of the invention, at least one lipase variant of the invention is provided in combination with at least one subtilisin. In one embodiment, a lipase variant of the invention is stable against proteolytic degradation. In one embodiment, a lipase variant of the invention has increased stability against proteolytic degradation when compared to the respective lipase parent. In one embodiment, at least one subtilisin is selected from subtilisin 309 as disclosed as sequence a) in Table I of WO 89/06279 or a variant thereof which is at least 80% identical thereto and has proteolytic activity. In one embodiment, a lipase variant of the invention has increased stability against proteolytic degradation in the presence of subtilisin 309 or a variant thereof which is at least 80% identical thereto when compared to the lipase according to SEQ ID NO: 1.

The protease may itself be stabilized by a protease stabilizer or the protease may be non-stabilized. Therefore, in one embodiment, a lipase variant of the invention has increased stability against proteolytic degradation such as non-stabilized subtilisin 309 or a non-stabilized variant thereof which is at least 80% identical thereto, when compared to the lipase according to SEQ ID NO: 1. In another embodiment, a lipase variant of the invention has increased stability against proteolytic degradation in the presence of stabilized subtilisin 309 or in the presence of stabilized variant thereof which is at least 80% identical thereto, when compared to the lipase according to SEQ ID NO: 1.

Protease stabilizers may be selected from boron-containing compounds. Boron-containing compounds are selected from boric acid or its derivatives and from boronic acid or its derivatives such as aryl boronic acids or its derivatives, from salts thereof, and from mixtures thereof. Boric acid herein may be called orthoboric acid.

In one embodiment, boron-containing compound is selected from the group consisting of aryl boronic acids and its derivatives. In one embodiment, boron-containing compound is selected from the group consisting of benzene boronic acid (BBA) which is also called phenyl boronic acid (PBA), derivatives thereof, and mixtures thereof. In one embodiment, phenyl boronic acid derivatives are selected from the group consisting of the derivatives of formula (I) and (II) formula:

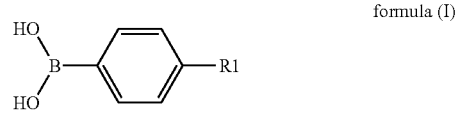

formula (I)

-continued

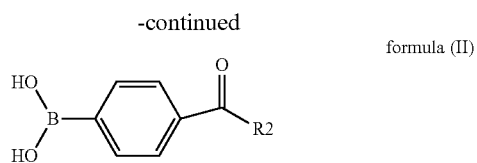

formula (II)

Wherein $R^1$ is selected from the group consisting of hydrogen, hydroxy, non-substituted or substituted $C_1$-$C_6$ alkyl, and non-substituted or substituted $C_1$-$C_6$ alkenyl; in a preferred embodiment, R is selected from the group consisting of hydroxy, and non-substituted $C_1$ alkyl.

Wherein $R^2$ is selected from the group consisting of hydrogen, hydroxy, non-substituted or substituted $C_1$-$C_6$ alkyl, and non-substituted or substituted $C_1$-$C_6$ alkenyl; in a preferred embodiment, R is selected from the group consisting of H, hydroxy, and substituted $C_1$ alkyl.

In one embodiment phenyl-boronic acid derivatives are selected from the group consisting of 4-formyl phenyl boronic acid (4-FPBA), 4-carboxy phenyl boronic acid (4-CPBA), 4-(hydroxymethyl) phenyl boronic acid (4-HMPBA), and p-tolylboronic acid (p-TBA).

Other suitable derivatives include: 2-thienyl boronic acid, 3-thienyl boronic acid, (2-acetamidophenyl) boronic acid, 2-benzofuranyl boronic acid, 1-naphthyl boronic acid, 2-naphthyl boronic acid, 2-FPBA, 3-FBPA, 1-thianthrenyl boronic acid, 4-dibenzofuran boronic acid, 5-methyl-2-thienyl boronic acid, 1-benzothiophene-2 boronic acid, 2-furanyl boronic acid, 3-furanyl boronic acid, 4,4 biphenyl-diboronic acid, 6-hydroxy-2-naphthaleneboronic acid, 4-(methylthio) phenyl boronic acid, 4-(trimethylsilyl) phenyl boronic acid, 3-bromothiophene boronic acid, 4-methylthiophene boronic acid, 2-naphthyl boronic acid, 5-bromothiophene boronic acid, 5-chlorothiophene boronic acid, dimethylthiophene boronic acid, 2-bromophenyl boronic acid, 3-chlorophenyl boronic acid, 3-methoxy-2-thiophene boronic acid, p-methyl-phenylethyl boronic acid, 2-thianthrenyl boronic acid, di-benzothiophene boronic acid, 9-anthracene boronic acid, 3,5 dichlorophenyl boronic, acid, diphenyl boronic acid anhydride, o-chlorophenyl boronic acid, p-chlorophenyl boronic acid, m-bromophenyl boronic acid, p-bromophenyl boronic acid, p-fluorophenyl boronic acid, octyl boronic acid, 1,3,5 trimethylphenyl boronic acid, 3-chloro-4-fluorophenyl boronic acid, 3-aminophenyl boronic acid, 3,5-bis-(trifluoromethyl) phenyl boronic acid, 2,4 dichlorophenyl boronic acid, 4-methoxyphenyl boronic acid, and mixtures thereof.

In one embodiment, at least one boron-containing compound is used together with at least one polyol containing from 2 to 6 hydroxyl groups to stabilize protease. Suitable examples include glycol, propylene glycol, 1,2-propane diol, 1,2-butane diol, ethylene glycol, hexylene glycol, glycerol, sorbitol, mannitol, erythriol, glucose, fructose, lactore, and erythritan.

The variant polypeptides of the invention may be used in several industries where lipases are useful in processing applications and/or where lipases are useful components of formulations.

The lipase variants of the invention may be used in food formulations, for example the enzyme can be an additive for baking (see WO 2017/142904). In one embodiment, the inventive polypeptides having lipase activity can be used in a method of preparing a dough, or in a baked product prepared from the dough, wherein the method comprises the steps of (a) adding the polypeptides having lipase activity to the dough and (b) baking it.

The lipase variants of the invention can also be used in the oilseed processing industry, for example the enzyme is use for processing plant (soy, canola) oil (WO 2005/086900). In one embodiment, the inventive polypeptides having lipase activity can be used in a method for processing fats, oils, or oilseeds; wherein the method comprises (a) providing a fat, an oil, or an oilseed; (b) providing a polypeptide having lipase activity; and (c) contacting the polypeptide with the fat, the oil, or the oilseed, wherein the polypeptide hydrolyses the fat to a desired product.

The lipase variants of the invention can be used in feed formulations (see U.S. Pat. No. 8,735,123). In one embodiment, the inventive polypeptides having lipase activity can be used in a method for feeding an animal; wherein the method comprises (a) providing a feed formulation or pellet, (b) providing the lipase in the feed formulation or pellet, and (c) feeding the animal the feed formulation.

The lipase variants of the invention can be used in the starch processing industry, for example to process byproducts such as oil in the process of conversion of starch to ethanol or sugars with amylases (high fructose corn syrup) (see WO 2004/029193). In one embodiment, the inventive polypeptides having lipase activity can be used in a method for making ethanol, wherein in the method comprises, (a) providing a material from ethanol production, wherein the material has an oil, (b) providing a lipase, and (c) contacting the material with the lipase, wherein the lipase helps improving the recovery of oil from the material. In another embodiment, the lipase variants of the invention can be used in biodiesel production (U.S. Pat. No. 7,550,278).

The lipase variants of the invention are used in pulp and paper processing, for example, the enzymes (lipase) can be used for improving paper strength (see WO 2006/031699), and pitch control (see U.S. 2010/0269989). In one embodiment, the inventive polypeptides having lipase activity can be used in a method for processing pulp or paper, wherein the method comprises (a) providing a pulp or paper, (b) providing a lipase, and (c) contacting the pulp or paper with the lipase, wherein the lipase improves the strength of the pulp or paper.

The lipase variants of the invention can be used for mining and oil well services, for example cellulases, amylases, and/or lipases can be used for breaking guar during oil well fracturing (U.S. Pat. No. 5,725,771).

The lipase variants of the invention may be used in detergent formulations or cleaning formulations. In one embodiment, the inventive polypeptides having lipase activity can be used in a method of cleaning, comprising the steps of (a) providing a surface to be cleaned from fatty stains; (b) providing a detergent formulation of the invention; and (c) contacting the surface to be cleaned from fatty stains of (a) with the detergent of (b); wherein in the polypeptide comprised in the detergent removes the fatty stain from the surface to be cleaned from fatty stains. In one embodiment, the invention relates to a method of cleaning or washing textiles, hard surfaces, or dishes, wherein the method comprises, (a) providing a textile, hard surfaces, or dishes, (b) providing a lipase, and (c) contacting the textiles, hard surfaces, or dishes, and the lipase, wherein the lipase removes a fatty stain from the textiles, hard surfaces, or dishes. The detergent formulation provided in step (b) of the method at least comprises a lipase of the invention. The detergent formulation provided in step (b) of the method may comprise at least one additional enzyme which is different from the lipase of the invention selected from lipases, amylases, proteases, cellulases, mannanases, laccases, pectinases, and nucleases.

The invention relates to detergent formulations or cleaning formulations comprising at least one lipase variant of the invention and at least one detergent component. "Detergent formulation" or "cleaning formulation" means compositions designated for cleaning soiled material. Cleaning includes laundering and hard surface cleaning. Soiled material according to the invention includes textiles and/or hard surfaces.

The term "laundering" relates to both household laundering and industrial laundering and means the process of treating textiles with a solution containing a detergent formulation of the present invention. The laundering process may be carried out by using technical devices such as a household or an industrial washing machine. Alternatively, the laundering process may be done by hand.

The term "textile" means any textile material including yarns (thread made of natural or synthetic fibers used for knitting or weaving), yarn intermediates, fibers, non-woven materials, natural materials, synthetic materials, as well as fabrics (a textile made by weaving, knitting or felting fibers) made of these materials such as garments (any article of clothing made of textile), cloths and other articles.

The term "fibers" includes natural fibers, synthetic fibers, and mixtures thereof. Examples of natural fibers are of plant (such as flax, jute and cotton) or animal origin, comprising proteins like collagen, keratin and fibroin (e.g. silk, sheep wool, angora, mohair, cashmere). Examples for fibers of synthetic origin are polyurethane fibers such as Spandex® or Lycra®, polyester fibers, polyolefins such as elastofin, or polyamide fibers such as nylon. Fibers may be single fibers or parts of textiles such as knitwear, wovens, or nonwovens.

The term "hard surface cleaning" is defined herein as cleaning of hard surfaces wherein hard surfaces may include any hard surfaces in the household, such as floors, furnishing, walls, sanitary ceramics, glass, metallic surfaces including cutlery or dishes.

The term "dish wash" refers to all forms of washing dishes, e.g. by hand or automatic dish wash. Dish washing includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The detergent formulation of the invention comprises one or more detergent component(s). The component(s) chosen depend on the desired cleaning application and/or physical form of a detergent formulation.

The term "detergent component" is defined herein to mean any types of ingredient, which is suitable for detergent formulation, such as surfactants, building agents, polymers, bleaching systems. Any component(s) known in the art acknowledging their known characteristics are suitable detergent component(s) according to the invention. Detergent components in one embodiment means components which provide washing or cleaning performance or which effectively aid the processing (maintain physical characteristics during processing, storage and use; e.g. rheology modifiers, hydrotropes, desiccants) when present in effective amounts.

Usually, a detergent formulation is a complex formulation of more than two detergent components.

Detergent components may have more than one function in the final application of a detergent formulation, therefore any detergent component mentioned in the context of a specific function herein, may also have another function in the final application of a detergent formulation. The function of a specific detergent component in the final application of a detergent formulation usually depends on its amount within the detergent formulation, i.e. the effective amount of a detergent component.

The term "effective amount" includes amounts of individual components to provide effective stain removal and effective cleaning conditions (e.g. pH, quantity of foaming), amounts of certain components to effectively provide optical benefits (e.g. optical brightening, dye transfer inhibition), and amounts of certain components to effectively aid the processing (maintain physical characteristics during processing, storage and use; e.g. rheology modifiers, hydrotropes, desiccants).

In one embodiment, a detergent formulation is a formulation of more than two detergent components, wherein at least one component is effective in stain-removal, at least one component is effective in providing the optimal cleaning conditions, and at least one component is effective in maintaining the physical characteristics of the detergent.

Cleaning performance is evaluated under relevant cleaning conditions. The term "relevant cleaning conditions" herein refers to the conditions, particularly cleaning temperature, time, cleaning mechanics, suds concentration, type of detergent and water hardness, actually used in laundry machines, automatic dish washers or in manual cleaning processes.

Cleaning performance of lipase containing detergents may be called degreasing performance herein. Degreasing performance may be related to the ability of the detergent formulation to remove fatty stains deposited on textiles.

Fats can be sub-classified as fat, grease or oil depending on the melting temperature. Oil is usually liquid at room temperature. Grease has a higher viscosity than oil at room temperature and be called pasty. The removal of oily and greasy stains deposited on textiles, due to the relatively low melting temperature of oil and grease, is supported by laundering temperatures $\geq 40°$ C. Fatty deposits comprising fatty compounds having a melting temperature $>30°$ C., means fats remaining solid at temperatures $\leq 30°$ C.

Fatty stains deposited on textiles may be called fatty deposits herein. In one embodiment, fatty deposits comprise fatty compounds having a melting point $>40°$ C., meaning that such fatty compounds remain solid at laundering temperatures $\leq 40°$ C. In one embodiment, fatty deposits comprise fatty compounds having a melting point $>30°$ C., meaning that such fatty compounds remain solid at laundering temperatures $\leq 30°$ C.

In one aspect, the invention relates to a solid or liquid laundry formulation for laundering temperatures $\leq 40°$ C. comprising at least one lipase variant of the invention and the use of said formulation to remove fatty deposits comprising fatty compounds having a melting temperature $>40°$ C. at laundering temperatures $\leq 40°$ C. In one embodiment, the invention relates to a solid or liquid laundry formulation for laundering temperatures $\leq 30°$ C. comprising at least one lipase variant of the invention and the use of said formulation to remove fatty deposits comprising fatty compounds having a melting temperature $>30°$ C. at laundering temperatures $\leq 30°$ C. In one embodiment, the invention relates to a solid or liquid laundry formulation for laundering temperatures $\leq 30°$ C. comprising at least one lipase variant of the invention and the use of said formulation to remove fatty deposits comprising fatty compounds having a melting temperature $>40°$ C. at laundering temperatures $\leq 30°$ C. In one embodiment, the invention relates to a solid or liquid laundry formulation for laundering temperatures $\leq 20°$ C. comprising at least one lipase variant of the invention and the use of said formulation to remove fatty deposits comprising fatty compounds having a melting temperature >20° C. at laundering temperatures ≤20° C. In one embodiment, the invention relates to a solid or liquid laundry formulation for laundering temperatures ≤20° C. comprising at least one lipase variant of the invention and the use of said formulation to remove fatty deposits comprising fatty compounds having a melting temperature >30° C. at laundering temperatures ≤20° C. In one embodiment, the invention relates to a solid or liquid laundry formulation for laundering temperatures ≤20° C. comprising at least one lipase variant of the invention and the use of said formulation to remove fatty deposits comprising fatty compounds having a melting temperature >40° C. at laundering temperatures ≤20° C.

Degreasing performance herein is meant to be improved when removal of fatty stains is improved. Improved in this context may mean that the inventive lipase and/or detergent formulation comprising at least one inventive lipase shows better degreasing performance when compared to non-inventive lipase and/or laundry formulations lacking inventive lipases and/or laundry formulations comprising the parent lipase. The removal of fatty stains may occur due to enzymatic degradation and/or solubilization and/or dispersion and/or emulsifying of the fatty compounds deposited on textile.

Individual detergent components and usage in detergent formulation are known to those skilled in the art. Suitable detergent components comprise inter alia surfactants, builders, polymers, alkaline, bleaching systems, fluorescent whitening agents, suds suppressors and stabilizers, hydrotropes, and corrosion inhibitors. Further examples are described e.g. in "complete Technology Book on Detergents with Formulations (Detergent Cake, Dishwashing Detergents, Liquid & Paste Detergents, Enzyme Detergents, Cleaning Powder & Spray Dried Washing Powder)", Engineers India Research Institute (EIRI), 6$^{th}$ edition (2015). Another reference book for those skilled in the art may be "Detergent Formulations Encyclopedia", Solverchem Publications, 2016.

Detergent components vary in type and/or amount in a detergent formulation depending on the desired application such as laundering white textiles, colored textiles, and wool. The component(s) chosen further depend on physical form of a detergent formulation (liquid, solid, gel, provided in pouches or as a tablet, etc). The component(s) chosen e.g. for laundering formulations further depend on regional conventions which themselves are related to aspects like washing temperatures used, mechanics of laundry machine (vertical vs. horizontal axis machines), water consumption per wash cycle etc. and geographical characteristics like average hardness of water.

For example: A low detergent concentration system includes laundering formulations where less than about 800 ppm of detergent components are present in the wash water. A medium detergent concentration includes laundering formulations where between about 800 ppm and about 2,000 ppm of detergent components are present in the wash water. A high detergent concentration includes laundering formulations where more than about 2,000 ppm of detergent components are present in the wash water.

The numeric ranges recited for the individual detergent components provide amounts comprised in detergent formulations. Such ranges have to be understood to be inclusive of the numbers defining the range and include each integer within the defined range.

If not described otherwise, "% by weight" or "% w/w" is meant to be related to total detergent formulation. In this case "% by weight" or "% w/w" is calculated as follows: concentration of a substance as the weight of that substance divided by the total weight of the composition, multiplied by 100.

Detergent formulations of the invention may comprise one or more surfactant(s). "Surfactant" (synonymously used herein with "surface active agent") means an organic chemical that, when added to a liquid, changes the properties of that liquid at an interface. According to its ionic charge, a surfactant is called non-ionic, anionic, cationic, or amphoteric.

Non-limiting examples of surfactants are disclosed McCutcheon's 2016 Detergents and Emulsifiers, and McCutcheon's 2016 Functional Materials, both North American and International Edition, MC Publishing Co, 2016 edition. Further useful examples are disclosed in earlier editions of the same publications which are known to those skilled in the art.

Non-ionic surfactant means a surfactant that contains neither positively nor negatively charged (i.e. ionic) functional groups. In contrast to anionic and cationic surfactants, non-ionic surfactants do not ionize in solution.

Examples provided below for surfactants of any kind are to be understood to be non-limiting.

Non-ionic surfactants may be compounds of the general formulae (IIIa) and (IIIb):

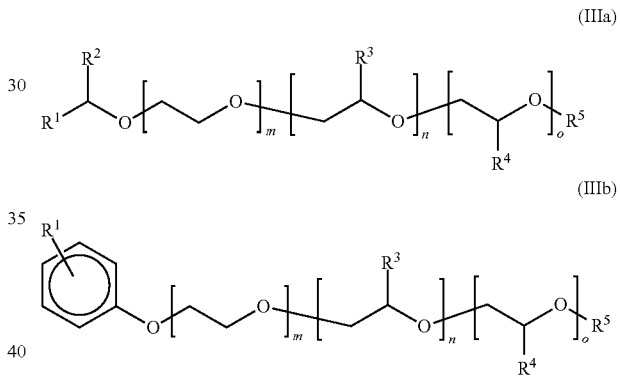

The variables of the general formulae (IIIa) and (IIIb) are defined as follows:

$R^1$ is selected from $C_1$-$C_{23}$ alkyl and $C_2$-$C_{23}$ alkenyl, wherein alkyl and/or alkenyl are linear or branched; examples are n-$C_7H_{15}$, n-$C_9H_{19}$, n-$C_{11}H_{23}$, n-$C_{13}H_{27}$, n-$C_{15}H_{31}$, n-$C_{17}H_{35}$, i-$C_9H_{19}$, i-$C_{12}H_{25}$.

$R^2$ is selected from H, $C_1$-$C_{20}$ alkyl and $C_2$-$C_{20}$ alkenyl, wherein alkyl and/or alkenyl are linear or branched.

$R^3$ and $R^4$, each independently selected from $C_1$-$C_{16}$ alkyl, wherein alkyl is linear or branched; examples are methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl.

$R^5$ is selected from H and $C_1$-$C_{18}$ alkyl, wherein alkyl is linear or branched.

The integers of the general formulae (IIIa) and (IIIb) are defined as follows: m is in the range of zero to 200, preferably 1-80, more preferably 3-20; n and o, each independently in the range of zero to 100; n preferably is in the range of 1 to 10, more preferably 1 to 6; o preferably is in the range of 1 to 50, more preferably 4 to 25. The sum of m, n and o is at least one, preferably the sum of m, n and o is in the range of 5 to 100, more preferably in the range of from 9 to 50.

The non-ionic surfactants of the general formula (IIIa) and (IIIb) may be of any structure, is it block or random structure, and is not limited to the displayed sequences.

In one embodiment, the detergent formulation comprises at least one non-ionic surfactant selected from general formula (IIIa), wherein m is in the range of 3 to 11, preferably not more than 7; n and o is 0, $R^1$ is $C_{12}$-$C_{14}$, $R^5$ is H. The detergent formulation may comprise at least two non-ionic surfactants, selected from compounds of general formula (IIIa), wherein one of said non-ionic surfactants is characterized in $R^1$ being $C_{12}$, $R^5$ being H, m is 7, n and o=0, and the other surfactant is characterized in $R^1$ being $C_{14}$, $R^5$ being H, m being 7, n and o=0.

Non-ionic surfactants may further be compounds of the general formula (IV), which might be called alkyl-polyglycosides (APG):

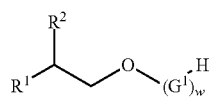

(IV)

The variables of the general formula (IV) are defined as follows:

$R^1$ is selected from $C_1$-$C_{17}$ alkyl and $C_2$-$C_{17}$ alkenyl, wherein alkyl and/or alkenyl are linear or branched; examples are n-$C_7H_{15}$, n-$C_9H_{19}$, n-$C_{11}H_{23}$, n-$C_{13}H_{27}$, n-$C_{15}H_{31}$, n-$C_{17}H_{35}$, i-$C_9H_{19}$, i-$C_{12}H_{25}$.

$R^2$ is selected from H, $C_1$-$C_{17}$ alkyl and $C_2$-$C_{17}$ alkenyl, wherein alkyl and/or alkenyl are linear or branched.

$G^1$ is selected from monosaccharide residues with 4 to 6 carbon atoms, such as glucose and xylose.

The integer w of the general formula (IV) is in the range of from 1.1 to 4, w being an average number.

Non-ionic surfactants may further be compounds of general formula (V):

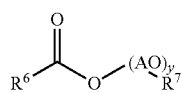

(V)

The variables of the general formula (V) are defined as follows:

AO is selected from ethylene oxide (EO), propylene oxide (PO), butylene oxide (BO), and mixtures thereof.

$R^6$ is selected from $C_5$-$C_{17}$ alkyl and $C_5$-$C_{17}$ alkenyl, wherein alkyl and/or alkenyl are linear or branched.

$R^7$ is selected from H, $C_1$-$C_{18}$-alkyl, wherein alkyl is linear or branched.

The integer y of the general formula (V) is a number in the range of 1 to 70, preferably 7 to 15.

Non-ionic surfactants may further be selected from sorbitan esters and/or ethoxylated or propoxylated sorbitan esters. Non-limiting examples are products sold under the trade names SPAN and TWEEN.

Non-ionic surfactants may further be selected from alkoxylated mono- or di-alkylamines, fatty acid monoethanolamides (FAMA), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), and combinations thereof.

Mixtures of two or more different non-ionic surfactants may also be present in detergent formulations according to the present invention.

Amphoteric surfactants are those, depending on pH, which can be either cationic, zwitterionic or anionic.

Surfactants may be compounds comprising amphoteric structures of general formula (VI), which might be called modified amino acids (proteinogenic as well as non-proteinogenic):

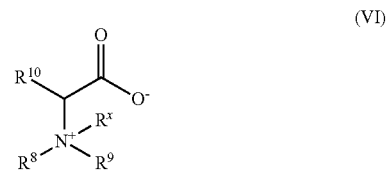

(VI)

The variables in general formula (VI) are defined as follows:

$R^8$ is selected from H, $C_1$-$C_4$ alkyl, $C_2$-$C_4$ alkenyl, wherein alkyl and/or are linear or branched.

$R^9$ is selected from $C_1$-$C_{22}$ alkyl, $C_2$-$C_{22}$ alkenyl, $C_{10}$-$C_{22}$ alkylcarbonyl, and $C_{10}$-$C_{22}$ alkenylcarbonyl.

$R^{10}$ is selected from H, methyl, —$(CH_2)_3$NHC(NH)$NH_2$, —$CH_2$C(O)$NH_2$, —$CH_2$C(O)OH, —$(CH_2)_2$C(O)$NH_2$, —$(CH_2)_2$C(O)OH, (imidazole-4-yl)-methyl, —CH($CH_3$) $C_2H_5$, —$CH_2$CH($CH_3$)$_2$, —$(CH_2)_4NH_2$, benzyl, hydroxymethyl, —CH(OH)$CH_3$, (indole-3-yl)-methyl, (4-hydroxyphenyl)-methyl, isopropyl, —$(CH_2)_2$S$CH_3$, and —$CH_2$SH.

$R^x$ is selected from H and $C_1$-$C_4$ alkyl.

Surfactants may further be compounds comprising amphoteric structures of general formulae (VIIa), (VIIb), or (VIIc), which might be called betaines and/or sulfobetaines:

(VIIa)

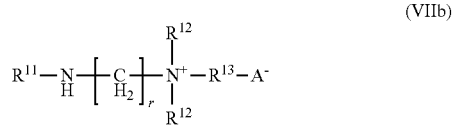

(VIIb)

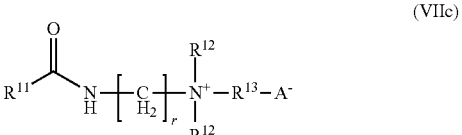

(VIIc)

The variables in general formulae (VIIa), (VIIb) and (VIIc) are defined as follows:

$R^{11}$ is selected from linear or branched $C_7$-$C_{22}$ alkyl and linear or branched $C_7$-$C_{22}$ alkenyl.

$R^{12}$ are each independently selected from linear $C_1$-$C_4$ alkyl.

$R^{13}$ is selected from $C_1$-$C_5$ alkyl and hydroxy $C_1$-$C_5$ alkyl; for example 2-hydroxypropyl.

$A^-$ is selected from carboxylate and sulfonate.

The integer r in general formulae (VIIa), (VIIb), and (VIIc) is in the range of 2 to 6.

Surfactants may further be compounds comprising amphoteric structures of general formula (VIII), which might be called alkyl-amphocarboxylates:

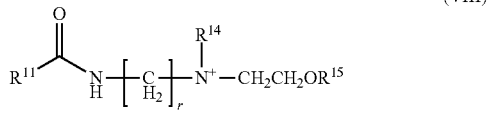

(VIII)

The variables in general formula (VIII) are defined as follows:

$R^{11}$ is selected from $C_7$-$C_{22}$ alkyl and $C_7$-$C_{22}$ alkenyl, wherein alkyl and/or alkenyl are linear or branched, preferably linear.

$R^{14}$ is selected from $-CH_2C(O)O^-M+$, $-CH_2CH_2C(O)O^-M^+$ and $-CH_2CH(OH)CH_2SO_3^-M^+$.

$R^{15}$ is selected from H and $-CH_2C(O)O^-$.

The integer r in general formula (VIII) is in the range of 2 to 6.

Non-limiting examples of further suitable alkyl-amphocarboxylates include sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

Surfactants may further be compounds comprising amphoteric structures of general formula (IX), which might be called amine oxides (AO):

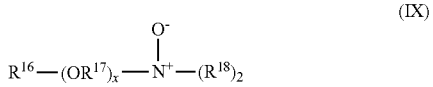

(IX)

The variables in general formula (IX) are defined as follows:

$R^{16}$ is selected from $C_8$-$C_{18}$ linear or branched alkyl, hydroxy $C_8$-$C_{18}$ alkyl, acylamidopropoyl and $C_8$-$C_{18}$ alkyl phenyl group; wherein alkyl and/or alkenyl are linear or branched.

$R^{17}$ is selected from $C_2$-$C_3$ alkylene, hydroxy $C_2$-$C_3$ alkylene, and mixtures thereof.

$R^{18}$: each residue can be independently selected from $C_1$-$C_3$ alkyl and hydroxy $C_1$-$C_3$; $R^{18}$ groups can be attached to each other, e.g., through an oxygen or nitrogen atom, to form a ring structure.

The integer x in general formula (IX) is in the range of 0 to 5, preferably from 0 to 3, most preferably 0.

Non-limiting examples of further suitable amine oxides include $C_{10}$-$C_{18}$ alkyl dimethyl amine oxides and $C_8$-$C_{18}$ alkoxy ethyl dihydroxyethyl amine oxides. Examples of such materials include dimethyloctyl amine oxide, diethyldecyl amine oxide, bis-(2-hydroxyethyl)dodecyl amine oxide, dimethyldodecylamine oxide, dipropyltetradecyl amine oxide, methylethylhexadecyl amine oxide, dodecylamidopropyl dimethyl amine oxide, cetyl dimethyl amine oxide, stearyl dimethyl amine oxide, tallow dimethyl amine oxide and dimethyl-2-hydroxyoctadecyl amine oxide.

A further example of a suitable amine oxide is cocamidylpropyl dimethylaminoxide, sometimes also called cocamidopropylamine oxide.

Mixtures of two or more different amphoteric surfactants may be present in detergent formulations according to the present invention.

Anionic surfactant means a surfactant with a negatively charged ionic group. Anionic surfactants include, but are not limited to, surface-active compounds that contain a hydrophobic group and at least one water-solubilizing anionic group, usually selected from sulfates, sulfonate, and carboxylates to form a water-soluble compound.

Anionic surfactants may be compounds of general formula (X), which might be called (fatty) alcohol/alkyl (ethoxy/ether) sulfates [(F)A(E)S] when $A^-$ is $SO_3^-$, (fatty) alcohol/alkyl (ethoxy/ether) carboxylat [(F)A(E)C] when $A^-$ is $-RCOO^-$:

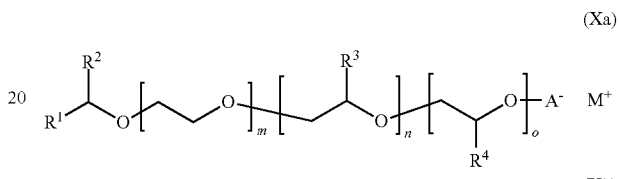

(Xa)

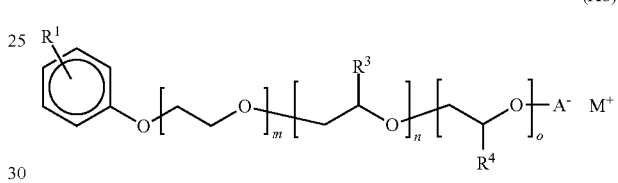

(Xb)

The variables in general formulae (Xa and Xb) are defined as follows:

$R^1$ is selected from $C_1$-$C_{23}$-alkyl (such as 1-, 2-, 3-, 4-$C_1$-$C_{23}$-alkyl) and $C_2$-$C_{23}$-alkenyl, wherein alkyl and/or alkenyl are linear or branched, and wherein 2-, 3-, or 4-alkyl; examples are n-$C_7H_{15}$, n-$C_9H_{19}$, n-$C_{11}H_{23}$, n-$C_{13}H_{27}$, n-$C_{15}H_{31}$, n-$C_{17}H_{35}$, i-$C_9H_{19}$, i-$C_{12}H_{25}$.

$R^2$ is selected from H, $C_1$-$C_{20}$-alkyl and $C_2$-$C_{20}$-alkenyl, wherein alkyl and/or alkenyl are linear or branched.

$R^3$ and $R^4$, each independently selected from $C_1$-$C_{16}$-alkyl, wherein alkyl is linear or branched; examples are methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl.

$A^-$ is selected from $-RCOO^-$, $-SO_3^-$ and $RSO_3^-$, wherein R is selected from linear or branched $C_1$-$C_8$-alkyl, and $C_1$-$C_4$ hydroxyalkyl, wherein alkyl is.

$M^+$ is selected from H and salt forming cations. Salt forming cations may be monovalent or multivalent; hence $M^+$ equals $1/v\ M^{v+}$. Examples include but are not limited to sodium, potassium, magnesium, calcium, ammonium, and the ammonium salt of mono-, di, and triethanolamine.

The integers of the general formulae (Xa) and (VIIIXb) are defined as follows: m is in the range of zero to 200, preferably 1-80, more preferably 3-20; n and o, each independently in the range of zero to 100; n preferably is in the range of 1 to 10, more preferably 1 to 6; o preferably is in the range of 1 to 50, more preferably 4 to 25. The sum of m, n and o is at least one, preferably the sum of m, n and o is in the range of 5 to 100, more preferably in the range of from 9 to 50. Anionic surfactants of the general formula (Xa) and (Xb) may be of any structure, block copolymers or random copolymers.

Further suitable anionic surfactants include salts ($M^+$) of $C_{12}$-$C_{18}$ sulfo fatty acid alkyl esters (such as $C_{12}$-$C_{18}$ sulfo fatty acid methyl esters), $C_{10}$-$C_{18}$-alkylarylsulfonic acids (such as n-$C_{10}$-$C_{18}$-alkylbenzene sulfonic acids) and $C_{10}$-$C_{18}$ alkyl alkoxy carboxylates.

$M^+$ in all cases is selected from salt forming cations. Salt forming cations may be monovalent or multivalent; hence $M^+$ equals $1/v\ M^{v+}$. Examples include but are not limited to sodium, potassium, magnesium, calcium, ammonium, and the ammonium salt of mono-, di, and triethanolamine.

In one embodiment, the detergent formulation comprises at least one anionic surfactant selected from compounds of general formula (Xa), wherein $R^1$ is $C_{11}$-$C_{13}$, $R^2$ is H, m is 1-4, n and o=0, $A^-$ is $SO_3^-$, $M^+$ is $Na^+$. The detergent formulation may comprise at least two anionic surfactants, selected from compounds of general formula (Xa), wherein one of said anionic surfactants is characterized in $R^1$ being $C_{11}$, $R^2$ being H, m being 2, n and o=0, $A^-$ being $SO_3^-$, $M^+$ being $Na^+$ and the other surfactant is characterized in $R^1$ being $C_{13}$, $R^2$ being H, m being 2, n and o=0, $A^-$ being $SO_3^-$, $M^+$ being $Na^+$.

Non-limiting examples of further suitable anionic surfactants include branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, secondary alkanesulfonates (SAS), paraffin sulfonates (PS), sulfonated fatty acid glycerol esters, alkyl- or alkenylsuccinic acid, fatty acid derivatives of amino acids, diesters and monoesters of sulfo-succinic acid.

In one embodiment, the detergent formulation comprises at least one anionic surfactant selected from compounds of general formula (XI):

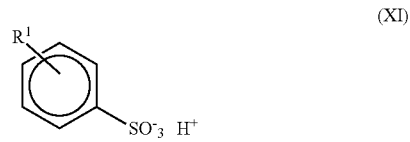

(XI)

wherein $R^1$ in formula (XI) is $C_{10}$-$C_{13}$ alkyl. The detergent formulation may comprise at least two anionic surfactants, selected from compounds of general formula (XI), wherein one of said anionic surfactants is characterized in $R^1$ being $C_{10}$, and the other surfactant is characterized in $R^1$ being $C_{13}$.

Anionic surfactants may be compounds of general formula (XII), which might be called N-acyl amino acid surfactants:

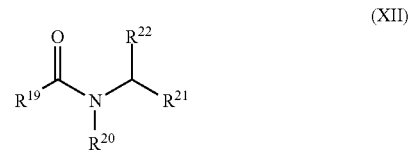

(XII)

The variables in general formula (XII) are defined as follows:

$R^{19}$ is selected from linear or branched $C_6$-$C_{22}$-alkyl and linear or branched $C_6$-$C_{22}$-alkenyl such as oleyl.

$R^{20}$ is selected from H and $C_1$-$C_4$-alkyl.

$R^{21}$ is selected from H, methyl, —$(CH_2)_3$NHC(NH)$NH_2$, —$CH_2$C(O)$NH_2$, —$CH_2$C(O)OH, —$(CH_2)_2$C(O)$NH_2$, —$(CH_2)_2$C(O)OH, (imidazole-4-yl)-methyl, —CH($CH_3$)$C_2H_5$, —$CH_2$CH($CH_3$)$_2$, —$(CH_2)_4$$NH_2$, benzyl, hydroxymethyl, —CH(OH)$CH_3$, (indole-3-yl)-methyl, (4-hydroxyphenyl)-methyl, isopropyl, —$(CH_2)_2$$SCH_3$, and —$CH_2$SH.

$R^{22}$ is selected from —COOX and —$CH_2SO_3X$, wherein X is selected from $Li^+$, $Na^+$ and $K^+$.

Non-limiting examples of suitable N-acyl amino acid surfactants are the mono- and di-carboxylate salts (e.g., sodium, potassium, ammonium and ammonium salt of mono-, di, and triethanolamine) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and ammonium salt of mono-, di, and triethanolamine) of N-acylated alanine, for example, sodium cocoyl alaninate, and triethanolamine lauroyl alaninate; the carboxylate salts (e.g., sodium, potassium, ammonium and ammonium salt of mono-, di, and triethanolamine) of N-acylated glycine, for example, sodium cocoyl glycinate, and potassium cocoyl glycinate; the carboxylate salts (e.g., sodium, potassium, ammonium and ammonium salt of mono-, di, and triethanolamine) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate.

Anionic surfactants may further be selected from the group of soaps. Suitable are salts ($M^+$) of saturated and unsaturated $C_{12}$-$C_{18}$ fatty acids, such as lauric acid, myristic acid, palmitic acid, stearic acid, behenic acid, oleic acid, (hydrated) erucic acid. $M^+$ is selected from salt forming cations. Salt forming cations may be monovalent or multivalent; hence $M^+$ equals $1/v\ M^{v+}$. Examples include but are not limited to sodium, potassium, magnesium, calcium, ammonium, and the ammonium salt of mono-, di, and triethanolamine.

Further non-limiting examples of suitable soaps include soap mixtures derived from natural fatty acids such as tallow, coconut oil, palm kernel oil, laurel oil, olive oil, or canola oil. Such soap mixtures comprise soaps of lauric acid and/or myristic acid and/or palmitic acid and/or stearic acid and/or oleic acid and/or linoleic acid in different amounts, depending on the natural fatty acids from which the soaps are derived.

Further non-limiting examples of suitable anionic surfactants include salts ($M^+$) of sulfates, sulfonates or carboxylates derived from natural fatty acids such as tallow, coconut oil, palm kernel oil, laurel oil, olive oil, or canola oil. Such anionic surfactants comprise sulfates, sulfonates or carboxylates of lauric acid and/or myristic acid and/or palmitic acid and/or stearic acid and/or oleic acid and/or linoleic acid in different amounts, depending on the natural fatty acids from which the soaps are derived.

Mixtures of two or more different anionic surfactants may also be present in detergent formulations according to the present invention.

Mixtures of non-ionic and/or amphoteric and/or anionic surfactants may also be present in detergent formulations according to the present invention.

Cationic surfactant means a surfactant with a positively charged ionic group.

Typically, these cationic moieties are nitrogen containing groups such as quaternary ammonium or protonated amino groups. The cationic protonated amines can be primary, secondary, or tertiary amines.

Cationic surfactants may be compounds of the general formula (XIII) which might be called quaternary ammonium compounds (quats):

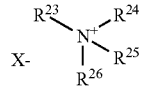

(XIII)

The variables in general formula (XIII) are defined as follows:

$R^{23}$ is selected from H, $C_1$-$C_4$ alkyl (such as methyl) and $C_2$-$C_4$ alkenyl, wherein alkyl and/or alkenyl is linear or branched.

$R^{24}$ is selected from $C_1$-$C_4$ alkyl (such as methyl), $C_2$-$C_4$ alkenyl and $C_1$-$C_4$ hydroxyalkyl (such as hydroxyethyl), wherein alkyl and/or alkenyl is linear or branched.

$R^{25}$ is selected from $C_1$-$C_{22}$ alkyl (such as methyl, $C_{18}$ alkyl), $C_2$-$C_4$ alkenyl, $C_{12}$-$C_{22}$ alkylcarbonyloxymethyl and $C_{12}$-$C_{22}$ alkylcarbonyloxyethyl (such as $C_{16}$-$C_{18}$ alkylcarbonyloxyethyl), wherein alkyl and/or alkenyl is linear or branched.

$R^{26}$ is selected from $C_{12}$-$C_{18}$ alkyl, $C_2$-$C_4$ alkenyl, $C_{12}$-$C_{22}$ alkylcarbonyloxymethyl, $C_{12}$-$C_{22}$ alkylcarbonyloxyethyl and 3-($C_{12}$-$C_{22}$ alkylcarbonyloxy)-2($C12$-$C_{22}$ alkylcarbonyloxy)-propyl.

$X^-$ is selected from halogenid, such as $Cl^-$ or $Br^-$.

Non-limiting examples of further cationic surfactants include, amines such as primary, secondary and tertiary monoamines with $C_{18}$ alkyl or alkenyl chains, ethoxylated alkylamines, alkoxylates of ethylenediamine, imidazoles (such as 1-(2-hydroxyethyl)-2-imidazoline, 2-alkyl-1-(2-hydroxyethyl)-2-imidazoline, and the like), quaternary ammonium salts like alkylquaternary ammonium chloride surfactants such as n-alkyl($C_{12}$-$C_{18}$)dimethylbenzyl ammonium chloride, n-tetradecyldimethylbenzylammonium chloride monohydrate, and a naphthylene-substituted quaternary ammonium chloride such as dimethyl-1-naphthylmethylammonium chloride.

Particularly suitable cationic surfactants that may be:

N,N-dimethyl-N-(hydroxy-$C_7$-$C_{25}$-alkyl)ammonium salts;

mono- and di($C_7$-$C_{25}$-alkyl)dimethylammonium compounds quaternized with alkylating agents;

ester quats, in particular quaternary esterified mono-, di- and trialkanolamines which are esterified with $C_8$-$C_{22}$-carboxylic acids;

imidazoline quats, in particular 1-alkylimidazolinium salts of formulae XIV or XV

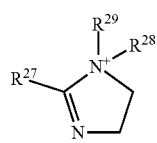

(XIV)

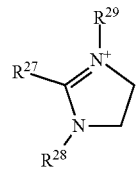

(XV)

The variables in formulae (XIV) and (XV) are defined as follows:

$R^{27}$ is selected from $C_1$-$C_{25}$-alkyl and $C_2$-$C_{25}$-alkenyl;

$R^{28}$ is selected from $C_1$-$C_4$-alkyl and hydroxy-$C_1$-$C_4$-alkyl;

$R^{29}$ is selected from $C_1$-$C_4$-alkyl, hydroxy-$C_1$-$C_4$-alkyl and a $R^*$—(CO)—$R^{30}$—($CH_2$)j-radical, wherein $R^*$ is selected from $C_1$-$C_{21}$-alkyl and $C_2$-$C_{21}$-alkenyl; $R^{30}$ is selected from —$O^-$ and —$NH^-$; j is 2 or 3.

The detergent formulation may comprise a mixture of surfactants selected from compounds of general formula (IIIa), compounds of general formula (Xa), and compounds of general formula (XI).

Example 1: Variant Lipase Enzymes

Non-naturally occurring variant lipase enzymes were created in a lab using rational design single site mutagenesis and multisite mutagenesis. The variant lipase enzymes include single point amino acid modifications, insertions, or deletions of a parent enzyme (LIP062, which is the amino acid sequence of SEQ ID 1, and is encoded by nucleic acid sequence of SEQ ID NO:2) at 18 different amino acid residue positions: 23, 33, 82, 83, 84, 85, 160, 199, 254, 255, 256, 258, 263, 264, 265, 268, 308, 311, or any combination thereof, wherein the variant lipase enzymes has lipase activity.

Variant lipase enzymes were also created with various combinations of the single point modifications of a parent enzyme (LIP062), wherein the variant lipase enzymes have lipase activity. For example, the single point modifications and various combinations of single point modifications are listed in Table: 1.

The table shows a variant lipase enzyme of LIP110, which is a variant polypeptide having the amino acid sequence of LIP062 and one amino acid substitution of D265S, wherein the variant polypeptide has lipase activity. This table also shows a variant lipase enzyme of LIP160, which is a variant polypeptide having an amino acid sequence of LIP062 and a combination of amino acid substitutions of S83H, I85L, and D265T, wherein the variant polypeptide has lipase activity. This table also shows a variant lipase enzyme of LIP173, which is a variant polypeptide having an amino acid sequence of LIP062 and a combination of amino acid substitutions of I255A, and D265S, wherein the variant polypeptide has lipase activity. Table 1, also shows lipase variants of the parent lipase, wherein the variant includes an insertion of an amino acid residue. The insertion of an amino acid residue is shown as ('), for example (84')

TABLE 1

| Lipase | Amino Acid Residue Position Numbers | | | | | | | | | | | | | | | | | | |
|---|---|---|---|---|---|---|---|---|---|---|---|---|---|---|---|---|---|---|---|
| | 23 | 33 | 82 | 83 | 84 | 84' | 85 | 160 | 199 | 254 | 255 | 256 | 258 | 263 | 264 | 265 | 268 | 308 | 311 |
| LIP062 | Y | K | S | S | N | – | I | K | P | I | I | A | L | D | T | D | T | D | Y |
| LIP182 | – | – | – | H | – | – | S | – | – | – | A | – | – | – | A | T | – | – | – |
| LIP181 | – | – | – | H | – | – | V | – | – | – | A | – | – | – | S | T | – | – | – |

TABLE 1-continued

| Lipase | Amino Acid Residue Position Numbers ||||||||||||||||||||
|---|---|---|---|---|---|---|---|---|---|---|---|---|---|---|---|---|---|---|---|
| LIP062 | 23 | 33 | 82 | 83 | 84 | 84' | 85 | 160 | 199 | 254 | 255 | 256 | 258 | 263 | 264 | 265 | 268 | 308 | 311 |
|  | Y | K | S | S | N | — | I | K | P | I | I | A | L | D | T | D | T | D | Y |
| LIP180 | — | — | — | T | — | — | H | — | — | — | A | — | — | — | — | A | — | — | — |
| LIP179 | — | — | — | — | — | — | V | — | — | — | A | — | — | — | S | T | — | — | — |
| LIP178 | — | — | — | H | — | — | L | — | — | — | A | — | — | — | S | A | — | — | — |
| LIP177 | — | — | — | H | — | — | T | — | — | — | A | — | — | — | — | T | — | — | — |
| LIP176 | — | — | — | Y | — | — | A | — | — | — | A | — | — | — | — | T | — | — | — |
| LIP175 | — | — | — | T | — | — | B | — | — | — | A | — | — | — | — | S | — | — | — |
| LIP174 | — | — | — | — | — | — | — | — | — | — | A | — | — | — | — | A | — | — | — |
| LIP173 | — | — | — | — | — | — | — | — | — | — | A | — | — | — | — | S | — | — | — |
| LIP172 | — | — | — | N | — | — | L | — | — | — | A | — | — | — | N | T | — | — | — |
| LIP171 | — | — | — | — | — | — | — | — | — | — | A | — | — | — | D | T | — | — | — |
| LIP170 | — | — | — | N | — | — | L | — | — | — | A | — | — | — | — | T | — | — | — |
| LIP169 | — | — | — | N | — | — | V | — | — | L | — | — | — | — | S | T | — | — | — |
| LIP168 | — | — | — | H | — | — | — | — | — | L | — | — | — | — | A | A | — | — | — |
| LIP167 | — | — | — | H | — | — | — | — | — | L | — | — | — | — | — | T | — | — | — |
| LIP166 | — | — | — | — | — | — | V | — | — | L | — | — | — | — | D | T | — | — | — |
| LIP165 | — | — | — | Y | — | — | — | — | — | — | — | — | — | — | A | T | — | — | — |
| LIP164 | — | — | — | — | — | — | V | — | — | — | — | — | — | — | D | T | — | — | — |
| LIP163 | — | — | — | Y | — | — | A | — | — | — | — | — | — | — | A | T | — | — | — |
| LIP162 | — | — | — | N | — | — | V | — | — | — | — | — | — | — | N | T | — | — | — |
| LIP161 | — | — | — | N | — | — | — | — | — | — | — | — | — | — | D | T | — | — | — |
| LIP160 | — | — | — | H | — | — | L | — | — | — | — | — | — | — | — | T | — | — | — |
| LIP159 | — | — | — | H | — | — | A | — | — | — | — | — | — | — | A | T | — | — | — |
| LIP158 | — | — | — | T | — | — | V | — | — | — | — | — | — | — | — | T | — | — | — |
| LIP157 | — | — | — | H | — | — | L | — | — | — | — | — | — | — | — | A | — | — | — |
| LIP156 | — | — | — | H | — | — | V | — | — | — | — | — | — | — | — | A | — | — | — |
| LIP155 | — | — | — | T | — | — | A | — | — | — | — | — | — | — | — | T | — | — | — |
| LIP154 | — | — | — | H | — | — | V | — | — | — | — | — | — | — | N | T | — | — | — |
| LIP153 | — | — | — | — | — | — | V | — | — | — | — | — | — | — | — | G | — | — | — |
| LIP152 | — | — | — | H | — | — | — | — | — | — | — | — | — | — | — | A | — | — | — |
| LIP151 | — | — | — | Y | — | — | V | — | — | — | — | — | — | — | S | S | — | — | — |
| LIP150 | — | — | — | N | — | — | V | — | — | — | — | — | — | — | — | G | — | — | — |
| LIP149 | — | — | — | H | — | — | — | — | — | — | — | — | — | — | — | S | — | — | — |
| LIP148 | — | — | — | H | — | — | — | — | — | — | — | — | — | — | — | G | — | — | — |
| LIP147 | — | — | — | H | — | — | — | — | — | — | — | — | — | — | S | G | — | — | — |
| LIP146 | — | — | — | H | — | — | — | — | — | — | — | — | — | — | G | G | — | — | — |
| LIP145 | — | — | — | — | — | — | — | — | — | A | — | — | — | — | S | G | — | — | — |
| LIP144 | — | — | — | H | — | — | — | — | — | A | — | — | — | — | — | G | — | — | — |

TABLE 1-continued

| Lipase | 23 | 33 | 82 | 83 | 84 | 84' | 85 | 160 | 199 | 254 | 255 | 256 | 258 | 263 | 264 | 265 | 268 | 308 | 311 |
|---|---|---|---|---|---|---|---|---|---|---|---|---|---|---|---|---|---|---|---|
| LIP062 | Y | K | S | S | N | – | I | K | P | I | I | A | L | D | T | D | T | D | Y |
| LIP143 | – | – | – | H | – | – | – | – | – | – | A | – | – | – | – | S | G | – | – |
| LIP142 | – | – | – | H | – | – | – | – | – | – | A | – | – | – | – | G | G | – | – |
| LIP135 | – | – | – | – | – | – | – | – | – | – | L | – | – | – | – | – | – | – | – |
| LIP134 | – | – | – | – | – | – | – | – | – | – | A | – | – | – | – | – | – | – | – |
| LIP131 | – | – | – | I | – | – | L | – | – | – | – | – | – | – | – | S | – | – | – |
| LIP130 | – | – | – | I | – | – | L | – | – | – | – | – | – | – | – | S | – | – | – |
| LIP126 | – | – | – | – | – | – | – | – | – | – | – | – | – | R | – | – | – | – | – |
| LIP124 | – | – | – | – | – | – | T | – | – | – | – | – | – | – | – | G | G | – | – |
| LIP123 | – | – | – | – | – | – | L | – | – | – | – | – | – | – | – | G | G | – | – |
| LIP120 | – | – | – | H | – | – | H | – | – | – | – | – | – | – | – | – | G | – | – |
| LIP119 | – | – | – | – | – | – | T | – | – | – | – | – | – | – | – | S | G | – | – |
| LIP118 | – | – | – | H | – | – | L | – | – | – | – | – | – | – | – | G | – | – | – |
| LIP117 | – | – | – | H | – | – | T | – | – | – | – | – | – | – | – | S | G | – | – |
| LIP116 | – | – | – | H | – | – | L | – | – | – | – | – | – | – | – | G | G | – | – |
| LIP115 | – | – | – | H | – | – | L | – | – | – | – | – | – | – | – | S | G | – | – |
| LIP114 | – | – | – | H | – | – | L | – | – | – | – | – | – | – | – | S | – | – | – |
| LIP113 | – | – | – | – | – | – | L | – | – | – | – | – | – | – | – | S | G | – | – |
| LIP111 | – | – | – | – | – | – | – | – | – | – | – | – | – | – | – | A | – | – | – |
| LIP110 | – | – | – | – | – | – | – | – | – | – | – | – | – | – | – | S | – | – | – |
| LIP109 | – | – | – | – | – | – | – | – | – | – | – | – | – | – | – | G | – | – | – |
| LIP108 | – | – | – | H | – | – | – | – | – | – | – | – | – | – | – | – | – | – | – |
| LIP102 | – | – | – | – | – | – | T | – | – | – | – | – | – | – | – | – | – | – | – |
| LIP101 | – | – | – | – | – | – | P | – | – | – | – | – | – | – | – | – | – | – | – |
| LIP100 | – | – | – | – | – | – | L | – | – | – | – | – | – | – | – | – | – | – | – |
| LIP099 | – | – | – | – | – | – | A | – | – | – | – | – | – | – | – | – | – | – | – |
| LIP096 | – | – | – | – | – | – | – | – | – | – | – | – | D | – | – | – | – | – | – |
| LIP095 | – | – | – | – | – | – | – | N | – | – | – | – | – | – | – | – | – | – | – |
| LIP094 | – | N | – | – | – | – | – | – | – | – | – | – | – | – | – | – | – | – | – |
| LIP090 | – | – | – | – | – | – | – | – | V | – | – | – | – | – | – | – | – | – | – |
| LIP089 | – | – | T | – | – | – | – | – | – | – | – | – | – | – | – | – | – | – | – |
| LIP062_1909 | – | – | – | – | – | – | T | – | – | – | A | – | – | – | – | – | – | – | – |
| LIP062_1908 | – | – | – | H | – | – | T | – | – | – | A | – | – | – | – | – | – | – | – |
| LIP062_1907 | – | – | – | – | – | – | P | – | – | – | A | – | – | – | – | S | – | – | – |
| LIP062_1906 | – | – | – | H | – | – | P | – | – | – | A | – | – | – | – | – | – | – | – |
| LIP062_1905 | – | – | – | I | – | – | – | – | – | – | A | – | – | – | – | G | G | – | – |
| LIP062_1904 | – | – | – | – | – | – | – | – | – | – | A | – | – | – | – | G | G | – | – |
| LIP062_1903 | – | – | – | H | – | – | P | – | – | – | – | – | – | – | – | – | G | – | – |
| LIP062_1902 | – | – | – | – | – | – | P | – | – | – | – | – | – | – | – | S | G | – | – |

TABLE 1-continued

| Lipase | 23 | 33 | 82 | 83 | 84 | 84' | 85 | 160 | 199 | 254 | 255 | 256 | 258 | 263 | 264 | 265 | 268 | 308 | 311 |
|---|---|---|---|---|---|---|---|---|---|---|---|---|---|---|---|---|---|---|---|
| LIP062 | Y | K | S | S | N | — | I | K | P | I | I | A | L | D | T | D | T | D | Y |
| LIP062_1901 | — | — | — | — | — | — | T | — | — | — | — | — | — | — | — | S | — | — | — |
| LIP062_1900 | — | — | H | — | — | — | T | — | — | — | — | — | — | — | — | — | — | — | — |
| LIP062_1899 | — | — | — | — | — | — | P | — | — | — | — | — | — | — | — | S | — | — | — |
| LIP062_1898 | — | — | H | — | — | — | P | — | — | — | — | — | — | — | — | — | — | — | — |
| LIP062_1897 | — | — | I | — | — | — | — | — | — | — | — | — | — | — | — | G | — | — | — |
| LIP062_1896 | — | — | — | — | — | — | — | — | — | — | — | — | — | — | — | S | G | — | — |
| LIP062_1895 | — | — | I | — | — | — | — | — | — | — | — | — | — | — | — | G | G | — | — |
| LIP062_1894 | — | — | — | — | — | — | — | — | — | — | — | — | — | — | — | G | G | — | — |
| LIP062_1893 | — | — | I | — | — | — | T | — | — | — | — | — | — | — | — | G | — | — | — |
| LIP062_1892 | — | — | H | — | — | — | T | — | — | — | — | — | — | — | — | G | — | — | — |
| LIP062_1891 | — | — | I | — | — | — | T | — | — | — | — | — | — | — | — | S | — | — | — |
| LIP062_1890 | — | — | I | — | — | — | T | — | — | — | — | — | — | — | — | G | — | — | — |
| LIP062_1889 | — | — | H | — | — | — | T | — | — | — | — | — | — | — | — | S | — | — | — |
| LIP062_1888 | — | — | H | — | — | — | T | — | — | — | — | — | — | — | — | G | — | — | — |
| LIP062_1887 | — | — | I | — | — | — | L | — | — | — | — | — | — | — | — | G | — | — | — |
| LIP062_1886 | — | — | I | — | — | — | T | — | — | — | — | — | — | — | — | S | G | — | — |
| LIP062_1885 | — | — | I | — | — | — | L | — | — | — | — | — | — | — | — | S | G | — | — |
| LIP062_1884 | — | — | I | — | — | — | T | — | — | — | — | — | — | — | — | G | G | — | — |
| LIP062_1883 | — | — | I | — | — | — | L | — | — | — | — | — | — | — | — | G | G | — | — |
| LIP062_1882 | — | — | H | — | — | — | T | — | — | — | — | — | — | — | — | G | G | — | — |
| LIP062_1881 | — | — | — | — | — | — | — | — | — | — | — | — | — | I | — | — | — | — | — |
| LIP062_1880 | — | — | — | — | — | — | — | — | — | — | — | — | — | L | — | — | — | — | — |
| LIP062_1879 | — | — | — | — | — | — | — | — | — | — | — | — | — | P | — | — | — | — | — |
| LIP062_1878 | — | — | — | — | — | — | — | — | — | — | — | — | — | G | — | — | — | — | — |
| LIP062_1877 | — | — | — | — | — | — | — | — | — | — | — | — | — | S | — | — | — | — | — |
| LIP062_1876 | — | — | — | — | — | — | — | — | — | — | — | — | — | K | — | — | — | — | — |
| LIP062_1875 | — | — | I | N | — | — | V | — | — | — | — | — | — | — | — | — | — | — | — |
| LIP062_1874 | — | — | R | S | — | — | V | — | — | — | — | — | — | — | — | — | — | — | — |
| LIP062_1873 | — | — | — | — | — | — | — | — | — | — | — | — | — | — | — | L | — | — | — |
| LIP062_1872 | — | — | — | — | — | — | — | — | — | — | — | — | — | — | — | A | — | — | — |
| LIP062_1871 | — | — | — | — | — | — | — | — | — | — | — | — | — | — | — | N | — | — | — |
| LIP062_1870 | — | — | — | — | — | — | — | — | — | — | — | — | — | — | — | K | — | — | — |
| LIP062_1869 | — | — | — | — | — | — | — | — | — | — | — | — | — | — | — | S | — | — | — |
| LIP062_1868 | — | — | — | — | — | — | — | — | — | — | — | — | — | — | — | G | — | — | — |
| LIP062_1867 | — | — | — | — | — | — | — | — | — | — | — | — | — | — | — | L | — | — | — |
| LIP062_1866 | — | — | — | — | — | — | — | — | — | — | — | — | — | — | — | N | — | — | — |
| LIP062_1865 | — | — | — | — | — | — | — | — | — | — | — | — | — | — | — | K | — | — | — |

TABLE 1-continued

| Lipase | Amino Acid Residue Position Numbers | | | | | | | | | | | | | | | | | | |
|---|---|---|---|---|---|---|---|---|---|---|---|---|---|---|---|---|---|---|---|
| LIP062 | 23 Y | 33 K | 82 S | 83 S | 84 N | 84' – | 85 I | 160 K | 199 P | 254 I | 255 I | 256 A | 258 L | 263 D | 264 T | 265 D | 268 T | 308 D | 311 Y |
| LIP062_1864 | – | – | – | N | – | – | – | – | – | – | – | – | – | – | – | – | – | – | – |
| LIP062_1863 | – | – | – | D | – | – | – | – | – | – | – | – | – | – | – | – | – | – | – |
| LIP062_1862 | – | – | – | I | – | – | – | – | – | – | – | – | – | – | – | – | – | – | – |
| LIP062_1861 | A | – | – | – | – | – | – | – | – | – | – | – | – | – | – | – | – | – | – |
| LIP062_1860 | – | – | – | – | – | – | – | – | – | – | – | – | – | – | – | – | – | A | E |
| LIP062_1859 | – | – | – | – | – | – | – | – | – | – | – | – | – | – | – | – | – | A | – |
| LIP062_1858 | – | – | – | – | – | – | – | – | – | – | – | – | – | – | – | – | – | – | E |
| LIP062_1857 | – | – | – | – | S | – | – | – | – | – | – | – | – | – | – | – | – | – | – |
| LIP062_1856 | – | – | – | – | L | – | – | – | – | – | – | – | – | – | – | – | – | – | – |
| LIP062_1855 | – | – | – | – | Y | – | – | – | – | – | – | – | – | – | – | – | – | – | – |
| LIP062_1854 | – | – | – | – | – | – | – | – | – | – | – | – | E | – | – | – | – | – | – |
| LIP062_1853 | – | – | – | – | – | – | – | – | – | – | – | – | Q | – | – | – | – | – | – |
| LIP062_1852 | – | – | – | – | – | – | – | – | – | – | – | – | T | – | – | – | – | – | – |
| LIP062_1851 | – | – | – | – | – | – | – | – | – | – | – | – | H | – | – | – | – | – | – |
| LIP062_1850 | – | – | – | – | – | – | – | – | – | – | – | – | D | – | – | – | – | – | – |
| LIP062_1849 | – | – | – | – | – | – | – | – | – | – | – | – | V | – | – | – | – | – | – |
| LIP062_1848 | – | – | – | – | – | – | – | – | – | – | – | – | R | – | – | – | – | – | – |
| LIP062_1847 | – | – | – | – | – | – | – | – | – | – | – | – | N | – | – | – | – | – | – |
| LIP062_1846 | – | – | – | – | – | – | – | – | – | – | – | – | G | – | – | – | – | – | – |
| LIP062_1845 | – | – | – | – | – | – | – | – | – | – | – | – | A | – | – | – | – | – | – |
| LIP062_1844 | – | – | – | – | – | – | – | – | – | – | – | – | S | – | – | – | – | – | – |
| LIP062_1843 | – | – | – | – | – | – | – | – | – | M | – | – | – | – | – | – | – | – | – |
| LIP062_1842 | – | – | – | – | – | – | – | – | – | G | – | – | – | – | – | – | – | – | – |
| LIP062_1841 | – | – | – | – | – | – | – | – | – | R | – | – | – | – | – | – | – | – | – |
| LIP062_1840 | – | – | – | – | – | – | – | – | – | F | – | – | – | – | – | – | – | – | – |
| LIP062_1839 | – | – | – | – | – | – | – | – | – | E | – | – | – | – | – | – | – | – | – |
| LIP062_1838 | – | – | – | – | – | – | – | – | – | W | – | – | – | – | – | – | – | – | – |
| LIP062_1837 | – | – | – | – | – | – | – | – | – | L | – | – | – | – | – | – | – | – | – |
| LIP062_1836 | – | – | – | – | – | – | – | – | – | Y | – | – | – | – | – | – | – | – | – |
| LIP062_1835 | – | – | – | – | – | – | – | – | – | S | – | – | – | – | – | – | – | – | – |
| LIP062_1834 | – | – | – | – | – | – | – | – | – | C | – | – | – | – | – | – | – | – | – |
| LIP062_1833 | – | – | – | – | – | – | – | – | – | A | – | – | – | – | – | – | – | – | – |
| LIP062_1832 | – | – | – | – | – | – | – | – | – | V | – | – | – | – | – | – | – | – | – |
| LIP062_1831 | – | – | – | – | – | – | – | – | – | N | – | – | – | – | – | – | – | – | – |
| LIP062_1830 | – | – | – | – | – | – | M | – | – | – | – | – | – | – | – | – | – | – | – |
| LIP062_1829 | – | – | – | – | – | – | S | – | – | – | – | – | – | – | – | – | – | – | – |
| LIP062_1828 | – | – | – | – | – | – | C | – | – | – | – | – | – | – | – | – | – | – | – |
| LIP062_1827 | – | N | – | – | – | – | – | N | – | – | – | – | – | – | – | – | – | – | – |

TABLE 1-continued

| Lipase | \multicolumn{19}{c|}{Amino Acid Residue Position Numbers} |
| --- | --- | --- | --- | --- | --- | --- | --- | --- | --- | --- | --- | --- | --- | --- | --- | --- | --- | --- | --- |
| LIP062 | 23 Y | 33 K | 82 S | 83 S | 84 N | 84' – | 85 I | 160 K | 199 P | 254 I | 255 I | 256 A | 258 L | 263 D | 264 T | 265 D | 268 T | 308 D | 311 Y |
| LIP062_1826 | – | – | – | – | – | – | – | – | I | – | – | – | – | – | – | – | – | – | – |
| LIP062_1825 | – | – | N | – | – | V | – | – | – | A | – | – | – | – | A | G | – | – | – |
| LIP062_1824 | – | – | T | – | – | V | – | – | – | A | – | – | – | – | – | G | – | – | – |
| LIP062_1823 | – | – | N | – | – | V | – | – | – | A | – | – | – | – | S | S | – | – | – |
| LIP062_1822 | – | – | H | – | – | T | – | – | – | A | – | – | – | – | S | S | – | – | – |
| LIP062_1820 | – | – | – | – | – | – | – | – | – | A | – | – | – | – | A | T | – | – | – |
| LIP062_1818 | – | – | Y | – | – | – | – | – | – | A | – | – | – | – | – | T | – | – | – |
| LIP062_1817 | – | – | – | – | – | – | – | – | – | A | – | – | – | – | G | T | – | – | – |
| LIP062_1816 | – | – | – | – | – | – | – | – | – | A | – | – | – | – | N | A | – | – | – |
| LIP062_1814 | – | – | T | – | – | A | – | – | – | A | – | – | – | – | – | T | – | – | – |
| LIP062_1812 | – | – | N | – | – | – | – | – | – | A | – | – | – | – | – | A | – | – | – |
| LIP062_1810 | – | – | T | – | – | – | – | – | – | A | – | – | – | – | N | T | – | – | – |
| LIP062_1807 | – | – | – | – | – | – | – | – | – | A | – | – | – | – | D | A | – | – | – |
| LIP062_1805 | – | – | H | – | – | V | – | – | – | A | – | – | – | – | – | A | – | – | – |
| LIP062_1804 | – | – | H | – | – | – | – | – | – | A | – | – | – | – | A | T | – | – | – |
| LIP062_1803 | – | – | H | – | – | V | – | – | – | A | – | – | – | – | S | A | – | – | – |
| LIP062_1801 | – | – | – | – | – | – | – | – | – | A | – | – | – | – | – | G | – | – | – |
| LIP062_1799 | – | – | – | – | – | – | – | – | – | A | – | – | – | – | N | T | – | – | – |
| LIP062_1798 | – | – | Y | – | – | V | – | – | – | A | – | – | – | – | N | T | – | – | – |
| LIP062_1797 | – | – | H | – | – | T | – | – | – | A | – | – | – | – | – | A | – | – | – |
| LIP062_1796 | – | – | H | – | – | – | – | – | – | A | – | – | – | – | A | S | – | – | – |
| LIP062_1795 | – | – | N | – | – | V | – | – | – | A | – | – | – | – | N | T | – | – | – |
| LIP062_1793 | – | – | – | – | – | – | – | – | – | A | – | – | – | – | – | T | – | – | – |
| LIP062_1792 | – | – | Y | – | – | V | – | – | – | A | – | – | – | – | S | T | – | – | – |
| LIP062_1790 | – | – | – | – | – | – | – | – | – | A | – | – | – | – | S | S | – | – | – |
| LIP062_1788 | – | – | N | – | – | L | – | – | – | A | – | – | – | – | S | G | – | – | – |
| LIP062_1782 | – | – | N | – | – | – | – | – | – | L | – | – | – | – | N | T | – | – | – |
| LIP062_1781 | – | – | H | – | – | A | – | – | – | L | – | – | – | – | A | T | – | – | – |
| LIP062_1780 | – | – | H | – | – | – | – | – | – | L | – | – | – | – | – | G | – | – | – |
| LIP062_1779 | – | – | N | – | – | V | – | – | – | L | – | – | – | – | D | T | – | – | – |
| LIP062_1778 | – | – | – | – | – | – | – | – | – | L | – | – | – | – | A | T | – | – | – |
| LIP062_1776 | – | – | H | – | – | V | – | – | – | L | – | – | – | – | – | A | – | – | – |
| LIP062_1775 | – | – | T | – | – | V | – | – | – | L | – | – | – | – | S | A | – | – | – |
| LIP062_1774 | – | – | – | – | – | – | – | – | – | L | – | – | – | – | D | A | – | – | – |
| LIP062_1773 | – | – | N | – | – | V | – | – | – | L | – | – | – | – | A | A | – | – | – |
| LIP062_1770 | – | – | – | – | – | – | – | – | – | L | – | – | – | – | N | T | – | – | – |
| LIP062_1768 | – | – | – | – | – | – | – | – | – | L | – | – | – | – | D | T | – | – | – |

TABLE 1-continued

| Lipase | \multicolumn{19}{c}{Amino Acid Residue Position Numbers} | | | | | | | | | | | | | | | | | | |
|---|---|---|---|---|---|---|---|---|---|---|---|---|---|---|---|---|---|---|---|
| LIP062 | 23 | 33 | 82 | 83 | 84 | 84' | 85 | 160 | 199 | 254 | 255 | 256 | 258 | 263 | 264 | 265 | 268 | 308 | 311 |
| | Y | K | S | S | N | – | I | K | P | I | I | A | L | D | T | D | T | D | Y |
| LIP062_1767 | – | – | – | – | – | – | – | – | – | L | – | – | – | – | S | T | – | – | – |
| LIP062_1766 | – | – | – | – | – | – | – | – | – | L | – | – | – | – | N | A | – | – | – |
| LIP062_1704 | – | – | H | – | – | – | – | – | – | – | – | – | – | – | A | A | – | – | – |
| LIP062_1703 | – | – | H | – | – | T | – | – | – | – | – | – | – | – | A | A | – | – | – |
| LIP062_1701 | – | – | T | – | – | V | – | – | – | – | – | – | – | – | G | T | – | – | – |
| LIP062_1700 | – | – | – | – | – | – | – | – | – | – | – | – | – | – | S | T | – | – | – |
| LIP062_1696 | – | – | – | – | – | – | – | – | – | – | – | – | – | – | A | T | – | – | – |
| LIP062_1695 | – | – | N | – | – | V | – | – | – | – | – | – | – | – | A | T | – | – | – |
| LIP062_1694 | – | – | – | – | – | – | – | – | – | – | – | – | – | – | – | G | – | – | – |
| LIP062_1692 | – | – | – | – | – | – | – | – | – | – | – | – | – | – | A | T | – | – | – |
| LIP062_1691 | – | – | N | – | – | V | – | – | – | – | – | – | – | – | S | S | – | – | – |
| LIP062_1686 | – | – | N | – | – | V | – | – | – | – | – | – | – | – | A | S | – | – | – |
| LIP062_1685 | – | – | N | – | – | V | – | – | – | – | – | – | – | – | N | A | – | – | – |
| LIP062_1684 | – | – | – | – | – | – | – | – | – | – | – | – | – | – | N | T | – | – | – |
| LIP062_1683 | – | – | – | – | – | – | – | – | – | – | – | – | – | – | D | A | – | – | – |
| LIP062_1681 | – | – | T | – | – | – | – | – | – | – | – | – | – | – | N | T | – | – | – |
| LIP062_1680 | – | – | N | – | – | A | – | – | – | – | – | – | – | – | – | T | – | – | – |
| LIP062_1678 | – | – | N | – | – | – | – | – | – | – | – | – | – | – | – | A | – | – | – |
| LIP062_1677 | – | – | – | – | – | – | – | – | – | – | – | – | – | – | G | T | – | – | – |
| LIP062_1676 | – | – | Y | – | – | – | – | – | – | – | – | – | – | – | G | T | – | – | – |
| LIP062_1674 | – | – | – | – | – | – | – | – | – | – | – | – | – | – | G | T | – | – | – |
| LIP062_1670 | – | – | N | – | – | – | – | – | – | – | – | – | – | – | – | T | – | – | – |
| LIP062_1669 | – | – | – | – | – | – | – | – | – | – | – | – | – | – | S | G | – | – | – |
| LIP062_1668 | – | – | N | – | – | – | – | – | – | – | – | – | – | – | – | G | – | – | – |
| LIP062_1667 | – | – | – | – | – | A | – | – | – | – | – | – | – | – | – | G | – | – | – |
| LIP062_1665 | – | – | – | – | – | – | – | – | – | – | – | – | – | – | D | T | – | – | – |
| LIP062_1664 | – | – | N | – | – | – | – | – | – | L | – | – | – | – | A | T | – | – | – |
| LIP062_0450 | – | – | – | – | – | F | – | – | – | – | – | – | – | – | – | – | – | – | – |
| LIP062_0449 | – | – | – | – | – | Y | – | – | – | – | – | – | – | – | – | – | – | – | – |
| LIP062_0391 | – | – | – | – | – | – | – | – | – | – | – | – | – | – | – | – | – | – | – |

Example 2: Expression and Purification of Lipase Enzymes

Expression

The variant lipase enzymes were obtained by constructing expression plasmids containing the encoding polynucleotide sequences, transforming plasmids into *Pichia pastoris* (Komagataella phaffii) and growing the resulting expression strains in the following way. Fresh *Pichia pastoris* cells of the expression strains were obtained by spreading the glycerol stocks of sequence-confirmed strains onto Yeast extract Peptone Dextrose (YPD) agar plates containing Zeocin. After 2 days, starter seed cultures of the production strains were inoculated into 100 mL of Buffered Glycerol Complex Medium (BMGY) using cells from these plates, and grown for 20-24 hours at 30° C. and 225-250 rpm. Seed cultures were scaled up by transferring suitable amounts into 2-4 L of BMMY medium in a baffled Fermentor. Fermentations were carried out at 30° C. and under 1100 rpm of agitation, supplied via flat-blade impellers, for 48-72 hours. After the initial batch-phase of fermentation, sterile-filtered Methanol was added as feed whenever the dissolved oxygen level in the culture dipped below 30%. Alternatively, feed was added every 3 hours at 0.5% v/v of the starting batch culture. The final fermentation broth was centrifuged at 7000×g for 30 mins at 4° C. to obtain the cell-free supernatant.

Expression levels of the variant lipase enzymes are shown in Table 2, determined as follows: supernatant was assayed for protein of interest expression by either SDS-PAGE or capillary electrophoresis and by enzymatic activity using PNP-octanoate as substrate. The results are provided below in Table 2, and the data is shown as a percentage as compared to the parent (LIP062) expression. The expression levels were not determined "n.d." for some of the variant lipase enzymes; however, enough material was generated to move the variant lipase enzyme into the Lipase Activity testing in Example 3, and sent for amino acid sequence identification as described above in Example 1, Table 1.

TABLE 2

| Lipase | Expression |
| --- | --- |
| LIP062 | 100 |
| LIP089 | 100 |
| LIP090 | 20 |
| LIP094 | 100 |
| LIP095 | 100 |
| LIP096 | 100 |
| LIP062_391 | 20 |
| LIP101 | 30 |
| LIP102 | 30 |
| LIP099 | 30 |
| LIP100 | 50 |
| LIP062_449 | 20 |
| LIP062_450 | 20 |
| LIP108 | 80 |
| LIP109 | 70 |
| LIP110 | 65 |
| LIP111 | 140 |
| LIP113 | 100 |
| LIP114 | 62 |
| LIP115 | 30 |
| LIP116 | 71 |
| LIP117 | 24 |
| LIP118 | 28 |
| LIP119 | 34 |
| LIP120 | 80 |
| LIP123 | 80 |
| LIP124 | 26 |
| LIP126 | 200 |
| LIP134 | 200 |
| LIP135 | 150 |
| LIP130 | 49 |
| LIP131 | 57 |
| LIP146 | n.d. |
| LIP147 | n.d. |
| LIP148 | n.d. |
| LIP149 | n.d. |
| LIP142 | 100 |
| LIP143 | 200 |
| LIP144 | 100 |
| LIP145 | 100 |
| LIP062_1664 | n.d. |
| LIP062_1665 | n.d. |
| LIP160 | n.d. |
| LIP062_1667 | n.d. |
| LIP062_1668 | n.d. |
| LIP062_1669 | n.d. |
| LIP062_1670 | n.d. |
| LIP161 | n.d. |
| LIP154 | 100 |
| LIP162 | n.d. |
| LIP062_1674 | n.d. |
| LIP163 | n.d. |
| LIP062_1676 | n.d. |
| LIP062_1677 | n.d. |
| LIP062_1678 | n.d. |
| LIP165 | n.d. |
| LIP062_1680 | n.d. |
| LIP062_1681 | n.d. |
| LIP150 | n.d. |

TABLE 2-continued

| Lipase | Expression |
| --- | --- |
| LIP062_1683 | n.d. |
| LIP062_1684 | n.d. |
| LIP062_1685 | n.d. |
| LIP062_1686 | n.d. |
| LIP155 | n.d. |
| LIP151 | n.d. |
| LIP156 | n.d. |
| LIP153 | n.d. |
| LIP062_1691 | n.d. |
| LIP062_1692 | n.d. |
| LIP159 | n.d. |
| LIP062_1694 | n.d. |
| LIP062_1695 | n.d. |
| LIP062_1696 | n.d. |
| LIP157 | n.d. |
| LIP158 | n.d. |
| LIP164 | n.d. |
| LIP062_1700 | n.d. |
| LIP062_1701 | n.d. |
| LIP152 | n.d. |
| LIP062_1703 | n.d. |
| LIP062_1704 | n.d. |
| LIP062_1766 | n.d. |
| LIP062_1767 | n.d. |
| LIP062_1768 | n.d. |
| LIP166 | n.d. |
| LIP062_1770 | n.d. |
| LIP167 | n.d. |
| LIP168 | n.d. |
| LIP062_1773 | n.d. |
| LIP062_1774 | n.d. |
| LIP062_1775 | n.d. |
| LIP062_1776 | n.d. |
| LIP169 | n.d. |
| LIP062_1778 | n.d. |
| LIP062_1779 | n.d. |
| LIP062_1780 | n.d. |
| LIP062_1781 | n.d. |
| LIP062_1782 | n.d. |
| LIP062_1788 | 100 |
| LIP170 | 100 |
| LIP062_1790 | 100 |
| LIP171 | 200 |
| LIP062_1792 | 200 |
| LIP062_1793 | 100 |
| LIP181 | 100 |
| LIP062_1795 | 100 |
| LIP062_1796 | 100 |
| LIP062_1797 | 100 |
| LIP062_1798 | 100 |
| LIP062_1799 | 200 |
| LIP172 | 50 |
| LIP062_1801 | 100 |
| LIP173 | 100 |
| LIP062_1803 | 100 |
| LIP062_1804 | 100 |
| LIP062_1805 | 100 |
| LIP174 | 200 |
| LIP062_1807 | 100 |
| LIP175 | 100 |
| LIP178 | 100 |
| LIP062_1810 | 200 |
| LIP176 | 100 |
| LIP062_1812 | 100 |
| LIP177 | 100 |
| LIP062_1814 | 100 |
| LIP179 | 100 |
| LIP062_1816 | 200 |
| LIP062_1817 | 100 |
| LIP062_1818 | 100 |
| LIP180 | 200 |
| LIP062_1820 | 100 |
| LIP182 | 50 |
| LIP062_1822 | 100 |
| LIP062_1823 | 100 |
| LIP062_1824 | 100 |
| LIP062_1825 | 100 |
| LIP062_1826 | 10 |

TABLE 2-continued

| Lipase | Expression |
|---|---|
| LIP062_1827 | 100 |
| LIP062_1828 | 9 |
| LIP062_1829 | 10 |
| LIP062_1830 | 40 |
| LIP062_1831 | 200 |
| LIP062_1832 | 120 |
| LIP062_1833 | 140 |
| LIP062_1834 | 250 |
| LIP062_1835 | 40 |
| LIP062_1836 | 80 |
| LIP062_1837 | 67 |
| LIP062_1838 | 100 |
| LIP062_1839 | 50 |
| LIP062_1840 | 50 |
| LIP062_1841 | 90 |
| LIP062_1842 | 20 |
| LIP062_1843 | 40 |
| LIP062_1844 | 110 |
| LIP062_1845 | 65 |
| LIP062_1846 | 110 |
| LIP062_1847 | 90 |
| LIP062_1848 | 200 |
| LIP062_1849 | 40 |
| LIP062_1850 | 40 |
| LIP062_1851 | 90 |
| LIP062_1852 | 80 |
| LIP062_1853 | 200 |
| LIP062_1854 | 80 |
| LIP062_1855 | 20 |
| LIP062_1856 | 10 |
| LIP062_1857 | 50 |
| LIP062_1858 | 10 |
| LIP062_1859 | 90 |
| LIP062_1860 | 10 |
| LIP062_1861 | 45 |
| LIP062_1862 | 65 |
| LIP062_1863 | 100 |
| LIP062_1864 | 70 |
| LIP062_1865 | 70 |
| LIP062_1866 | 160 |
| LIP062_1867 | 200 |
| LIP062_1868 | 80 |
| LIP062_1869 | 100 |
| LIP062_1870 | 75 |
| LIP062_1871 | 85 |
| LIP062_1872 | 100 |
| LIP062_1873 | 65 |
| LIP062_1874 | 1 |
| LIP062_1875 | 30 |
| LIP062_1876 | 60 |
| LIP062_1877 | 130 |
| LIP062_1878 | 100 |
| LIP062_1879 | 150 |
| LIP062_1880 | 200 |
| LIP062_1881 | 150 |
| LIP062_1882 | 360 |
| LIP062_1883 | 6 |
| LIP062_1884 | 10 |
| LIP062_1885 | 41 |
| LIP062_1886 | 360 |
| LIP062_1887 | 40 |
| LIP062_1888 | 20 |
| LIP062_1889 | 26 |
| LIP062_1890 | 20 |
| LIP062_1891 | 14 |
| LIP062_1892 | 50 |
| LIP062_1893 | 30 |
| LIP062_1894 | n.d. |
| LIP062_1895 | n.d. |
| LIP062_1896 | n.d. |
| LIP062_1897 | n.d. |
| LIP062_1898 | n.d. |
| LIP062_1899 | n.d. |
| LIP062_1900 | n.d. |
| LIP062_1901 | n.d. |
| LIP062_1902 | n.d. |
| LIP062_1903 | n.d. |
| LIP062_1904 | 100 |
| LIP062_1905 | 100 |
| LIP062_1906 | 100 |
| LIP062_1907 | 100 |
| LIP062_1908 | 100 |
| LIP062_1909 | 100 |

Recovery

After filtering through cheese-cloth, the cell-free supernatants were ultrafiltered using a lab-scale tangential flow filtration (TFF) system with a molecular weight cut-off of 5 kD (SpectrumLabs). Samples were first concentrated 10-20× and then buffer-exchanged 5× into 50 mM HEPES pH 7.5. The resultant retentate was centrifuged at 27000×g for 1 hour, and then sterile filtered through 0.2 m filters to remove any production organisms or particulate matter. Total protein content of the final samples was determined using the Braford assay. Lipases were lyophilized to form powder.

Example 3—Lipase Activity

The activity of the variant lipase enzymes was determined using natural substrates in solution. Natural lipid substrates were prepared at 5 mM final concentration in 0.25% sodium deoxycholate by sonication. Substrate (15 µL) was mixed with 30 uL fluorescein (0.25 µg/mL in 10 mM CaCl2) and 10 µL recovered lipase (~1-2 µg/mL) pre-diluted in 5 mM Hepes pH 7.5. Products of lipid hydrolysis were monitored by the drop in fluorescence due to pH change (485 nm/525 nm for excitation/emission), recorded kinetically every 30 seconds for 10 min at 26° C. Activity on a log scale was proportional with the fluorescence change per min. The results are shown below in Table 3, the data is expressed as percentage of parent (LIP062) fluorescence change at same protein concentration. The activity of the variant was not determined "n.d." for some of the variant lipase enzymes on some of the substrates; however, enough material was created as described in Example 2, and sent for amino acid sequence identification as described above in Example 1, Table 1.

TABLE 3

| Lipase | 1-Olein | Galactolipids | PC | C8-PNP | TAGs |
|---|---|---|---|---|---|
| LIP062 | 100 | 100 | 100 | 100 | 100 |
| LIP089 | 50 | 80 | 95 | n.d. | 45 |
| LIP090 | 85 | 60 | 70 | n.d. | 55 |
| LIP094 | 70 | 80 | 15 | 67 | 75 |
| LIP095 | 85 | 95 | 10 | 67 | 110 |
| LIP096 | 75 | 80 | 25 | 100 | 65 |
| LIP062_391 | 65 | 90 | 110 | 100 | 110 |
| LIP101 | 50 | 50 | 10 | 61 | 110 |
| LIP102 | 80 | 95 | 60 | 90 | 110 |
| LIP099 | 70 | 80 | 75 | 150 | 100 |
| LIP100 | 70 | 90 | 100 | 100 | 95 |
| LIP062_449 | 50 | 70 | 65 | 120 | 50 |
| LIP062_450 | 35 | 60 | 55 | 120 | 40 |
| LIP108 | 106 | 125 | 114 | 80 | 100 |
| LIP109 | 115 | 171 | 140 | 130 | 120 |
| LIP110 | 110 | 150 | 140 | 150 | 110 |
| LIP111 | 100 | 145 | 90 | 180 | 110 |
| LIP113 | 70 | 125 | 100 | 161 | 70 |
| LIP114 | 50 | 110 | 90 | 95 | 80 |
| LIP115 | 50 | 100 | 100 | 139 | 200 |
| LIP116 | 50 | 100 | 60 | 102 | 60 |
| LIP117 | 60 | 130 | 90 | 112 | 70 |
| LIP118 | 50 | 125 | 100 | 44 | 200 |
| LIP119 | 75 | 130 | 100 | 114 | 50 |

TABLE 3-continued

| Lipase | 1-Olein | Galactolipids | PC | C8-PNP | TAGs |
|---|---|---|---|---|---|
| LIP120 | 70 | 115 | 85 | 31 | 50 |
| LIP123 | 87 | 103 | 89 | 62 | 117 |
| LIP124 | 88 | 118 | 147 | 67 | 80 |
| LIP126 | 84 | 79 | 111 | 40 | 88 |
| LIP134 | 93 | 89 | 127 | n.d. | 78 |
| LIP135 | 85 | 76 | 116 | n.d. | 60 |
| LIP130 | 66 | 72 | 89 | 78 | 45 |
| LIP131 | 74 | 86 | 140 | 180 | 52 |
| LIP146 | 60 | 136 | 94 | n.d. | 74 |
| LIP147 | 69 | 186 | 142 | n.d. | 124 |
| LIP148 | 78 | 164 | 100 | n.d. | 131 |
| LIP149 | 57 | 128 | 44 | n.d. | 87 |
| LIP142 | 64 | 159 | 52 | n.d. | 70 |
| LIP143 | 81 | 214 | 86 | n.d. | 84 |
| LIP144 | 46 | 112 | 41 | n.d. | 66 |
| LIP145 | 76 | 164 | 85 | n.d. | 79 |
| LIP062_1664 | n.d. | n.d. | n.d. | n.d. | n.d. |
| LIP062_1665 | n.d. | n.d. | n.d. | n.d. | n.d. |
| LIP160 | 51 | 104 | 25 | n.d. | 102 |
| LIP062_1667 | n.d. | n.d. | n.d. | n.d. | n.d. |
| LIP062_1668 | n.d. | n.d. | n.d. | n.d. | n.d. |
| LIP062_1669 | n.d. | n.d. | n.d. | n.d. | n.d. |
| LIP062_1670 | n.d. | n.d. | n.d. | n.d. | n.d. |
| LIP161 | 51 | 129 | 5 | n.d. | 86 |
| LIP154 | 54 | 122 | 5 | n.d. | 100 |
| LIP162 | 60 | 131 | 10 | n.d. | 101 |
| LIP062_1674 | n.d. | n.d. | n.d. | n.d. | n.d. |
| LIP163 | 51 | 106 | 10 | n.d. | 79 |
| LIP062_1676 | n.d. | n.d. | n.d. | n.d. | n.d. |
| LIP062_1677 | n.d. | n.d. | n.d. | n.d. | n.d. |
| LIP062_1678 | n.d. | n.d. | n.d. | n.d. | n.d. |
| LIP165 | 43 | 105 | 6 | n.d. | 39 |
| LIP062_1680 | n.d. | n.d. | n.d. | n.d. | n.d. |
| LIP062_1681 | n.d. | n.d. | n.d. | n.d. | n.d. |
| LIP150 | 69 | 131 | 75 | n.d. | 80 |
| LIP062_1683 | n.d. | n.d. | n.d. | n.d. | n.d. |
| LIP062_1684 | n.d. | n.d. | n.d. | n.d. | n.d. |
| LIP062_1685 | n.d. | n.d. | n.d. | n.d. | n.d. |
| LIP062_1686 | n.d. | n.d. | n.d. | n.d. | n.d. |
| LIP155 | 53 | 94 | 9 | n.d. | 69 |
| LIP151 | 49 | 90 | 40 | n.d. | 70 |
| LIP156 | 44 | 111 | 22 | n.d. | 67 |
| LIP153 | 76 | 119 | 118 | n.d. | 82 |
| LIP062_1691 | n.d. | n.d. | n.d. | n.d. | n.d. |
| LIP062_1692 | n.d. | n.d. | n.d. | n.d. | n.d. |
| LIP159 | 50 | 121 | 9 | n.d. | 82 |
| LIP062_1694 | n.d. | n.d. | n.d. | n.d. | n.d. |
| LIP062_1695 | n.d. | n.d. | n.d. | n.d. | n.d. |
| LIP062_1696 | n.d. | n.d. | n.d. | n.d. | n.d. |
| LIP157 | 49 | 103 | 31 | n.d. | 109 |
| LIP158 | 81 | 180 | 61 | n.d. | 117 |
| LIP164 | 56 | 120 | 10 | n.d. | 68 |
| LIP062_1700 | n.d. | n.d. | n.d. | n.d. | n.d. |
| LIP062_1701 | n.d. | n.d. | n.d. | n.d. | n.d. |
| LIP152 | 57 | 116 | 24 | n.d. | 85 |
| LIP062_1703 | n.d. | n.d. | n.d. | n.d. | n.d. |
| LIP062_1704 | n.d. | n.d. | n.d. | n.d. | n.d. |
| LIP062_1766 | 29 | 59 | 0 | n.d. | 41 |
| LIP062_1767 | 39 | 75 | 8 | n.d. | 38 |
| LIP062_1768 | 27 | 54 | 0 | n.d. | 30 |
| LIP166 | 34 | 72 | 2 | n.d. | 47 |
| LIP062_1770 | 29 | 42 | 10 | n.d. | 37 |
| LIP167 | 59 | 118 | 8 | n.d. | 57 |
| LIP168 | 44 | 99 | 0 | n.d. | 59 |
| LIP062_1773 | 42 | 87 | 12 | n.d. | 33 |
| LIP062_1774 | 22 | 26 | 8 | n.d. | 33 |
| LIP062_1775 | 35 | 61 | 7 | n.d. | 46 |
| LIP062_1776 | 30 | 41 | 27 | n.d. | 53 |
| LIP169 | 59 | 118 | 3 | n.d. | 54 |
| LIP062_1778 | 41 | 73 | 10 | n.d. | 30 |
| LIP062_1779 | 20 | 55 | 4 | n.d. | 18 |
| LIP062_1780 | 47 | 86 | 19 | n.d. | 37 |
| LIP062_1781 | 39 | 59 | 5 | n.d. | 21 |
| LIP062_1782 | 24 | 52 | 1 | n.d. | 21 |
| LIP062_1788 | 51 | 105 | 17 | n.d. | n.d. |
| LIP170 | 75 | 160 | 20 | n.d. | 100 |
| LIP062_1790 | 95 | 123 | 128 | n.d. | n.d. |
| LIP171 | 65 | 138 | 7 | n.d. | 81 |
| LIP062_1792 | 87 | 117 | 17 | n.d. | n.d. |
| LIP062_1793 | 94 | 127 | 91 | n.d. | n.d. |
| LIP181 | 65 | 139 | 16 | n.d. | 104 |
| LIP062_1795 | 59 | 103 | 8 | n.d. | n.d. |
| LIP062_1796 | 78 | 120 | 40 | n.d. | n.d. |
| LIP062_1797 | 51 | 80 | 17 | n.d. | n.d. |
| LIP062_1798 | 47 | 72 | 0 | n.d. | n.d. |
| LIP062_1799 | 72 | 100 | 13 | n.d. | n.d. |
| LIP172 | 44 | 85 | 5 | n.d. | 69 |
| LIP062_1801 | 105 | 150 | 276 | n.d. | n.d. |
| LIP173 | 89 | 153 | 138 | n.d. | 98 |
| LIP062_1803 | 83 | 127 | 15 | n.d. | n.d. |
| LIP062_1804 | 87 | 115 | 16 | n.d. | n.d. |
| LIP062_1805 | 67 | 100 | 87 | n.d. | n.d. |
| LIP174 | 82 | 153 | 73 | n.d. | 94 |
| LIP062_1807 | 76 | 106 | 10 | n.d. | n.d. |
| LIP175 | 90 | 179 | 137 | n.d. | 106 |
| LIP178 | 60 | 109 | 18 | n.d. | 92 |
| LIP062_1810 | 59 | 90 | 10 | n.d. | n.d. |
| LIP176 | 86 | 169 | 12 | n.d. | 100 |
| LIP062_1812 | 78 | 105 | 43 | n.d. | n.d. |
| LIP177 | 106 | 185 | 168 | n.d. | 101 |
| LIP062_1814 | 66 | 91 | 67 | n.d. | n.d. |
| LIP179 | 87 | 148 | 40 | n.d. | 113 |
| LIP062_1816 | 110 | 141 | 19 | n.d. | n.d. |
| LIP062_1817 | 48 | 67 | 4 | n.d. | n.d. |
| LIP062_1818 | 83 | 119 | 17 | n.d. | n.d. |
| LIP180 | 68 | 99 | 7 | n.d. | 100 |
| LIP062_1820 | 87 | 125 | 37 | n.d. | n.d. |
| LIP182 | 63 | 132 | 5 | n.d. | 63 |
| LIP062_1822 | 51 | 75 | 3 | n.d. | n.d. |
| LIP062_1823 | 84 | 108 | 109 | n.d. | n.d. |
| LIP062_1824 | 83 | 113 | 144 | n.d. | n.d. |
| LIP062_1825 | 88 | 133 | 24 | n.d. | n.d. |
| LIP062_1826 | 15 | 25 | 25 | n.d. | 25 |
| LIP062_1827 | 1 | 60 | 0 | 1 | 0 |
| LIP062_1828 | 35 | 50 | 40 | 70 | 24 |
| LIP062_1829 | 40 | 50 | 3 | 70 | 4 |
| LIP062_1830 | 70 | 80 | 90 | 135 | 100 |
| LIP062_1831 | 130 | 100 | 100 | 50 | 80 |
| LIP062_1832 | 100 | 90 | 80 | 160 | 100 |
| LIP062_1833 | 120 | 110 | 90 | 130 | 120 |
| LIP062_1834 | 200 | 90 | 60 | 150 | 80 |
| LIP062_1835 | 90 | 70 | 80 | 100 | 80 |
| LIP062_1836 | 110 | 60 | 55 | 90 | 20 |
| LIP062_1837 | 90 | 50 | 40 | 160 | 90 |
| LIP062_1838 | 170 | 60 | 40 | 160 | 70 |
| LIP062_1839 | 120 | 65 | 50 | 3 | 0 |
| LIP062_1840 | 86 | 60 | 60 | 240 | 120 |
| LIP062_1841 | 140 | 80 | 60 | 20 | 0 |
| LIP062_1842 | 110 | 70 | 70 | 200 | 100 |
| LIP062_1843 | 55 | 40 | 25 | 260 | 90 |
| LIP062_1844 | 130 | 100 | 70 | 30 | 0 |
| LIP062_1845 | 180 | 80 | 24 | 35 | 0 |
| LIP062_1846 | 140 | 100 | 80 | 55 | 20 |
| LIP062_1847 | 150 | 80 | 20 | 20 | 15 |
| LIP062_1848 | 100 | 40 | 70 | 15 | 0 |
| LIP062_1849 | 90 | 55 | 60 | 30 | 120 |
| LIP062_1850 | 90 | 15 | 10 | 30 | 0 |
| LIP062_1851 | 110 | 50 | 0 | 20 | 0 |
| LIP062_1852 | 130 | 80 | 80 | 20 | 40 |
| LIP062_1853 | 100 | 70 | 45 | 10 | 0 |
| LIP062_1854 | 150 | 90 | 30 | 20 | 5 |
| LIP062_1855 | 0 | 0 | 0 | 0 | 0 |
| LIP062_1856 | 0 | 0 | 0 | 0 | 0 |
| LIP062_1857 | 5 | 5 | 5 | 5 | 5 |
| LIP062_1858 | n.d. | n.d. | n.d. | n.d. | n.d. |
| LIP062_1859 | 45 | 50 | 50 | 60 | 35 |
| LIP062_1860 | n.d. | n.d. | n.d. | n.d. | n.d. |
| LIP062_1861 | 21 | 2 | 1 | 26 | 18 |
| LIP062_1862 | 76 | 70 | 80 | 235 | 100 |
| LIP062_1863 | 76 | 76 | 46 | 100 | 67 |
| LIP062_1864 | 77 | 87 | 78 | 127 | 68 |
| LIP062_1865 | 35 | 22 | 21 | 70 | 34 |
| LIP062_1866 | 76 | 81 | 60 | 53 | 75 |
| LIP062_1867 | 46 | 47 | 12 | 148 | 47 |
| LIP062_1868 | 111 | 159 | 121 | 76 | 88 |
| LIP062_1869 | 107 | 154 | 126 | 74 | 87 |

TABLE 3-continued

| Lipase | 1-Olein | Galactolipids | PC | C8-PNP | TAGs |
|---|---|---|---|---|---|
| LIP062_1870 | 98 | 20 | 22 | 61 | 8 |
| LIP062_1871 | 144 | 112 | 43 | 88 | 86 |
| LIP062_1872 | 103 | 122 | 82 | 89 | 104 |
| LIP062_1873 | 80 | 12 | 10 | 138 | 78 |
| LIP062_1874 | 3 | 0 | 15 | 0 | 13 |
| LIP062_1875 | 68 | 55 | 89 | 299 | 85 |
| LIP062_1876 | 75 | 70 | 100 | 125 | 125 |
| LIP062_1877 | 70 | 70 | 95 | 70 | 110 |
| LIP062_1878 | n.d. | n.d. | n.d. | n.d. | n.d. |
| LIP062_1879 | n.d. | n.d. | n.d. | n.d. | n.d. |
| LIP062_1880 | n.d. | n.d. | n.d. | n.d. | n.d. |
| LIP062_1881 | n.d. | n.d. | n.d. | n.d. | n.d. |
| LIP062_1882 | 109 | 186 | 157 | 69 | 58 |
| LIP062_1883 | 47 | 37 | 57 | 73 | 71 |
| LIP062_1884 | 64 | 52 | 51 | 117 | 16 |
| LIP062_1885 | 53 | 79 | 65 | 201 | 92 |
| LIP062_1886 | 93 | 70 | 88 | 197 | 95 |
| LIP062_1887 | 60 | 51 | 58 | 47 | 81 |
| LIP062_1888 | 74 | 120 | 109 | 50 | 38 |
| LIP062_1889 | 59 | 88 | 73 | 73 | 57 |
| LIP062_1890 | 64 | 68 | 66 | 52 | 52 |
| LIP062_1891 | 57 | 54 | 59 | 135 | 44 |
| LIP062_1892 | 63 | 77 | 57 | 28 | 39 |
| LIP062_1893 | 41 | 37 | 16 | 12 | 22 |
| LIP062_1894 | 97 | 145 | 31 | n.d. | 142 |
| LIP062_1895 | 54 | 61 | 55 | n.d. | 67 |
| LIP062_1896 | 90 | 144 | 104 | n.d. | 114 |
| LIP062_1897 | 45 | 55 | 34 | n.d. | 56 |
| LIP062_1898 | 37 | 23 | 0 | n.d. | 76 |
| LIP062_1899 | 36 | 39 | 2 | n.d. | 70 |
| LIP062_1900 | 63 | 79 | 46 | n.d. | 105 |
| LIP062_1901 | 54 | 58 | 48 | n.d. | 78 |
| LIP062_1902 | 40 | 48 | 22 | n.d. | 131 |
| LIP062_1903 | 29 | 35 | 5 | n.d. | 149 |
| LIP062_1904 | 62 | 112 | 77 | n.d. | 42 |
| LIP062_1905 | 34 | 63 | 18 | n.d. | 37 |
| LIP062_1906 | 18 | 11 | 3 | n.d. | 19 |
| LIP062_1907 | 26 | 19 | 3 | n.d. | 25 |
| LIP062_1908 | 32 | 46 | 8 | n.d. | 25 |
| LIP062_1909 | 47 | 73 | 19 | n.d. | 31 |

Example 4: Lipase Specific Activity at Various pH Values

The variant lipase enzymes were diluted at the appropriate concentration in 5 mM Hepes pH 7.5, then further diluted 16-fold into 0.4 mM PNP-octanoate prepared in broad range buffer of pH 6.5 to pH 12.0. The broad range buffer contained: 25 mM Phosphoric acid, 25 mM Citric Acid, 25 mM Boric Acid, 25 mM CAPS, and 50 mM NaCl. For pH 8.0, the buffer was supplemented with 10 mM Tris pH 8.0. Activity was measured at 26° C. by recording the absorbance at 405 nm every 40 seconds for 15 minutes. Activity was corrected for the background (no enzyme) and for the absorbance of PNP at each pH under identical conditions. The results are presented in Table 6, and the data is shown as micrograms PNP/min/mg enzyme.

TABLE 4

Lipase Specific activity at various pH values (micrograms PNP/min/mg enzyme)

| pH | 6.5 | 7 | 7.5 | 8 | 8.5 | 9 | 9.5 | 10 | 10.5 | 11 | 11.5 | 12 |
|---|---|---|---|---|---|---|---|---|---|---|---|---|
| LIP062 | 801 | 1964 | 2972 | 4409 | 6258 | 7196 | 7621 | 7673 | 7378 | 6299 | 3027 | 67 |
| LIP108 | 1223 | 2699 | 3352 | 4889 | 6265 | 6952 | 7000 | 6970 | 6483 | 5300 | 2321 | 641 |
| LIP110 | 1547 | 3316 | 3977 | 5759 | 7572 | 7748 | 8168 | 7979 | 7605 | 6506 | 2829 | 0 |
| LIP117 | 1659 | 3930 | 4859 | 7023 | 8399 | 8633 | 8837 | 8873 | 8541 | 8320 | 2057 | 623 |
| LIP120 | 698 | 1565 | 2137 | 3495 | 5004 | 5837 | 5555 | 5517 | 5592 | 4415 | 1547 | 0 |
| LIP147 | 2148 | 4745 | 5294 | 7279 | 8469 | 8626 | 8903 | 8803 | 8174 | 7058 | 3290 | 0 |
| LIP148 | 1168 | 2322 | 2611 | 3350 | 4115 | 4306 | 4590 | 4309 | 4098 | 3182 | 1629 | 0 |
| LIP151 | 847 | 2442 | 3424 | 4695 | 6895 | 8135 | 7977 | 8073 | 7905 | 6615 | 1747 | 0 |
| LIP152 | 1397 | 4578 | 6733 | 9080 | 12819 | 14112 | 14469 | 14616 | 14249 | 13107 | 11190 | 3022 |
| LIP158 | 1558 | 5829 | 9207 | 13080 | 16994 | 17786 | 20804 | 20591 | 19884 | 17877 | 16228 | 3480 |
| LIP159 | 1597 | 6049 | 11246 | 16254 | 21623 | 23367 | 23500 | 24613 | 24755 | 23503 | 19089 | 3266 |
| LIP160 | 371 | 1989 | 3321 | 4587 | 7027 | 7793 | 6260 | 6777 | 6791 | 6746 | 5275 | 2778 |
| LIP161 | 658 | 2525 | 3417 | 2617 | 1354 | 1144 | 811 | 901 | 1006 | 1198 | 1563 | 2259 |
| LIP162 | 349 | 1789 | 3092 | 3998 | 6919 | 8499 | 7549 | 7997 | 8151 | 5403 | 2591 | 2320 |
| LIP167 | 865 | 4272 | 6674 | 9515 | 13479 | 14562 | 14354 | 14609 | 14067 | 14220 | 11058 | 2655 |
| LIP168 | 732 | 3227 | 5770 | 8165 | 12593 | 14811 | 14549 | 15625 | 15305 | 14363 | 12634 | 2594 |
| LIP170 | 744 | 2290 | 3953 | 5023 | 9480 | 11616 | 10958 | 11796 | 12121 | 10092 | 5869 | 0 |
| LIP171 | 721 | 2069 | 2412 | 1304 | 929 | 907 | 774 | 1072 | 1523 | 1649 | 1807 | 0 |
| LIP173 | 632 | 2700 | 4481 | 6758 | 10606 | 11937 | 11603 | 12338 | 11999 | 10876 | 7959 | 0 |
| LIP174 | 566 | 2145 | 3620 | 5323 | 9161 | 11201 | 9839 | 12847 | 13283 | 11964 | 9053 | 0 |
| LIP175 | 1339 | 4241 | 7361 | 10793 | 15578 | 16856 | 16903 | 18052 | 17557 | 13316 | 11183 | 0 |
| LIP176 | 1042 | 3504 | 5118 | 7951 | 12448 | 14183 | 13354 | 15648 | 15624 | 13333 | 7088 | 0 |
| LIP180 | 281 | 1365 | 2143 | 2618 | 4892 | 7405 | 6977 | 10671 | 12277 | 11056 | 4814 | 31 |
| LIP181 | 298 | 930 | 1229 | 1652 | 3163 | 4865 | 3739 | 5566 | 7607 | 6046 | 3805 | 31 |

Example 5: Evaluation of Lipases in Launder-O-Meter

The lipase enzymes were tested in 2 g/L liquid detergent (ES1 or ES4) or 2 g/L powder detergent (ECE 2), using two multisoil monitors (MSB, NSL, MSL1, and MSL2) per run. The washing temperatures tested are 20° C. and 40° C. The lipases were dosed at 0; and 0.5 ppm.

Selected stain monitors were washed together with cotton ballast fabric and steel balls at either 20° C. or 40° C. in wash liquor using base formulation ES1 or ES4 or ECE 2 in the launder-o-meter (LOM, LP2 Typ, SDL Atlas Inc., USA) under the following washing conditions:

ES1 Liquid Detergent Formulation:

| component | type | A Conc [%] |
|---|---|---|
| Lutensit A-LBS | LAS | 5.5 |
| Edenor coco fatty acid | $C_{12}$-$C_{18}$ coco fatty acid | 2.4 |
| Lutensol AO7 | AEO | 5.5 |
| Texapon N70 | FAEO | 5.5 |
| | 1,2 propylene glycol | 6.0 |
| | ethanol | 2.0 |
| | KOH | 2.2 |

ECE2 Powder Detergent Formulation Composition (ISO 105-C08:2010) from WFK:

| component | A Conc [%] |
|---|---|
| Linear sodium alkyl benzene sulfonate | 9.7 |
| Ethoxylated fatty alcohol C12-18 (7 EO) | 5.2 |
| Sodium Soap | 3.6 |
| Anti foam DC2-4248S | 4.5 |
| Sodium aluminium silicate zeolite 4A | 32 |
| Sodium carbonate | 11.2 |
| Sodium salt of a copolymer from acrylic and maleic acid (Sokalan CP5) | 5.2 |
| Sodium silicate ($SiO_2$:$Na_2O$ = 3.3:1) | 3.4 |
| Carboxymethylcellulose | 1.3 |
| Diethylene triamine penta (methylene phosphonic acid) | 0.8 |
| Sodium sulfate | 9.8 |
| water | 12.2 |

ES4 Liquid Detergent Formulation:

| component | type | A Conc [%] |
|---|---|---|
| Lutensit A-LBS | LAS | 3.63 |
| Edenor coco fatty acid | $C_{12}$-$C_{18}$ coco fatty acid | 2.67 |
| Lutensol AO 7 | AEO | 7.62 |
| Texapon N70 | FAEO | 10.37 |
| | 1,2 propylene glycol | 4.45 |
| | ethanol | 1.48 |
| | KOH | 2.45 |

Test Conditions

| | |
|---|---|
| Washing liquor | 250 ml |
| # Steel balls* | 20 |
| Washing time/temperature | 20 min at 25° C. or 40° C. |
| Dosage Lipase | Either 0 ppm or 1.5 ppm |
| Dosage detergent | 2 g/L or 5 g/L |
| Washing cycles | 1 |
| Water hardness | 2.5 mmol/L; |
| Ballast fabric | 15 g cotton fabric 283 |
| Sum ballast + soiled fabric | 20 g |
| Soiled swatches | 2 × 2.5 g C-S-61 or C-S 62 |
| Fabric/liquor ratio | 1:12.5 |

After the washing, the fabrics were rinsed, spin-dried and dried in the air. The washing performance for the single stains is determined by measuring the remission value of the soiled fabric after wash with the spectrophotometer from Fa. Datacolor (Elrepho 2000) at 460 nm. In general, the higher the remission value, the better the performance. For the multi soil monitors the stain removal performance was determined by using the MACH5 multi area color measurement which gives LAB values and ΔE calculated between unwashed and washed stain (calculation according to example 7). The results are also outlined below in Table 4, trials 5 to 8.

Tested Stains—Stain Samples were all Purchased by CFT, Vlaardingen, NL:

| # | Swatch details | Characteristics |
|---|---|---|
| Stain 1 | E-142/1 | lipstick |
| Stain 2 | W-10 D | sebum |
| Stain 3 | PCS-04 | olive oil |
| Stain 4 | CS-170 | Chocolate Mousse |
| Stain 5 | CS-68 | Chocolate Ice |
| Stain 6 | C-09 | groundnut oil |
| Stain 7 | CS-61 | beef fat |
| Stain 8 | KC-H010 | cocoa |
| Stain 9 | KC-H015 | Frying fat |
| Stain 10 | KC-H134 | Hamburg grease |
| Stain 11 | KC-H131 | Butter fat |

TABLE 5

Wash performance of lipase variants on fat stains in ES1 detergent formulation; data normalized on detergent without Lipase, washing temperature 20° C.

| Lipase | Conc. Lipase | Stain 1 | Stain 2 | Stain 3 | Stain 4 | Stain 5 | Stain 6 |
|---|---|---|---|---|---|---|---|
| — | — | 100 | 100 | 100 | 100 | 100 | 100 |
| Lip173 | 0.5 ppm | 114 | 110 | 116 | 108 | 109 | 122 |
| Lip120 | 0.5 ppm | 104 | 100 | 101 | 106 | 103 | 110 |

| Lipase | Conc. Lipase | Stain 7 | Stain 8 | Stain 9 | Stain 10 | Stain 11 |
|---|---|---|---|---|---|---|
| — | — | 100 | 100 | 100 | 100 | 100 |
| Lip173 | 0.5 ppm | 101 | 109 | 104 | 108 | 107 |
| Lip120 | 0.5 ppm | 85 | 108 | 97 | 113 | 82 |

TABLE 6

Wash performance of lipase variants on fat stains in ES 1 detergent formulation; data normalized on detergent without Lipase, washing temperature 40° C.

| Lipase | Conc. Lipase | Stain 1 | Stain 2 | Stain 3 | Stain 4 | Stain 5 | Stain 6 |
|---|---|---|---|---|---|---|---|
| — | — | 100 | 100 | 100 | 100 | 100 | 100 |
| Lip173 | 0.5 ppm | 114 | 110 | 120 | 105 | 107 | 128 |
| Lip120 | 0.5 ppm | 108 | 103 | 95 | 101 | 100 | 108 |

| Lipase | Conc. Lipase | Stain 7 | Stain 8 | Stain 9 | Stain 10 | Stain 11 |
|---|---|---|---|---|---|---|
| — | — | 100 | 100 | 100 | 100 | 100 |
| Lip173 | 0.5 ppm | 120 | 100 | 113 | 103 | 102 |
| Lip120 | 0.5 ppm | 110 | 102 | 99 | 99 | 98 |

TABLE 7

Wash performance of lipase variants on fat stains in ECE 2 detergent formulation; data normalized on detergent without Lipase, washing temperature 20° C.

| Lipase | Conc. Lipase | Stain 1 | Stain 2 | Stain 3 | Stain 4 | Stain 5 | Stain 6 |
|---|---|---|---|---|---|---|---|
| — | — | 100 | 100 | 100 | 100 | 100 | 100 |
| Lip62 | 0.5 ppm | 115 | 109 | 119 | 108 | 110 | 107 |
| Lip173 | 0.5 ppm | 124 | 110 | 117 | 117 | 121 | 110 |
| Lip160 | 0.5 ppm | 113 | 100 | 115 | 109 | 108 | 100 |

| Lipase | Conc. Lipase | Stain 7 | Stain 8 | Stain 9 | Stain 10 | Stain 11 |
|---|---|---|---|---|---|---|
| — | — | 100 | 100 | 100 | 100 | 100 |
| Lip62 | 0.5 ppm | 116 | 99 | 97 | 123 | 98 |
| Lip173 | 0.5 ppm | 113 | 102 | 108 | 145 | 114 |
| Lip160 | 0.5 ppm | 108 | 96 | 102 | 126 | 93 |

TABLE 8

Wash performance of lipase variants on fat stains in ECE 2 detergent formulation; data normalized on detergent without Lipase, washing temperature 40° C.

| Lipase | Conc. Lipase | Stain 1 | Stain 2 | Stain 3 | Stain 4 | Stain 5 | Stain 6 |
|---|---|---|---|---|---|---|---|
| — | — | 100 | 100 | 100 | 100 | 100 | 100 |
| Lip62 | 0.5 ppm | 98 | 104 | 87 | 104 | 111 | 110 |
| Lip173 | 0.5 ppm | 101 | 104 | 89 | 103 | 112 | 109 |
| Lip160 | 0.5 ppm | 97 | 103 | 105 | 101 | 104 | 102 |

| Lipase | Conc. Lipase | Stain 7 | Stain 8 | Stain 9 | Stain 10 | Stain 11 |
|---|---|---|---|---|---|---|
| — | — | 100 | 100 | 100 | 100 | 100 |
| Lip62 | 0.5 ppm | 107 | 105 | 102 | 101 | 96 |
| Lip173 | 0.5 ppm | 107 | 109 | 115 | 100 | 95 |
| Lip160 | 0.5 ppm | 109 | 111 | 105 | 103 | 100 |

TABLE 9

Wash performance of lipase variants on fat stains in ES 4 detergent formulation; data normalized on detergent without Lipase, washing temperature 20° C.

| Lipase | Conc. Lipase | Stain 1 | Stain 2 | Stain 3 | Stain 4 | Stain 5 | Stain 6 |
|---|---|---|---|---|---|---|---|
| — | — | 100 | 100 | 100 | 100 | 100 | 100 |
| Lip62 | 0.5 ppm | 100 | 98 | 106 | 107 | 108 | 113 |

TABLE 9-continued

Wash performance of lipase variants on fat stains in ES 4 detergent formulation; data normalized on detergent without Lipase, washing temperature 20° C.

| Lip173 | 0.5 ppm | 121 | 103 | 112 | 107 | 108 | 113 |
| Lip160 | 0.5 ppm | 110 | 99 | 109 | 106 | 109 | 115 |

| Lipase | Conc. Lipase | Stain 7 | Stain 8 | Stain 9 | Stain 10 | Stain 11 |
|---|---|---|---|---|---|---|
| — | — | 100 | 100 | 100 | 100 | 100 |
| Lip62 | 0.5 ppm | 104 | 99 | 93 | 111 | 86 |
| Lip173 | 0.5 ppm | 128 | 105 | 109 | 113 | 117 |
| Lip160 | 0.5 ppm | 121 | 103 | 98 | 110 | 107 |

TABLE 10

Wash performance of lipase variants on fat stains in ES 4 detergent formulation; data normalized on detergent without Lipase, washing temperature 40° C.

| Lipase | Conc. Lipase | Stain 1 | Stain 2 | Stain 3 | Stain 4 | Stain 5 | Stain 6 |
|---|---|---|---|---|---|---|---|
| — | — | 100 | 100 | 100 | 100 | 100 | 100 |
| Lip62 | 0.5 ppm | 114 | 96 | 109 | 100 | 102 | 110 |
| Lip173 | 0.5 ppm | 124 | 106 | 112 | 104 | 108 | 115 |
| Lip160 | 0.5 ppm | 118 | 103 | 106 | 105 | 104 | 112 |

| Lipase | Conc. Lipase | Stain 7 | Stain 8 | Stain 9 | Stain 10 | Stain 11 |
|---|---|---|---|---|---|---|
| — | — | 100 | 100 | 100 | 100 | 100 |
| Lip62 | 0.5 ppm | 102 | 98 | 108 | 106 | 99 |
| Lip173 | 0.5 ppm | 114 | 99 | 108 | 110 | 103 |
| Lip160 | 0.5 ppm | 110 | 100 | 106 | 109 | 102 |

Example 6: Evaluation of Lipases in Full Scale Laundry—Comparison with Benchmark Lipase The lipase enzymes were tested in 2 g/L liquid detergent (Persil small & mighty non bio2016 purchased in UK), using two multisoil monitors (MSB, NSL, MSL1, and MSL2) per run. The washing temperatures tested are 20° C. and 40° C. The lipases were dosed 0.5 ppm.

Test Set-Up as in Example 5.

Tested stains: stain samples were all purchased by CFT, Vlaardingen, NL:

| # | Swatch details | Characteristics |
|---|---|---|
| Stain 1 | E-141/1 | Lipstick |
| Stain 2 | W-10 | D Pigment, sebum |
| Stain 3 | PCS-04 | Coloured olive oil |
| Stain 4 | CS-170 | Chocolate Mousse |
| Stain 5 | CS-68 | Chocolate ice cream |
| Stain 6 | C-09 | Groundnut oil |
| Stain 7 | CS-61 | Beef fat |
| Stain 8 | KC-H010 | Cocoa cooks up with milk |
| Stain 9 | KC-H015 | Fat, from actual use in frying |
| Stain 10 | KC-H134 | Hamburg grease |
| Stain 11 | KC-H131 | Butter fat with colorant |
| Stain 12 | KC-H064 | Sauce curry/ oil |
| Stain 13 | KC-H056 | Mediterranean olive sauce |

TABLE 11

Wash performance of lipase variants on fat stains in Persil detergent formulation; data normalized on Lipex (Novozymes), washing temperature 20° C.

| Lipase | Conc. Lipase | Stain 1 | Stain 3 | Stain 4 | Stain 5 | Stain 6 |
|---|---|---|---|---|---|---|
| Lipex | 0.5 ppm | 100 | 100 | 100 | 100 | 100 |
| Lip110 | 0.5 ppm | 103 | 102 | 106 | 107 | 101 |

| Lipase | Conc. Lipase | Stain 8 | Stain 9 | Stain 12 |
|---|---|---|---|---|
| Lipex | 0.5 ppm | 100 | 100 | 100 |
| Lip110 | 0.5 ppm | 111 | 107 | 115 |

TABLE 12

Wash performance of lipase variants on fat stains in Persil detergent formulation; data normalized on Lipex (Novozymes), washing temperature 40° C.

| Lipase | Conc. Lipase | Stain 2 | Stain 3 | Stain 4 | Stain 5 | Stain 6 |
|---|---|---|---|---|---|---|
| Lipex | 0.5 ppm | 100 | 100 | 100 | 100 | 100 |
| Lip110 | 0.5 ppm | 111 | 106 | 108 | 105 | 108 |

| Lipase | Conc. Lipase | Stain 8 | Stain 12 | Stain 13 |
|---|---|---|---|---|
| Lipex | 0.5 ppm | 100 | 100 | 100 |
| Lip110 | 0.5 ppm | 129 | 101 | 102 |

The invention claimed is:

1. A detergent formulation comprising: at least one polypeptide having at least 80% identity with the amino acid sequence of SEQ ID NO:1 and at least one detergent component,
   wherein the polypeptide comprises at least one amino acid residue insertion or substitution at an amino acid residue position number corresponding to 23, 33, 82, 83, 85, 160, 199, 254, 255, 256, 258, 263, 264, 265, 268, 308, or 311 of SEQ ID NO:1;
   wherein the amino acid substitution or insertion is selected from the group consisting of: Y23A, K33N, S82T, S83D, S83H, S83I, S83N, S83R, S83T, S83Y, 84'Y, 84'L, 84'S, I85A, I85C, I85F, I85H, I85L, I85M, I85P, I85S, I85T, I85V, I85Y, K160N, P199I, P199V, I254A, I254C, I254E, I254F, I254G, I254L, I254M, I254N, I254R, I254S, I254V, I254W, I254Y, I255A, I255L, A256D, L258A, L258D; L258E, L258G, L258H, L258N, L258Q, L258R, L258S, L258T, L258V, D263G, D263K, D263P, D263R, D263S; T264A, T264D, T264G, T264I, T264L, T264N, T264S, D265A, D265G, D265K, D265L, D265N, D265S, D265T, T268A, T268G, T268K, T268L, T268N, T268S, D308A, Y311E, and any combination thereof; and
   wherein the polypeptide has lipase activity.

2. A method of cleaning, comprising the steps of
   (a) providing a surface to be cleaned from fatty stains;
   (b) providing the detergent formulation according to claim 1;
   (c) contacting the surface to be cleaned from fatty stains of (a) with the detergent of (b); wherein the polypeptide in the detergent removes the fatty stain from the surface to be cleaned from fatty stains.

3. The detergent formulation of claim 1, further comprising a second enzyme selected from one or more of the group consisting of: a second lipase, an amylase, a protease, a cellulase, a mannanase, a laccase, a pectinase, and a nuclease.

4. The method of claim 2, wherein the surface to be cleaned from fatty stains is: a cloth, a textile, a fabric, a hard surface, or a dish.

5. The method of claim 2, wherein the surface to be cleaned from fatty stains comprises a stain selected from: lipstick, sebum, mustard, olive oil, coco, chocolate, chocolate mousse, chocolate ice cream, chocolate drink, groundnut oil, beef fat, Indian curry, Napoli tomato, make up, blood beef fat, salad dressing, egg yolk, food, frying fat, curry, mediterranean sauce, curry oil sauce, balsamic, hamburger grease, butter fat.

6. The detergent formulation according to claim 1, wherein the formulation is a laundry detergent, a hard surface cleaner, a dishwashing detergent, or a personal hygiene product.

7. The detergent formulation of claim 1, wherein the at least one detergent component is selected from: surfactants, builders, polymers, alkaline, bleaching systems, fluorescent whitening agents, suds suppressors and stabilizers, hydrotropes, rheology modifiers, preservatives, and corrosion inhibitors in amounts effective in washing or cleaning performance or effective in maintaining the physical characteristics of the detergent.

8. The detergent formulation of according to claim 1, wherein detergent is a liquid, a gel, a paste, a soap bar, a powder, or a granulated solid.

* * * * *

SEQUENCE LISTING

<160> NUMBER OF SEQ ID NOS: 2

<210> SEQ ID NO 1
<211> LENGTH: 317
<212> TYPE: PRT
<213> ORGANISM: Fusarium solani

<400> SEQUENCE: 1

```
Ala Ile Thr Ala Ser Gln Leu Asp Tyr Glu Asn Phe Lys Phe Tyr Ile
1               5                   10                  15

Gln His Gly Ala Ala Tyr Cys Asn Ser Glu Thr Ala Ser Gly Gln
            20                  25                  30

Lys Ile Thr Cys Ser Asp Asn Gly Cys Lys Gly Val Glu Ala Asn Asn
                35                  40                  45

Ala Ile Ile Val Ala Ser Phe Val Gly Lys Gly Thr Gly Ile Gly Gly
        50                  55                  60

Tyr Val Ser Thr Asp Asn Val Arg Lys Glu Ile Val Leu Ser Ile Arg
65                  70                  75                  80

Gly Ser Ser Asn Ile Arg Asn Trp Leu Thr Asn Val Asp Phe Gly Gln
                85                  90                  95

Ser Ser Cys Ser Tyr Val Arg Asp Cys Gly Val His Thr Gly Phe Arg
            100                 105                 110

Asn Ala Trp Asp Glu Ile Ala Gln Arg Ala Arg Asp Ala Val Ala Lys
        115                 120                 125

Ala Arg Thr Met Asn Pro Ser Tyr Lys Val Ile Ala Thr Gly His Ser
130                 135                 140

Leu Gly Gly Ala Val Ala Thr Leu Gly Ala Ala Asp Leu Arg Ser Lys
145                 150                 155                 160

Gly Thr Ala Val Asp Ile Phe Thr Phe Gly Ala Pro Arg Val Gly Asn
                165                 170                 175

Ala Glu Leu Ser Ala Phe Ile Thr Ala Gln Ala Gly Gly Glu Phe Arg
            180                 185                 190

Val Thr His Gly Arg Asp Pro Val Pro Arg Leu Pro Pro Ile Val Phe
        195                 200                 205

Gly Tyr Arg His Thr Ser Pro Glu Tyr Trp Leu Ala Gly Gly Ala Ser
210                 215                 220

Thr Lys Thr Asp Tyr Thr Val Asn Asp Ile Lys Val Cys Glu Gly Ala
225                 230                 235                 240

Ala Asn Leu Ala Cys Asn Gly Gly Thr Leu Gly Leu Asp Ile Ile Ala
                245                 250                 255

His Leu Arg Tyr Phe Gln Asp Thr Asp Ala Cys Thr Ala Gly Gly Ile
            260                 265                 270

Ser Trp Lys Arg Gly Asp Lys Ala Lys Arg Asp Glu Ile Pro Lys Arg
        275                 280                 285

Gln Glu Gly Met Thr Asp Glu Glu Leu Glu Gln Lys Leu Asn Asp Tyr
    290                 295                 300

Val Ala Met Asp Lys Glu Tyr Val Glu Ser Asn Lys Met
305                 310                 315
```

<210> SEQ ID NO 2
<211> LENGTH: 954
<212> TYPE: DNA
<213> ORGANISM: Fusarium solani

<400> SEQUENCE: 2
gccattactg cttctcaatt ggactacgaa aacttcaagt tttacatcca gcacggtgcc      60

```
gctgcttact gtaactccga aactgcctct ggtcaaaaga tcacttgttc cgacaacggt    120
tgcaaaggtg tcgaagctaa caacgctatt attgtcgcct ctttcgttgg aaaaggtact    180
ggtattggtg gttacgtttc tactgataac gttagaaagg agatcgtttt gtctattaga    240
ggttcttcca acattcgtaa ctggttgact aacgtcgact tcggacaatc ctcttgttct    300
tacgttagag attgtggagt tcacactggt ttcagaaatg cttgggacga gattgcccaa    360
agagctagag acgctgtcgc taaagctaga actatgaacc catcttacaa ggttatcgct    420
actggtcact ctttgggtgg tgctgttgcc actttgggtg ctgctgattt gagatccaag    480
ggtactgccg tcgatatctt tacttttggt gccccaagag ttggtaacgc tgagttgtcc    540
gctttcatca ctgctcaggc tggtggtgag ttcagagtta ctcacggacg tgatccagtt    600
ccacgtttgc cacctatcgt cttcggttac agacacacct ctccagagta ctggttggct    660
ggtggtgctt ccaccaagac tgattatact gttaacgata tcaaggtttg tgaaggtgcc    720
gctaacttgg cctgtaatgg tggtactttg ggattggata tcattgctca tttgagatac    780
ttccaagaca ctgacgcctg tactgctggt ggtatctcct ggaagagagg tgacaaagct    840
aagagagatg agattccaaa aagacaagaa ggaatgactg atgaggagtt ggaacaaaaa    900
ctgaacgact atgtcgccat ggataaggag tacgttgagt ccaacaagat gtaa          954
```